(12) United States Patent
Dousson et al.

(10) Patent No.: US 9,339,541 B2
(45) Date of Patent: May 17, 2016

(54) THIOPHOSPHATE NUCLEOSIDES FOR THE TREATMENT OF HCV

(71) Applicant: IDENIX PHARMACEUTICALS, INC., Cambridge, MA (US)

(72) Inventors: Cyril B. Dousson, Canet (FR); Benjamin Alexander Mayes, Boston, MA (US); David Dukhan, Saint Gely du Fesc (FR); Adel M. Moussa, Burlington, MA (US); Alistair James Stewart, Lincoln, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/195,635

(22) Filed: Mar. 3, 2014

(65) Prior Publication Data

US 2014/0248242 A1    Sep. 4, 2014

Related U.S. Application Data

(60) Provisional application No. 61/772,331, filed on Mar. 4, 2013.

(51) Int. Cl.

| | |
|---|---|
| C07H 19/10 | (2006.01) |
| C07H 19/11 | (2006.01) |
| C07H 19/20 | (2006.01) |
| C07H 19/213 | (2006.01) |
| A61K 45/06 | (2006.01) |
| A61K 31/7076 | (2006.01) |
| A61K 31/7072 | (2006.01) |
| A61K 31/708 | (2006.01) |
| C07H 19/16 | (2006.01) |
| C07H 19/06 | (2006.01) |
| C07H 19/207 | (2006.01) |

(52) U.S. Cl.
CPC ............... *A61K 45/06* (2013.01); *A61K 31/708* (2013.01); *A61K 31/7072* (2013.01); *A61K 31/7076* (2013.01); *C07H 19/06* (2013.01); *C07H 19/10* (2013.01); *C07H 19/11* (2013.01); *C07H 19/16* (2013.01); *C07H 19/20* (2013.01); *C07H 19/207* (2013.01); *C07H 19/213* (2013.01)

(58) Field of Classification Search
None
See application file for complete search history.

(56) References Cited

U.S. PATENT DOCUMENTS

| | | | |
|---|---|---|---|
| 3,480,613 A | 11/1969 | Walton et al. | |
| 6,174,868 B1 | 1/2001 | Anderson et al. | |
| 6,284,458 B1 | 9/2001 | Anderson et al. | |
| 6,348,587 B1 | 2/2002 | Schinazi et al. | |
| 6,391,542 B1 | 5/2002 | Anderson et al. | |
| 6,423,489 B1 | 7/2002 | Anderson et al. | |
| 6,433,159 B1 | 8/2002 | Anderson | |
| 6,455,513 B1 | 9/2002 | McGuigan et al. | |
| 6,566,365 B1 | 5/2003 | Storer | |
| 6,573,247 B1 | 6/2003 | McGuigan et al. | |
| 6,608,191 B1 | 8/2003 | Anderson et al. | |
| 6,638,919 B2 | 10/2003 | McGuigan et al. | |
| 6,660,721 B2 | 12/2003 | Devos et al. | |
| 6,777,395 B2 | 8/2004 | Bhat et al. | |
| 6,784,161 B2 | 8/2004 | Ismaili et al. | |
| 6,784,166 B2 | 8/2004 | Devos et al. | |
| 6,833,361 B2 | 12/2004 | Hong et al. | |
| 6,846,810 B2 | 1/2005 | Martin et al. | |
| 6,911,424 B2 | 6/2005 | Schinazi et al. | |
| 6,914,054 B2 | 7/2005 | Sommadossi et al. | |
| 6,927,291 B2 | 8/2005 | Jin et al. | |
| 6,995,146 B2 | 2/2006 | Anderson et al. | |
| 7,018,989 B2 | 3/2006 | McGuigan et al. | |
| 7,019,135 B2 | 3/2006 | McGuigan et al. | |
| 7,094,770 B2 | 8/2006 | Watanabe et al. | |
| 7,105,493 B2 | 9/2006 | Sommadossi et al. | |
| 7,105,499 B2 | 9/2006 | Carroll et al. | |
| 7,115,590 B1 | 10/2006 | Daluge et al. | |
| 7,125,855 B2 | 10/2006 | Bhat et al. | |

(Continued)

FOREIGN PATENT DOCUMENTS

| | | |
|---|---|---|
| CN | 1133642 C | 1/2004 |
| WO | WO 93/17651 | 9/1993 |

(Continued)

OTHER PUBLICATIONS

International Search Report and Written Opinion in PCT/US2014/019997, mailed May 15, 2014, 10 pages.

(Continued)

*Primary Examiner* — Traviss C McIntosh, III

(74) *Attorney, Agent, or Firm* — Jeffrey P. Bergman; Mark R. Daniel

(57) ABSTRACT

Provided herein are compounds, compositions and methods for the treatment of Flaviviridae infections, including HCV infections. In certain embodiments, the compounds are according to Formula 2001:

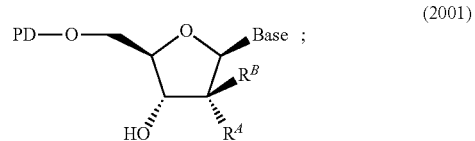

(2001)

where PD, Base, $R^A$ and $R^B$ are as provided herein. In certain embodiments, compounds and compositions of nucleoside derivatives are disclosed, which can be administered either alone or in combination with other anti-viral agents.

20 Claims, No Drawings

(56) References Cited

U.S. PATENT DOCUMENTS

| | | |
|---|---|---|
| 7,138,376 B2 | 11/2006 | Gosselin et al. |
| 7,148,206 B2 | 12/2006 | Sommadossi et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,192,936 B2 | 3/2007 | LaColla et al. |
| 7,202,224 B2 | 4/2007 | Eldrup et al. |
| 7,300,924 B2 | 11/2007 | Boojamra et al. |
| 7,307,065 B2 | 12/2007 | Schinazi et al. |
| 7,323,449 B2 | 1/2008 | Olsen et al. |
| 7,323,453 B2 | 1/2008 | Olsen et al. |
| 7,339,054 B2 | 3/2008 | Xu et al. |
| 7,365,057 B2 | 4/2008 | LaColla et al. |
| 7,378,402 B2 | 5/2008 | Martin et al. |
| 7,384,924 B2 | 6/2008 | LaColla et al. |
| 7,405,204 B2 | 7/2008 | Roberts et al. |
| 7,429,572 B2 | 9/2008 | Clark |
| 7,452,901 B2 | 11/2008 | Boojamra et al. |
| 7,456,155 B2 | 11/2008 | Sommadossi et al. |
| 7,524,825 B2 | 4/2009 | Keicher et al. |
| 7,534,767 B2 | 5/2009 | Butora et al. |
| 7,547,704 B2 | 6/2009 | LaColla et al. |
| 7,582,618 B2 | 9/2009 | Sommadossi et al. |
| 7,598,373 B2 | 10/2009 | Storer et al. |
| 7,608,597 B2 | 10/2009 | Sommadossi et al. |
| 7,608,599 B2 | 10/2009 | Klumpp et al. |
| 7,608,600 B2 | 10/2009 | Storer et al. |
| 7,608,601 B2 | 10/2009 | Devos et al. |
| 7,625,875 B2 | 12/2009 | Gosselin et al. |
| 7,632,821 B2 | 12/2009 | Butora et al. |
| 7,632,940 B2 | 12/2009 | Harrington et al. |
| 7,635,689 B2 | 12/2009 | LaColla et al. |
| 7,645,745 B2 | 1/2010 | Sarma |
| 7,645,747 B2 | 1/2010 | Boojamra et al. |
| 7,662,798 B2 | 2/2010 | LaColla et al. |
| 7,666,856 B2 | 2/2010 | Johansson et al. |
| 7,754,699 B2 | 7/2010 | Chun et al. |
| 7,772,208 B2 | 8/2010 | Schinazi et al. |
| 7,781,576 B2 | 8/2010 | Mayes et al. |
| 7,820,631 B2 | 10/2010 | McGuigan et al. |
| 7,824,851 B2 | 11/2010 | Sommadossi et al. |
| 7,842,672 B2 | 11/2010 | Boojamra et al. |
| 7,871,991 B2 | 1/2011 | Boojamra et al. |
| 7,879,815 B2 | 2/2011 | MacCoss et al. |
| 7,902,202 B2 | 3/2011 | Sommadossi et al. |
| 7,915,232 B2 | 3/2011 | Martin et al. |
| 7,951,787 B2 | 5/2011 | McGuigan |
| 7,951,789 B2 | 5/2011 | Sommadossi et al. |
| 7,964,580 B2 | 6/2011 | Sofia et al. |
| 7,973,013 B2 | 7/2011 | Cho et al. |
| 8,008,264 B2 | 8/2011 | Butler et al. |
| 8,012,941 B2 | 9/2011 | Cho et al. |
| 8,012,942 B2 | 9/2011 | Butler et al. |
| 8,022,083 B2 | 9/2011 | Boojamra et al. |
| 8,071,567 B2 | 12/2011 | Devos et al. |
| 8,119,607 B2 | 2/2012 | Francom et al. |
| 8,119,779 B2 | 2/2012 | McGuigan et al. |
| 8,148,349 B2 | 4/2012 | Meppen et al. |
| 8,168,583 B2 | 5/2012 | Schinazi et al. |
| 8,173,621 B2 | 5/2012 | Du et al. |
| 8,183,216 B2 | 5/2012 | Di Francesco et al. |
| 8,236,779 B2 | 8/2012 | Ma et al. |
| 8,299,038 B2 | 10/2012 | Sommadossi et al. |
| 8,318,682 B2 | 11/2012 | Butler et al. |
| 8,318,701 B2 | 11/2012 | Boojamra et al. |
| 8,324,179 B2 | 12/2012 | Chen et al. |
| 8,329,926 B2 | 12/2012 | Boojamra et al. |
| 8,334,270 B2 | 12/2012 | Sofia et al. |
| 8,399,428 B2 | 3/2013 | Wagner |
| 8,404,651 B2 | 3/2013 | Iyer et al. |
| 8,415,308 B2 | 4/2013 | Cho et al. |
| 8,415,322 B2 | 4/2013 | Clark |
| 8,455,451 B2 | 6/2013 | Cho et al. |
| 8,481,713 B2 | 7/2013 | Wang et al. |
| 8,507,460 B2 | 8/2013 | Surleraux et al. |
| 8,551,973 B2 | 10/2013 | Bao et al. |
| 8,552,021 B2 | 10/2013 | Jonckers et al. |
| 8,563,530 B2 | 10/2013 | Chang et al. |
| 8,569,478 B2 | 10/2013 | Du et al. |
| 8,575,119 B2 | 11/2013 | Wang et al. |
| 8,580,765 B2 | 11/2013 | Sofia et al. |
| 8,609,627 B2 | 12/2013 | Cho et al. |
| 8,618,076 B2 | 12/2013 | Ross et al. |
| 8,637,475 B1 | 1/2014 | Storer et al. |
| 8,642,756 B2 | 2/2014 | Ross et al. |
| 8,658,616 B2 | 2/2014 | McGuigan et al. |
| 8,680,071 B2 | 3/2014 | Surleraux et al. |
| 8,691,788 B2 | 4/2014 | Sommadossi et al. |
| 8,716,262 B2 | 5/2014 | Sofia et al. |
| 8,716,263 B2 | 5/2014 | Chun et al. |
| 8,728,725 B2 | 5/2014 | Paul et al. |
| 8,735,372 B2 | 5/2014 | Du et al. |
| 8,759,318 B2 | 6/2014 | Chamberlain et al. |
| 8,759,510 B2 | 6/2014 | Du et al. |
| 8,765,710 B2 | 7/2014 | Sofia et al. |
| 8,765,935 B2 | 7/2014 | Wagner |
| 8,772,474 B2 | 7/2014 | Beigelman et al. |
| 8,802,840 B2 | 8/2014 | Francom et al. |
| 8,816,074 B2 | 8/2014 | Chu et al. |
| 2003/0008841 A1 | 1/2003 | Devos et al. |
| 2003/0087873 A1 | 5/2003 | Stuyver et al. |
| 2004/0014108 A1 | 1/2004 | Eldrup et al. |
| 2004/0110718 A1 | 6/2004 | Devos et al. |
| 2004/0229840 A1 | 11/2004 | Bhat et al. |
| 2004/0266723 A1 | 12/2004 | Otto et al. |
| 2005/0009775 A1 | 1/2005 | Howes et al. |
| 2005/0038240 A1 | 2/2005 | Connolly et al. |
| 2005/0124532 A1 | 6/2005 | Sommadossi et al. |
| 2006/0040944 A1 | 2/2006 | Gosselin et al. |
| 2006/0234962 A1 | 10/2006 | Olsen et al. |
| 2006/0264389 A1 | 11/2006 | Bhat et al. |
| 2007/0004669 A1 | 1/2007 | Carroll et al. |
| 2007/0027065 A1 | 2/2007 | LaColla et al. |
| 2007/0027104 A1 | 2/2007 | LaColla et al. |
| 2007/0032449 A1 | 2/2007 | LaColla et al. |
| 2007/0037735 A1 | 2/2007 | Gosselin et al. |
| 2007/0042990 A1 | 2/2007 | Gosselin et al. |
| 2007/0060503 A1 | 3/2007 | Gosselin et al. |
| 2007/0060504 A1 | 3/2007 | Gosselin et al. |
| 2007/0060505 A1 | 3/2007 | Gosselin et al. |
| 2007/0060541 A1 | 3/2007 | Gosselin et al. |
| 2007/0265222 A1 | 11/2007 | MacCoss et al. |
| 2008/0070861 A1 | 3/2008 | Clark |
| 2008/0139802 A1 | 6/2008 | Axt et al. |
| 2008/0253995 A1 | 10/2008 | Clark |
| 2008/0261913 A1 | 10/2008 | Sommadossi et al. |
| 2008/0280842 A1 | 11/2008 | MacCoss et al. |
| 2009/0004135 A1 | 1/2009 | Clark |
| 2009/0036666 A1 | 2/2009 | Clark |
| 2009/0048189 A1 | 2/2009 | Keicher et al. |
| 2009/0118223 A1 | 5/2009 | Erion et al. |
| 2009/0176732 A1 | 7/2009 | Beigelman et al. |
| 2009/0318380 A1 | 12/2009 | Sofia et al. |
| 2010/0003217 A1 | 1/2010 | Cretton-Scott et al. |
| 2010/0056468 A1 | 3/2010 | Kotra et al. |
| 2010/0077085 A1 | 3/2010 | Cohen |
| 2010/0240604 A1 | 9/2010 | Beigelman et al. |
| 2010/0249068 A1 | 9/2010 | Beigelman et al. |
| 2010/0279969 A1 | 11/2010 | Schinazi et al. |
| 2010/0279974 A1 | 11/2010 | Pierra et al. |
| 2010/0297079 A1 | 11/2010 | Almond et al. |
| 2010/0316594 A1 | 12/2010 | Sommadossi et al. |
| 2011/0217261 A1 | 9/2011 | Or et al. |
| 2011/0245484 A1 | 10/2011 | Ross et al. |
| 2011/0269707 A1 | 11/2011 | Stuyver et al. |
| 2011/0306541 A1 | 12/2011 | Delaney, IV et al. |
| 2011/0306573 A1 | 12/2011 | Avolio et al. |
| 2012/0010164 A1 | 1/2012 | Surnma et al. |
| 2012/0034184 A1 | 2/2012 | Devos et al. |
| 2012/0035115 A1 | 2/2012 | Manoharan et al. |
| 2012/0070411 A1 | 3/2012 | Beigelman et al. |
| 2012/0070415 A1 | 3/2012 | Beigelman et al. |
| 2012/0071434 A1 | 3/2012 | Smith et al. |
| 2012/0107274 A1 | 5/2012 | Clarke et al. |

(56) References Cited

U.S. PATENT DOCUMENTS

| | | |
|---|---|---|
| 2012/0142626 A1 | 6/2012 | Du et al. |
| 2012/0237480 A1 | 9/2012 | Or et al. |
| 2012/0245335 A1 | 9/2012 | Clark |
| 2012/0251487 A1 | 10/2012 | Surleraux |
| 2012/0263678 A1 | 10/2012 | Cho et al. |
| 2013/0005677 A1 | 1/2013 | Chu et al. |
| 2013/0017171 A1 | 1/2013 | Sommadossi et al. |
| 2013/0064793 A1 | 3/2013 | Surleraux et al. |
| 2013/0149283 A1 | 6/2013 | Sommadossi et al. |
| 2013/0225520 A1 | 8/2013 | Jonckers et al. |
| 2013/0244968 A1 | 9/2013 | Jonckers et al. |
| 2013/0273005 A1 | 10/2013 | Delaney et al. |
| 2013/0281686 A1 | 10/2013 | Cho et al. |
| 2013/0315862 A1 | 11/2013 | Sommadossi et al. |
| 2013/0315866 A1 | 11/2013 | Parsy et al. |
| 2013/0315867 A1 | 11/2013 | Parsy et al. |
| 2013/0315868 A1 | 11/2013 | Mayes et al. |
| 2013/0330297 A1 | 12/2013 | Storer et al. |
| 2014/0086873 A1 | 3/2014 | Mayes et al. |
| 2014/0099283 A1* | 4/2014 | Gosselin et al. ............. 424/85.7 |
| 2014/0112886 A1 | 4/2014 | Moussa et al. |
| 2014/0112887 A1 | 4/2014 | Mayes et al. |
| 2014/0113880 A1 | 4/2014 | Storer et al. |
| 2014/0140951 A1 | 5/2014 | Moussa et al. |
| 2014/0140952 A1 | 5/2014 | Moussa et al. |
| 2014/0154211 A1 | 6/2014 | Girijavallabhan et al. |
| 2014/0161770 A1 | 6/2014 | Girijavallabhan et al. |
| 2014/0178338 A1 | 6/2014 | Mayes et al. |
| 2014/0206640 A1 | 7/2014 | Girijavallabhan et al. |

FOREIGN PATENT DOCUMENTS

| | | |
|---|---|---|
| WO | WO 03/105770 A2 | 12/2003 |
| WO | WO 2005/020884 A2 | 3/2005 |
| WO | WO 2005/020885 A2 | 3/2005 |
| WO | WO 2007/027248 A2 | 3/2007 |
| WO | WO 2012/048013 A2 | 4/2012 |
| WO | WO 2012/092484 A2 | 7/2012 |
| WO | WO 2012/158811 A2 | 11/2012 |
| WO | WO 2013/009735 A1 | 1/2013 |
| WO | WO 2013/009737 A1 | 1/2013 |
| WO | WO 2013/013009 A2 | 1/2013 |
| WO | WO 2013/084165 A1 | 6/2013 |
| WO | WO 2013/092447 A1 | 6/2013 |
| WO | WO 2013/092481 A1 | 6/2013 |
| WO | WO 2013/106344 A1 | 7/2013 |
| WO | WO 2014/059901 A1 | 4/2014 |
| WO | WO 2014/059902 A1 | 4/2014 |
| WO | WO 2014/062596 A1 | 4/2014 |

OTHER PUBLICATIONS

Congiatu et al., Novel Potential Anticancer Naphthyl Phosphoramidates of BVdU: Separation of Diastereoisomers and Assignment of the Absolute Configuration of the Phosphorus Center (2006) *Journal of Medicinal Chemistry* 49:452-455.

Eldrup et al., Structure-Activity Relationship of Purine Ribonucleosides for Inhibition of Hepatitis C Virus RNA-Dependent RNA Polymerase (2004) *Journal of Medicinal Chemistry* 47:2283-2295.

Gardelli et al., Phosphoramidate Prodrugs of 2'-C-Methylcytidine for Therapy of Hepatitis C Virus Infection (2009) *Journal of Medicinal Chemistry* 52:5394-5407.

Hollecker et al., Synthesis of β-enantiomers of $N^4$-hydroxy-3'-deoxypyrimidine nucleosides and their evaluation against bovine viral diarrhoea virus and hepatitis C virus in cell culture (2004) *Antiviral Chemistry & Chemotherapy* 14:43-55.

Ivanov et al., Synthesis and biological properties of pyrimidine 4'-fluoronucleosides and 4'-fluorouridine 5'-O-triphosphate (2010) *Russian Journal of Bioorganic Chemistry* 36:488-496.

Kakefuda et al., Nucleosides and nucleotides. 120. Stereoselective radical deoxygenation of *tert*-alcohols in the sugar moiety of nucleosides: synthesis of 2',3'-dideoxy-2'-C-methyl-2'-C-ethynyl-β-d-*threo*-pentofuranosyl pyrimidines and adenine as potential antiviral and antitumor agents (1993) *Tetrahedron* 49:8513-8528.

Kawana et al., The deoxygenations of tosylated adenosine derivatives with Grignard reagents (1986) *Nucleic Acids Symp Ser.* 17:37-40.

Kawana et al., The Synthesis of C-Methyl Branched-Chain Deoxy Sugar Nucleosides by the Deoxygenative Methylation of O-Tosylated Adenosines with Grignard Reagents (1988) *Bull. Chem. Soc. Jpn.* 61:2437-2442.

King et al., Inhibition of the replication of a hepatitis C virus-like RNA template by interferon and 3'-deoxycytidine (2002) *Antiviral Chemistry & Chemotherapy* 13:363-370.

Leisvuori et al., Synthesis of 3',5'-Cyclic Phosphate and Thiophosphate Esters of 2'-C-Methyl Ribonucleosides (2012) *Helvetica Chimica Acta* 95:1512-1520.

McGuigan et al., Phosphoramidate ProTides of 2'-C-Methylguanosine as Highly Potent Inhibitors of Hepatitis C Virus. Study of Their in Vitro and in Vivo Properties (2010) *Journal of Medicinal Chemistry* 53:4949-4957.

McGuigan et al., Phosphorodiamidates as a Promising New Phosphate Prodrug Motif for Antiviral Drug Discovery: Application to Anti-HCV Agents (2011) *Journal of Medicinal Chemistry* 54:8632-8645.

McGuigan et al., the application of phosphoramidate ProTide technology to the potent anti-HCV compound 4'-azidocytidine (R1479) (2009) *Bioorganic & Medicinal Chemistry Letters* 19:4250-4254.

Mehellou et al., Phosphoramidates of 2'β-D-arabinouridine (AraU) as phosphate prodrugs; design, synthesis, in vitro activity and metabolism (2010) *Bioorganic & Medicinal Chemistry* 18:2439-2446.

Mehellou et al., The design, synthesis and antiviral evaluation of a series of 5-trimethylsilyl-1-β-D-(arabinofurano syl)uracil phosphoramidate ProTides (2010) *Antiviral Chemistry & Chemotherapy* 20:153-160.

Murakami et al., Mechanism of Activation of PSI-7851 and Its Diastereoisomer PSI-7977 (2010) *Journal of Biological Chemistry* 285:34337-34347.

Murakami et al., Mechanism of Activation of β-D-2'-Deoxy-2'-Fluoro-2'-C-Methylcytidine and Inhibition of Hepatitis C Virus NS5B RNA polymerase (2007) *Antimicrobial Agents and Chemotherapy* 51:503-509.

Nillroth, et al., Specific interaction between HIV-1 proteinase and 5'-phosphate peptidomimetic derivatives of nucleoside analogues (1995) *Drug Design and Discovery* 13:43-54.

Nillroth et al., The use of 5'-phosphate derivatives of nucleoside analogues as inhibitors of HIV-1 replication (1995) *Antiviral Chemistry & Chemotherapy* 6:50-64.

Olsen et al., A 7-Deaza-Adenosine Analog Is a Potent and Selective Inhibitor of Hepatitis C Virus Replication with Excellent Pharmacokinetic Properties (2004) *Antimicrobial Agents and Chemotherapy* 28:3944-3953.

Perrone et al., Application of the Phosphoramidate ProTide Approach to 4'-Azidouridine Confers Sub-micromolar Potency versus Hepatitis C Virus on an Inactive Nucleoside (2007) *Journal of Medicinal Chemistry* 50:1840-1849.

Pierra et al., Synthesis of 2'-C-Methylcytidine and 2'-C-Methyluridine Derivatives Modified in the 3'-Position as Potential Antiviral Agents (2006) *Collection of Czechoslovak Chemical Communications* 71:991-1010.

Prakash et al., Synthesis and Evaluation of S-Acyl-2-thioethyl Esters of Modified Nucleoside 5'-Monophosphates as Inhibitors of Hepatitis C Virus RNA Replication (2005) *J. Med. Chem.* 48:1199-1210.

Saboulard et al., Characterization of the Activation Pathway of Phosphoramidate Triester Prodrugs of Stavudine and Zidovudine (2009) *Molecular Pharmacology* 56:693-704.

Shen et al., Design and synthesis of vidarabine prodrugs as antiviral agents (2009) *Bioorganic & Medicinal Chemistry Letters* 19:792-796.

Sofia et al., Discovery of a β-D-2'-Deoxy-2'-α-fluoro-2'-β-C-methyluridine Nucleotide Prodrug (Psi-7977) for the Treatment of Hepatitis C Virus (2010) *Journal of Medicinal Chemistry* 53:7202-7218.

(56) References Cited

OTHER PUBLICATIONS

Stein et al., Phosphorylation of Nucleoside Analog Antiretrovirals: A Review for Clinicians (2001) *Pharmacotherapy* 21:11-34.
Tomassini et al., Inhibitory Effect of 2'-Substituted Nucleosides on Hepatitis C Virus Replication Correlates with Metabolic Properties in Replicon Cells (2005) *Antimicrobial Agents and Chemotherapy* 49:2050-2058.
Tong et al., Nucleosides of thioguanine and other 2-amino-6-substituted purines from 2-acetamido-5-chloropurine (1967) *J Org Chem.* 32:859-62.

* cited by examiner

THIOPHOSPHATE NUCLEOSIDES FOR THE TREATMENT OF HCV

FIELD

Provided herein are compounds, methods, and pharmaceutical compositions for use in treatment of viral infections, including hepatitis C virus infections in hosts in need thereof. In certain embodiments, thiophosphate nucleosides are provided which display remarkable efficacy and bioavailability for the treatment of, for example, HCV infection in a human.

BACKGROUND

The hepatitis C virus (HCV) is the leading cause of chronic liver disease worldwide. (Boyer, N. et al., *J. Hepatol.* 32:98-112, 2000). HCV causes a slow growing viral infection and is the major cause of cirrhosis and hepatocellular carcinoma (Di Besceglie, A. M. and Bacon, B. R., *Scientific American*, October: 80-85, 1999; Boyer, N. et al., *J. Hepatol.* 32:98-112, 2000). It is estimated there are about 130-170 million people with chronic hepatitis C virus infection, and there are about 350,000 deaths from hepatitis C-related liver diseases each year (Hepatitis C Fact Sheet, *World Health Organization Fact Sheet No.* 164, June 2011). Cirrhosis caused by chronic hepatitis C infection accounts for 8,000-12,000 deaths per year in the United States, and HCV infection is the leading indication for liver transplantation.

HCV infection becomes chronic in about 75% of cases, with many patients initially being asymptomatic. The first symptoms of HCV infection are often those of chronic liver disease. About 20 to 30% of patients with chronic hepatitis due to HCV develop cirrhosis, although this may take decades. Development of cirrhosis due to HCV also increases the risk of hepatocellular cancer (The Merck Manual Online, *Chronic Hepatitis*, available at www.merckmanuals.com/professional/hepatic_and_biliary_disorders/hepatitis/chronic_hepatitis. html, last revision February 2007).

In light of the fact that HCV infection has reached epidemic levels worldwide, and has tragic effects on the infected patient, there remains a strong need to provide new effective pharmaceutical agents to treat hepatitis C that have low toxicity to the host. Further, given the rising threat of other flaviviridae infections, there remains a strong need to provide new effective pharmaceutical agents that have low toxicity to the host. Therefore, there is a continuing need for effective treatments of flavivirus infections and HCV infections.

SUMMARY

Provided herein are compounds useful, for example, for the treatment of flavivirus infections such as HCV infections. The compounds are thiophosphate nucleosides. In certain embodiments the thiophosphate nucleosides display remarkable efficacy or bioavailability, or both, for the treatment of, for example, HCV infection in a human.

In certain embodiments, the compounds provided herein are useful in the prevention and treatment of Flaviviridae infections and other related conditions such as anti-Flaviviridae antibody positive and Flaviviridae-positive conditions, chronic liver inflammation caused by HCV, cirrhosis, fibrosis, acute hepatitis, fulminant hepatitis, chronic persistent hepatitis, and fatigue. These compounds or formulations can also be used prophylactically to prevent or retard the progression of clinical illness in individuals who are anti-Flaviviridae antibody or Flaviviridae-antigen positive or who have been exposed to a Flaviviridae. In particular embodiments, the Flaviviridae is hepatitis C. In certain embodiments, the compounds are used to treat any virus that replicates through an RNA-dependent RNA polymerase.

A method for the treatment of a Flaviviridae infection in a host, including a human, is also provided that includes administering an effective amount of a compound provided herein, administered either alone or in combination or alternation with another anti-Flaviviridae agent, optionally in a pharmaceutically acceptable carrier.

In certain embodiments, provided herein are compounds according to Formula 2001:

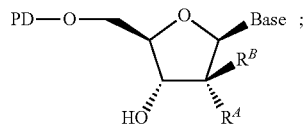

(2001)

or a pharmaceutically acceptable salt, solvate, stereoisomeric form, tautomeric form, or polymorphic form thereof, wherein:
Base is a nucleobase;
$R^A$ is hydroxyl or halo;
$R^B$ is methyl or halo;
PD is

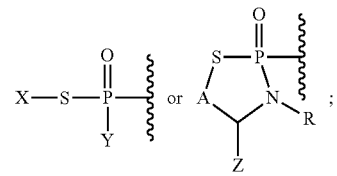

X is alkyl, alkoxycarbonylalkyl, (alkoxycarbonyl)(alkoxycarbonylamino)alkyl, cycloalkyl, heterocycloalkyl, hydantoinylalkyl, or aryl;
Y is —$NR^1R^2$ or an N-linked or O-linked amino acid residue, or a derivative thereof;
Z is alkyl, alkoxycarbonyl, or alkoxyalkylcarbonyl;
A is —$CHR^{10}$—, —$CHR^{10}CHR^{11}$—, or —$CHR^{10}CHR^{11}CHR^{12}$—;
$R^1$ is hydrogen, alkyl, cycloalkyl, aryl, heteroaryl, arylalkyl, or heteroarylalkyl;
$R^2$ is hydrogen or alkyl;
R is hydrogen or alkyl; and
each of $R^{10}$, $R^{11}$, and $R^{12}$ is independently hydrogen or alkyl; or $R^{10}$ and $R^{11}$, together with the carbon atoms to which they are attached, combine to form a five-, six-, or seven-membered ring.

In certain embodiments, provided herein are compounds according to Formula (I):

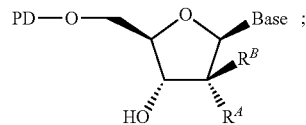

(I)

or a pharmaceutically acceptable salt, solvate, stereoisomeric form, tautomeric form, or polymorphic form thereof, wherein: Base is a nucleobase; $R^A$ is hydroxyl or halo; $R^B$ is methyl or halo; PD is

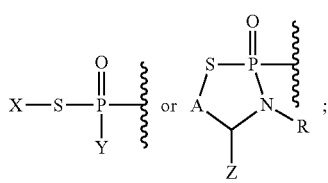

X is alkyl, alkoxycarbonylalkyl, (alkoxycarbonyl)(alkoxycarbonylamino)alkyl, cycloalkyl, heterocycloalkyl, hydantoinylalkyl, or aryl; Y is —NR$^1$R$^2$ or an N-linked amino acid, or ester thereof; Z is alkyl, alkoxycarbonyl or alkoxyalkylcarbonyl; A is —CHR$^{10}$—, —CHR$^{10}$CHR$^{11}$—, or —CHR$^{10}$CHR$^{11}$CHR$^{12}$—; R$^1$ is hydrogen, alkyl, cycloalkyl, aryl, heteroaryl, arylalkyl, or heteroarylalkyl; R$^2$ is hydrogen or alkyl; R is hydrogen or alkyl; and each of R$^{10}$, R$^{11}$, and R$^{12}$ is independently hydrogen or alkyl; or R$^{10}$ and R$^{11}$, together with the carbon atoms to which they are attached, combine to form a five-, six-, or seven-membered ring.

In one aspect, the compounds provided herein are provided or administered in combination with a second therapeutic agent, such as one useful for the treatment or prevention of HCV infections. Exemplary second therapeutic agents are provided in detail elsewhere herein.

In another aspect, provided herein are pharmaceutical compositions, single unit dosage forms, and kits suitable for use in treating or preventing disorders such as HCV infections which comprise a therapeutically or prophylactically effective amount of a compound provided herein, e.g., of Formula 2001, I-XXIX, 1-23byii and 1001-1002 and a therapeutically or prophylactically effective amount of a second therapeutic agent such as one useful for the treatment or prevention of HCV infections.

In certain embodiments, a method of treatment of a liver disorder is provided comprising administering to an individual in need thereof a treatment effective amount of a thiophosphate nucleoside compound.

Flaviviridae which can be treated are, e.g., discussed generally in *Fields Virology*, Fifth Ed., Editors: Knipe, D. M., and Howley, P. M., Lippincott Williams & Wilkins Publishers, Philadelphia, Pa., Chapters 33-35, 2006. In a particular embodiment of the invention, the Flaviviridae is HCV. In an alternate embodiment, the Flaviviridae is a flavivirus or pestivirus. In certain embodiments, the Flaviviridae can be from any class of Flaviviridae. In certain embodiments, the Flaviviridae is a mammalian tick-borne virus. In certain embodiments, the Flaviviridae is a seabird tick-borne virus. In certain embodiments, the Flaviviridae is a mosquito-borne virus. In certain embodiments, the Flaviviridae is an Aroa virus. In certain embodiments, the Flaviviridae is a Dengue virus. In certain embodiments, the Flaviviridae is a Japanese encephalitis virus. In certain embodiments, the Flaviviridae is a Kokobera virus. In certain embodiments, the Flaviviridae is a Ntaya virus. In certain embodiments, the Flaviviridae is a Spondweni virus. In certain embodiments, the Flaviviridae is a Yellow fever virus. In certain embodiments, the Flaviviridae is a Entebbe virus. In certain embodiments, the Flaviviridae is a Modoc virus. In certain embodiments, the Flaviviridae is a Rio Bravo virus.

Specific flaviviruses which can be treated include, without limitation: Absettarov, Aedes, Alfuy, Alkhurma, Apoi, Aroa, Bagaza, Banzi, Bukalasa bat, Bouboui, Bussuquara, Cacipacore, Calbertado, Carey Island, Cell fusing agent, Cowbone Ridge, Culex, Dakar bat, Dengue 1, Dengue 2, Dengue 3, Dengue 4, Edge Hill, Entebbe bat, Gadgets Gully, Hanzalova, Hypr, Ilheus, Israel turkey meningoencephalitis, Japanese encephalitis, Jugra, Jutiapa, Kadam, Kamiti River, Karshi, Kedougou, Kokobera, Koutango, Kumlinge, Kunjin, Kyasanur Forest disease, Langat, Louping ill, Meaban, Modoc, Montana myotis leukoencephalitis, Murray valley encephalitis, Nakiwogo, Naranjal, Negishi, Ntaya, Omsk hemorrhagic fever, Phnom-Penh bat, Powassan, Quang Binh, Rio Bravo, Rocio, Royal Farm, Russian spring-summer encephalitis, Saboya, St. Louis encephalitis, Sal Vieja, San Perlita, Saumarez Reef, Sepik, Sokuluk, Spondweni, Stratford, Tembusu, Tick-borne encephalitis, Turkish sheep encephalitis, Tyuleniy, Uganda S, Usutu, Wesselsbron, West Nile, Yaounde, Yellow fever, Yokose, and Zika.

Pestiviruses which can be treated are discussed generally in *Fields Virology*, Fifth Ed., Editors: Knipe, D. M., and Howley, P. M., Lippincott Williams & Wilkins Publishers, Philadelphia, Pa., Chapters 33-35, 2006. Specific pestiviruses which can be treated include, without limitation: bovine viral diarrhea virus ("BVDV"), classical swine fever virus ("CSFV," also called hog cholera virus), and border disease virus ("BDV").

DESCRIPTION OF EXEMPLARY EMBODIMENTS

Provided herein are compounds, compositions and methods useful for treating liver disorders such as HCV infection in a subject. Further provided are dosage forms useful for such methods.

DEFINITIONS

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The term "alkyl," as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms, i.e., $C_1$ to $C_{10}$ alkyl. In certain embodiments, the alkyl group is methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, or 2,3-dimethylbutyl. The term includes both substituted and unsubstituted alkyl groups, including halogenated alkyl groups. In certain embodiments, the alkyl group is a fluorinated alkyl group. Non-limiting examples of moieties with which the alkyl group can be substituted include, but not limited to, halogen (fluoro, chloro, bromo, or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference.

The term "lower alkyl," as used herein, and unless otherwise specified, refers to a saturated straight or branched hydrocarbon having one to six carbon atoms, i.e., $C_1$ to $C_6$ alkyl. In certain embodiments, the lower alkyl group is a primary, secondary, or tertiary hydrocarbon. The term includes both substituted and unsubstituted moieties.

The term "upper alkyl," as used herein, and unless otherwise specified, refers to a saturated straight or branched hydrocarbon having seven to thirty carbon atoms, i.e., $C_7$ to $C_{30}$ alkyl. In certain embodiments, the upper alkyl group is a primary, secondary, or tertiary hydrocarbon. The term includes both substituted and unsubstituted moieties.

The term "cycloalkyl," as used herein, unless otherwise specified, refers to a saturated cyclic hydrocarbon. In certain embodiments, the cycloalkyl group may be a saturated, and/or bridged, and/or non-bridged, and/or a fused bicyclic group. In certain embodiments, the cycloalkyl group includes three to ten carbon atoms, i.e., $C_3$ to $C_{10}$ cycloalkyl. In some embodiments, the cycloalkyl has from 3 to 15 ($C_{3-15}$), from 3 to 10 ($C_{3-10}$), or from 3 to 7 ($C_{3-7}$) carbon atoms. In certain embodiments, the cycloalkyl group is cyclopropyl, cyclobutyl, cyclopentyl, cyclohexyl, cyclohexylmethyl, cycloheptyl, bicyclo[2.1.1]hexyl, bicyclo[2.2.1]heptyl, decalinyl, or adamantyl. The term includes both substituted and unsubstituted cycloalkyl groups, including halogenated cycloalkyl groups. In certain embodiments, the cycloalkyl group is a fluorinated cycloalkyl group. Non-limiting examples of moieties with which the cycloalkyl group can be substituted include, but not limited to, halogen (fluoro, chloro, bromo, or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

"Alkylene" refers to divalent saturated aliphatic hydrocarbon groups particularly having from one to eleven carbon atoms which can be straight-chained or branched. In certain embodiments, the alkylene group contains 1 to 10 carbon atoms. The term includes both substituted and unsubstituted moieties. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like. The term includes halogenated alkylene groups. In certain embodiments, the alkylene group is a fluorinated alkylene group. Non-limiting examples of moieties with which the alkylene group can be substituted include, but not limited to, halogen (fluoro, chloro, bromo, or iodo), hydroxyl, carbonyl, sulfanyl, amino, alkylamino, alkylaryl, arylamino, alkoxy, aryloxy, nitro, cyano, sulfonic acid, sulfate, phosphonic acid, phosphate, and phosphonate, either unprotected, or protected as necessary.

"Alkenyl" refers to monovalent olefinically unsaturated hydrocarbon groups, in certain embodiment, having up to about 11 carbon atoms, from 2 to 8 carbon atoms, or from 2 to 6 carbon atoms, which can be straight-chained or branched and having at least 1 or from 1 to 2 sites of olefinic unsaturation. The term includes both substituted and unsubstituted moieties. Exemplary alkenyl groups include ethenyl (i.e., vinyl or —$CH$=$CH_2$), n-propenyl (—$CH_2CH$=$CH_2$), isopropenyl (—$C(CH_3)$=$CH_2$), and the like. The term includes halogenated alkenyl groups. In certain embodiments, the alkenyl group is a fluorinated alkenyl group. Non-limiting examples of moieties with which the alkenyl group can be substituted include, but not limited to, halogen (fluoro, chloro, bromo, or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

The term "cycloalkenyl," as used herein, unless otherwise specified, refers to an unsaturated cyclic hydrocarbon. In certain embodiments, cycloalkenyl refers to mono- or multicyclic ring systems that include at least one double bond. In certain embodiments, the cycloalkenyl group may be a bridged, non-bridged, and/or a fused bicyclic group. In certain embodiments, the cycloalkyl group includes three to ten carbon atoms, i.e., $C_3$ to $C_{10}$ cycloalkyl. In some embodiments, the cycloalkenyl has from 3 to 7 ($C_{3-10}$), or from 4 to 7 ($C_{4-7}$) carbon atoms. The term includes both substituted and unsubstituted cycloalkenyl groups, including halogenated cycloalkenyl groups. In certain embodiments, the cycloalkenyl group is a fluorinated cycloalkenyl group. Non-limiting examples of moieties with which the cycloalkenyl group can be substituted include, but not limited to, halogen (fluoro, chloro, bromo, or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

"Alkenylene" refers to divalent olefinically unsaturated hydrocarbon groups, in certain embodiments, having up to about 11 carbon atoms or from 2 to 6 carbon atoms which can be straight-chained or branched and having at least 1 or from 1 to 2 sites of olefinic unsaturation. This term is exemplified by groups such as ethenylene (—$CH$=$CH$—), the propenylene isomers (e.g., —$CH$=$CHCH_2$— and —$C(CH_3)$=$CH$— and —$CH$=$C(CH_3)$—) and the like. The term includes both substituted and unsubstituted alkenylene groups, including halogenated alkenylene groups. In certain embodiments, the alkenylene group is a fluorinated alkenylene group. Non-limiting examples of moieties with which the alkenylene group can be substituted include, but not limited to, halogen (fluoro, chloro, bromo, or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

"Alkynyl" refers to acetylenically unsaturated hydrocarbon groups, in certain embodiments, having up to about 11 carbon atoms or from 2 to 6 carbon atoms which can be straight-chained or branched and having at least 1 or from 1 to 2 sites of alkynyl unsaturation. Non-limiting examples of alkynyl groups include acetylenic, ethynyl (—C≡CH), propargyl (—$CH_2$C≡CH), and the like. The term includes both substituted and unsubstituted alkynyl groups, including halogenated alkynyl groups. In certain embodiments, the alkynyl group is a fluorinated alkynyl group. Non-limiting examples of moieties with which the alkynyl group can be substituted include, but not limited to, halogen (fluoro, chloro, bromo, or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

The term "aryl," as used herein, and unless otherwise specified, refers to a substituent derived from an aromatic ring. In an embodiment, an aryl group is a $C_6$-$C_{12}$ aryl group. In an embodiment, an aryl group is phenyl, biphenyl, or naphthyl. The term includes both substituted and unsubstituted moieties. An aryl group can be substituted with any described moiety, including, but not limited to, one or more moieties selected from halogen (fluoro, chloro, bromo, or iodo), alkyl, haloalkyl, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

"Alkoxy" refers to the group —OR' where R' is alkyl or cycloalkyl. Alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to a radical —C(O)-alkoxy where alkoxy is as defined herein.

"Alkoxyalkylcarbonyl" refers to a radical —C(O)-alkyl-alkoxy where alkoxy and alkyl are as defined herein.

"Alkoxycarbonylalkyl" refers to a radical -alkyl-C(O)-alkoxy where alkoxy and alkyl are as defined herein.

"Alkoxycarbonylamino" refers to a radical -amino-C(O)-alkoxy where alkoxy and amino are as defined herein.

As used herein, "(alkoxycarbonyl)(alkoxycarbonylamino) alkyl" refers to an alkyl radical substituted with both an alkoxycarbonyl and an alkoxycarbonylamino group, where "alkoxycarbonyl" and "alkoxycarbonylamino" are as described herein. In an embodiment, the term refers to a radical of formula

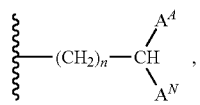

wherein n is an integer selected over the range of 1-10, $A^A$ is —C(O)—O—$R^{100}$, $A^N$ is —NH—C(O)—O—$R^{101}$, and each of $R^{100}$ and $R^{101}$ is independently lower alkyl. In an embodiment, each of $R^{100}$ and $R^{101}$ is independently $C_1$-$C_5$ alkyl.

"Amino" refers to the group —$NR^{1'}R^{2'}$ or —$NR^{1'}$—, wherein $R^{1'}$ and $R^{2'}$ are independently selected from hydrogen, alkyl and cycloalkyl.

"Amino alcohol" refers to the radical —NHLOH, wherein L is alkylene.

"Carboxyl" or "carboxy" refers to the radical —C(O)OH.

The term "alkylamino" or "arylamino" refers to an amino group that has one or two alkyl or aryl substituents, respectively. In certain embodiments, the alkyl substituent is upper alkyl. In certain embodiments, the alkyl substituent is lower alkyl. In another embodiment, the alkyl, upper alkyl, or lower alkyl is unsubstituted.

"Halogen" or "halo" refers to chloro, bromo, fluoro, or iodo.

"Thioalkoxy" refers to the group —SR' where R' is alkyl or cycloalkyl.

The term "heterocyclo" or "heterocyclic" refers to a monovalent monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclo or heterocyclic group has from 3 to 20, from 3 to 15, from 3 to 10, from 3 to 8, from 4 to 7, or from 5 to 6 ring atoms. Heterocyclo groups are bonded to the rest of the molecule through the non-aromatic ring. In certain embodiments, the heterocyclo is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclo may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein. Non-limiting examples of moieties with which the heterocyclic group can be substituted are halogen (fluoro, chloro, bromo or iodo), hydroxyl, carbonyl, alkoxycarbonyl, alkoxycarbonylalkyl, sulfanyl, amino, alkylamino, arylamino, alkoxy, aryloxy, nitro, cyano, sulfonic acid, sulfate, phosphonic acid, phosphate, and phosphonate, either unprotected, or protected as necessary.

The term "heteroaryl" refers to refers to a monovalent monocyclic aromatic group and/or multicyclic aromatic group that contain at least one aromatic ring, wherein at least one aromatic ring contains one or more heteroatoms independently selected from O, S, and N in the ring. Heteroaryl groups are bonded to the rest of the molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein.

The term "alkylaryl" refers to an aryl group with an alkyl substituent. The term "aralkyl" or "arylalkyl" refers to an alkyl group with an aryl substituent.

The term "alkylheterocyclo" refers to a heterocyclo group with an alkyl substituent. The term "heterocycloalkyl" refers to an alkyl group with a heterocyclo substituent.

The term "alkylheteroaryl" refers to a heteroaryl group with an alkyl substituent. The term "heteroarylalkyl" refers to an alkyl group with a heteroaryl substituent.

As used herein, the term "hydantoinyl" refers to the group

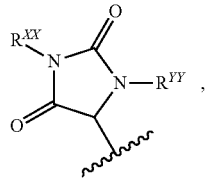

where $R^{XX}$ and $R^{YY}$ are each independently hydrogen or lower alkyl.

As used herein, the term "hydantoinylalkyl" refers to the group -alkyl-hydantoinyl, where alkyl and hydantoinyl are as described herein.

The term "protecting group" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) base addition salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example only and without limitation, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

As used herein, the term "nucleobase" refers to the base portion of a nucleoside or nucleotide. In certain embodiments, a nucleobase is a purine or pyrimidine base, as defined herein.

The term "purine" or "pyrimidine" base refers to, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-alkylaminopurine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-iodopyrimidine, $C^6$-iodo-pyrimidine, $C^5$—Br-vinyl pyrimidine, $C^6$—Br-vinyl pyrimidine, $C^5$-nitropyrimidine, $C^5$-amino-pyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, pyrrolotriazine, and pyrazolopyrimidinyl. Purine bases include, but are not limited to, guanine, adenine, hypoxanthine, 7-deazaguanine, 7-fluoro-7-deazaguanine, 7-deazaadenine, 7-fluoro-7-deazaadenine, 2,6-diaminopurine, 2-amino-6-chloropurine, 6-ethoxypurine, 6-methoxypurine and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "acyl" or "O-linked ester" refers to a group of the formula C(O)R', wherein R' is alkyl or cycloalkyl (including lower alkyl), carboxylate reside of amino acid, aryl including phenyl, alkaryl, arylalkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or arylalkyl sulphonyl including methanesulfonyl, the mono, di or triphosphate ester, trityl or monomethoxytrityl, substituted benzyl, alkaryl, arylalkyl including benzyl, alkoxyalkyl including methoxymethyl, aryloxyalkyl such as phenoxymethyl. Aryl groups in the esters optimally comprise a phenyl group. In particular, acyl groups include acetyl, trifluoroacetyl, methylacetyl, cyclpropylacetyl, propionyl, butyryl, hexanoyl, heptanoyl, octanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2, 2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoro-heptanoyl, 7H-dodecafluoro-heptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl.

The term "amino acid" refers to naturally occurring and synthetic α, β, γ, or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. In certain embodiments, the amino acid is in the D-configuration. In certain embodiments, the amino acid is provided as a substituent of a compound described herein, wherein the amino acid is a residue of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl, or β-histidinyl.

The term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —NR$^X$-G(S$_C$)—C(O)-Q$^1$, wherein Q$^1$ is —SR$^Y$, —NR$^Y$R$^Y$ or alkoxyl, R$^Y$ is hydrogen or alkyl, S$_C$ is a side chain of a naturally occurring or non-naturally occurring amino acid, G is C$_1$-C$_2$ alkyl, and R$^X$ is hydrogen or R$^X$ and S$_C$, together with the atoms to which they are attached, combine to form a five-membered heterocyclic ring. In an embodiment, an amino acid derivative is provided as a substituent of a compound described herein, wherein the substituent is —O—C(O)-G(S$_C$)—NH-Q$^2$, wherein Q$^2$ is hydrogen or alkoxyl, S$_C$ is a side chain of a naturally occurring or non-naturally occurring amino acid and G is C$_1$-C$_2$ alkyl. In certain embodiments, Q$^2$ and S$_C$, together with the atoms to which they are attached, combine to form a five-membered heterocyclic ring. In certain embodiments, G is C$_1$ alkyl and S$_C$ is hydrogen, alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl, or hydroxylarylalkyl. In an embodiment, an amino acid derivative is provided as a substituent of a compound described herein, wherein the amino acid derivative is in the D-configuration. In an embodiment, an amino acid derivative is provided as a substituent of a compound described herein, wherein the amino acid derivative is in the L-configuration.

As used herein, the term "aminoalkyl" refers to an alkyl group with an amino substituent, where alkyl and amino are as described herein.

As used herein, the term "carboxylalkyl" refers to the group -alkyl-C(O)OH, where alkyl is as described herein.

As used herein, the term "aminoiminoaminoalkyl" refers to the group -alkyl-amino-C(NH)-amino, where alkyl and amino are as described herein.

As used herein, the term "aminocarbonylalkyl" refers to the group -alkyl-C(O)-amino, where alkyl and amino are as described herein.

As used herein, the term "sulfanylalkyl" refers to the group -alkyl-SH, where alkyl is as described herein.

As used herein, the term "carbamoylalkyl" refers to the group -alkyl-C(O)-amino, where alkyl and amino are as described herein.

As used herein, the term "alkylsulfanylalkyl" refers to the group -alkyl-S-alkyl, where alkyl is as described herein.

As used herein, the term "hydroxylarylalkyl" refers to the group -alkyl-aryl-OH, where alkyl and aryl are as described herein.

As used herein when referring to a substituent on a sugar ring of a nucleoside, the term "alpha" refers to a substituent on the same side of the plane of the sugar ring as the 5' carbon and the term "beta" refers to a substituent on the opposite side of the plane of the sugar ring from the 5' carbon. As shown below, substituent "A" is in the "alpha" position, and substituent "B" is in the "beta" position with respect to the 5' carbon:

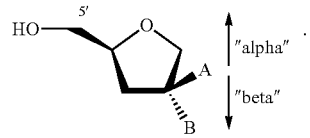

The term "substantially free of" or "substantially in the absence of" with respect to a nucleoside composition refers to a nucleoside composition that includes at least 85 or 90% by weight, in certain embodiments 95%, 98%, 99% or 100% by weight, of the designated enantiomer of that nucleoside. In certain embodiments of the methods and compounds provided herein, the compounds are substantially free of a non-designated enantiomer.

Similarly, the term "isolated" with respect to a nucleoside composition refers to a nucleoside composition that includes at least 85%, 90%, 95%, 98%, or 99% to 100% by weight, of the nucleoside, the remainder comprising other chemical species or enantiomers.

"Solvate" refers to a compound provided herein or a salt thereof, that further includes a stoichiometric or non-stoichiometric amount of solvent bound by non-covalent intermolecular forces. Where the solvent is water, the solvate is a hydrate.

"Isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

"Isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "cycloalkyl," "alkenyl," "cycloalkenyl," "alkynyl," "aryl," "alkoxy," "alkoxycarbonyl," "alkoxycarbonylalkyl," "amino," "carboxyl," "alkylamino," "arylamino," "thioalkyoxy," "heterocyclo," "heteroaryl," "alkylheterocyclo," "alkylheteroaryl," "acyl," "aralkyl," "alkaryl," "purine," "pyrimidine," "carboxyl," and "amino acid" groups optionally comprise deuterium at one or more positions where hydrogen atoms are present, and wherein the deuterium composition of the atom or atoms is other than the natural isotopic composition.

Also as used herein, "alkyl," "cyclo alkyl," "alkenyl," "cycloalkenyl," "alkynyl," "aryl," "alkoxy," "alkoxycarbonyl," "alkoxycarbonylalkyl," "carboxyl," "alkylamino," "arylamino," "thioalkyoxy," "heterocyclo," "heteroaryl," "alkylheterocyclo," "alkylheteroaryl," "acyl," "aralkyl," "alkaryl," "purine," "pyrimidine," "carboxyl," and "amino acid" groups optionally comprise carbon-13 at an amount other than the natural isotopic composition.

As used herein, $EC_{50}$ refers to a dosage, concentration, or amount of a particular test compound that elicits a dose-dependent response at 50% of maximal expression of a particular response that is induced, provoked, or potentiated by the particular test compound.

As used herein, the $IC_{50}$ refers to an amount, concentration, or dosage of a particular test compound that achieves a 50% inhibition of a maximal response in an assay that measures such response.

The term "host," as used herein, refers to any unicellular or multicellular organism in which the virus can replicate, including cell lines and animals, and in certain embodiments, a human. Alternatively, the host can be carrying a part of the Flaviviridae viral genome, whose replication or function can be altered by the compounds of the present invention. The term host specifically includes infected cells, cells transfected with all or part of the Flaviviridae genome and animals, in particular, primates (including chimpanzees) and humans. In most animal applications of the present invention, the host is a human patient. Veterinary applications, in certain indications, however, are clearly anticipated by the present invention (such as chimpanzees).

As used herein, the terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and for example, a human. In certain embodiments, the subject is refractory or non-responsive to current treatments for hepatitis C infection. In another embodiment, the subject is a farm animal (e.g., a horse, a cow, a pig, etc.) or a pet (e.g., a dog or a cat). In certain embodiments, the subject is a human.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In certain embodiments, a therapeutic agent is an agent which is known to be useful for, or has been or is currently being used for the treatment or prevention of a disorder or one or more symptoms thereof.

"Therapeutically effective amount" refers to an amount of a compound or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" includes a compound provided herein. In certain other embodiments, the term "prophylactic agent" does not refer a compound provided herein. For example, a prophylactic agent is an agent which is known to be useful for, or has been or is currently being used to prevent or impede the onset, development, progression, and/or severity of a disorder.

As used herein, the phrase "prophylactically effective amount" refers to the amount of a therapy (e.g., prophylactic agent) which is sufficient to result in the prevention or reduction of the development, recurrence or onset of one or more symptoms associated with a disorder (or to enhance or improve the prophylactic effect(s) of another therapy (e.g., another prophylactic agent).

Compounds

Provided herein are thiophosphate nucleoside compounds useful for the treatment of Flaviviridae infections such as HCV infection. The thiophosphate nucleoside compounds can be formed as described herein and used for the treatment of Flaviviridae infections such as HCV infection.

In certain embodiments, provided herein are compounds according to Formula 2001:

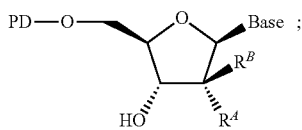

(2001)

or a pharmaceutically acceptable salt, solvate, stereoisomeric form, tautomeric form, or polymorphic form thereof, wherein:
Base is a nucleobase;
$R^A$ is hydroxyl or halo;
$R^B$ is methyl or halo;
PD is

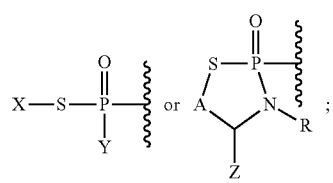

X is alkyl, alkoxycarbonylalkyl, (alkoxycarbonyl)(alkoxycarbonylamino)alkyl, cycloalkyl, heterocycloalkyl, hydantoinylalkyl, or aryl;
Y is —$NR^1R^2$ or an N-linked or O-linked amino acid residue, or a derivative thereof;
Z is alkyl, alkoxycarbonyl, or alkoxyalkylcarbonyl;
A is —$CHR^{10}$—, —$CHR^{10}CHR^{11}$—, or —$CHR^{10}CHR^{11}CHR^{12}$—;
$R^1$ is hydrogen, alkyl, cycloalkyl, aryl, heteroaryl, arylalkyl, or heteroarylalkyl;
$R^2$ is hydrogen or alkyl;
R is hydrogen or alkyl; and
each of $R^{10}$, $R^{11}$, and $R^{12}$ is independently hydrogen or alkyl; or $R^{10}$ and $R^{11}$, together with the carbon atoms to which they are attached, combine to form a five-, six-, or seven-membered ring.

In certain embodiments, provided herein are compounds according to Formula (I):

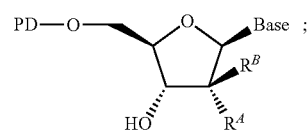

(I)

or a pharmaceutically acceptable salt, solvate, stereoisomeric form, tautomeric form, or polymorphic form thereof, wherein: Base is a nucleobase; $R^A$ is hydroxyl or halo; $R^B$ is methyl or halo; PD is

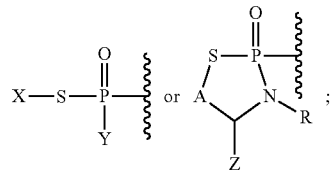

X is alkyl, alkoxycarbonylalkyl, (alkoxycarbonyl)(alkoxycarbonylamino)alkyl, cycloalkyl, heterocycloalkyl, hydantoinylalkyl, or aryl; Y is —$NR^1R^2$ or an N-linked amino acid, or ester thereof; Z is alkyl, alkoxycarbonyl or alkoxyalkylcarbonyl; A is —$CHR^{10}$—, —$CHR^{10}CHR^{11}$—, or —$CHR^{10}CHR^{11}CHR^{12}$—; $R^1$ is hydrogen, alkyl, cycloalkyl, aryl, heteroaryl, arylalkyl, or heteroarylalkyl; $R^2$ is hydrogen or alkyl; R is hydrogen or alkyl; and each of $R^{10}$, $R^{11}$, and $R^{12}$ is independently hydrogen or alkyl; or $R^{10}$ and $R^{11}$, together with the carbon atoms to which they are attached, combine to form a five-, six-, or seven-membered ring.

In certain embodiments, provided herein are compounds according to Formula III:

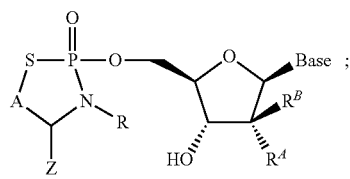

(III)

or a pharmaceutically acceptable salt, solvate, stereoisomeric form, tautomeric form, or polymorphic form thereof; where Base, A, Z, $R^A$, $R^B$ and R are as described in the context of Formula I or Formula 2001.

In certain embodiments, provided herein are compounds according to Formula II:

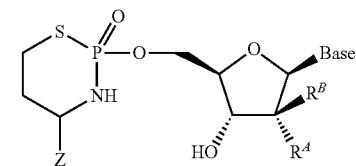

(II)

or a pharmaceutically acceptable salt, solvate, stereoisomeric form, tautomeric form, or polymorphic form thereof; where Base, X, Y, $R^A$ and $R^B$ are as described in the context of Formula I or Formula 2001.

In certain embodiments, provided herein are compounds according to any of Formulas IV-VI:

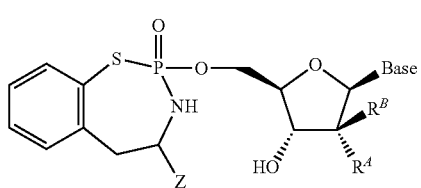

(IV)

(V)

-continued

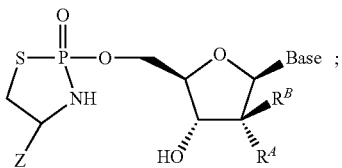
(VI)

or a pharmaceutically acceptable salt, solvate, stereoisomeric form, tautomeric form, or polymorphic form thereof; where Base, Z, $R^A$ and $R^B$ are as described in the context of Formula I. In an embodiment, a compound of any of Formulas 2001, I, III, or IV-VI is provided wherein Z is alkyl. In an embodiment, a compound of any of Formulas 2001, I, III, or IV-VI is provided wherein Z is alkoxycarbonyl. In an embodiment, a compound of any of Formulas 2001, I, III, or IV-VI is provided wherein Z is alkoxyalkylcarbonyl.

In certain embodiments, provided herein are compounds according to Formula XXIX:

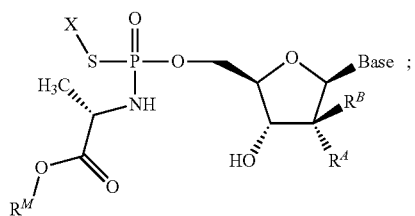
(XXIX)

or a pharmaceutically acceptable salt, solvate, stereoisomeric form, tautomeric form, or polymorphic form thereof; wherein $R^M$ is alkyl; and where Base, X, $R^A$ and $R^B$ are as described in the context of Formula I or Formula 2001. In an embodiment, a compound of Formula XXIX is provided wherein $R^M$ is lower alkyl. In an embodiment, a compound of Formula XXIX is provided wherein $R^M$ is $C_1$-$C_3$ alkyl.

In certain embodiments, provided herein are compounds according to Formula VII or VIII:

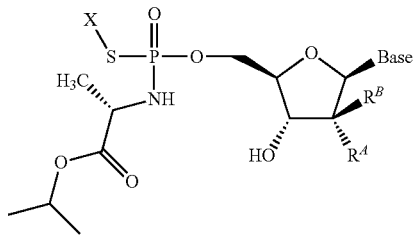
(VII)

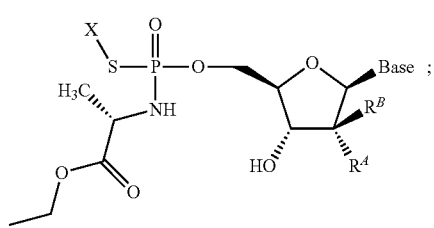
(VIII)

or a pharmaceutically acceptable salt, solvate, stereoisomeric form, tautomeric form, or polymorphic form thereof; where Base, X, $R^A$ and $R^B$ are as described in the context of Formula I or Formula 2001.

In certain embodiments, provided herein are compounds according to any of Formulas (IX)-(XII):

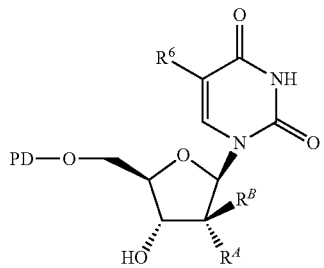
(IX)

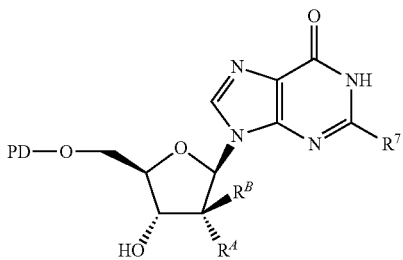
(X)

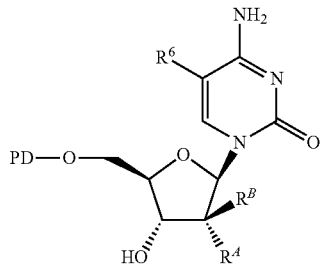
(XI)

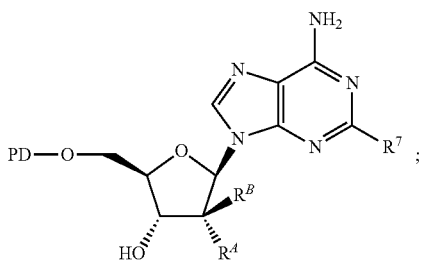
(XII)

or a pharmaceutically acceptable salt, solvate, stereoisomeric form, tautomeric form, or polymorphic form thereof; wherein each $R^6$ is independently hydrogen, halogen, or alkyl; and each $R^7$ is independently hydrogen or —$NH_2$; and where PD, $R^A$, and $R^B$ are as described in the context of Formula I. In an embodiment, each $R^7$ is independently hydrogen or amino.

In certain embodiments, provided herein are compounds according to any of Formulas XIII-XVII:

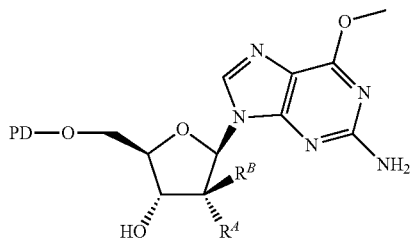
(XIII)

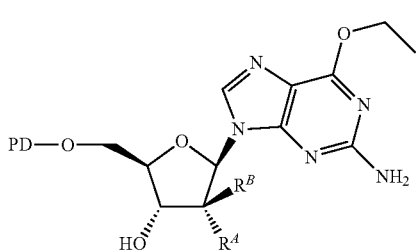
(XIV)

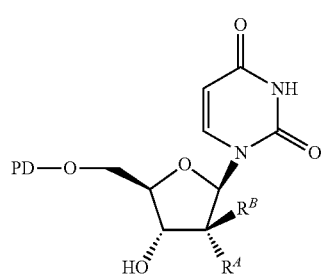
(XV)

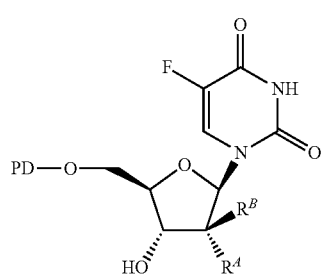
(XVI)

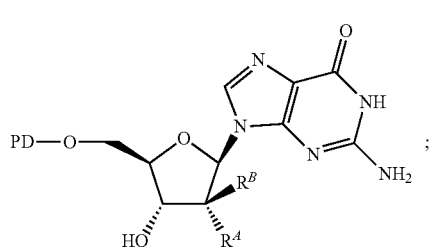
(XVII)

or a pharmaceutically acceptable salt, solvate, stereoisomeric form, tautomeric form, or polymorphic form thereof; where PD, $R^A$, and $R^B$ are as described in the context of Formula I or Formula 2001.

In certain embodiments, provided herein are compounds according to any of Formulas XVIII or XIX:

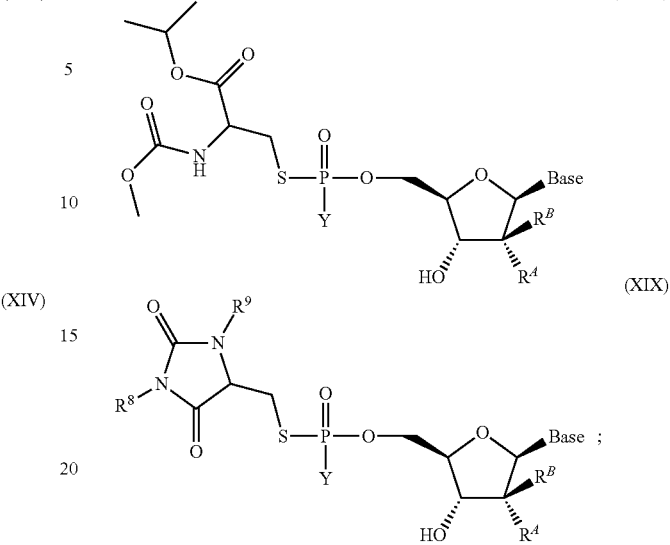
(XVIII)

(XIX)

or a pharmaceutically acceptable salt, solvate, stereoisomeric form, tautomeric form, or polymorphic form thereof; wherein each of $R^8$ and $R^9$ are independently hydrogen or lower alkyl; and where Base, Y, $R^A$, and $R^B$ are as described in the context of Formula I or Formula 2001.

In certain embodiments, provided herein are compounds according to Formula XXVII:

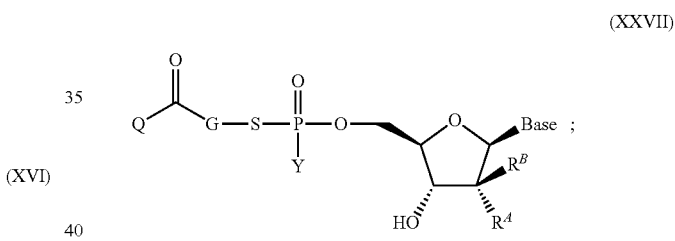
(XXVII)

or a pharmaceutically acceptable salt, solvate, stereoisomeric form, tautomeric form, or polymorphic form thereof; wherein Q is —$SR^{20}$; —$NR^{21}R^{22}$ or —$OR^{20}$; each of $R^{20}$, $R^{21}$ and $R^{22}$ is independently hydrogen or alkyl; and G is $C_1$-$C_2$ alkyl; and where Base, Y, $R^A$, and $R^B$ are as described in the context of Formula I or Formula 2001. In an embodiment, a compound of Formula XXVII is provided wherein G is $C_2$ alkyl. In an embodiment, a compound of Formula XXVII is provided wherein G is substituted with —NHC(O)Q. In an embodiment, a compound of Formula XXVII is provided wherein G is —$CH_2CH(NHC(O)Q)$-.

In certain embodiments, provided herein are compounds according to Formula) XXVIII:

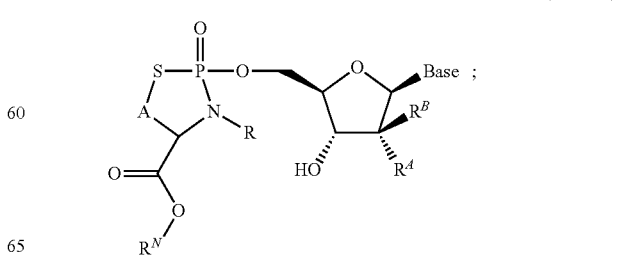
(XXVIII)

or a pharmaceutically acceptable salt, solvate, stereoisomeric form, tautomeric form, or polymorphic form thereof; wherein $R^N$ is cycloalkyl or aralkyl; and where Base, A, R, $R^A$, and $R^B$ are as described in the context of Formula I or Formula 2001.

In certain embodiments, provided herein are compounds according to any of Formulas 2001, I-XXII, XXVII or XXVIII wherein $R^A$ is hydroxyl and $R^B$ is lower alkyl. In certain embodiments, provided herein are compounds according to any of Formulas 2001, I-XXII, XXVII or XXVIII, wherein $R^A$ is halo and $R^B$ is lower alkyl. In certain embodiments, provided herein are compounds according to any of Formulas 2001, I-XXII, XXVII or XXVIII, wherein $R^A$ is fluoro and $R^B$ is lower alkyl. In certain embodiments, provided herein are compounds according to any of Formulas 2001, I-XXII, XXVII or XXVIII, wherein $R^A$ is chloro and $R^B$ is lower alkyl.

In certain embodiments, provided herein are compounds according to any of Formulas XX-XXII:

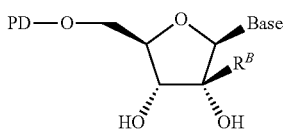

(XX)

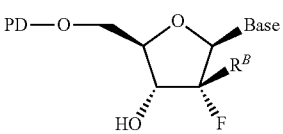

(XXI)

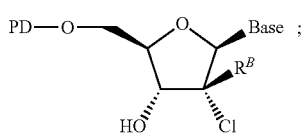

(XXII)

or a pharmaceutically acceptable salt, solvate, stereoisomeric form, tautomeric form, or polymorphic form thereof; where Base, PD, and $R^B$ are as described in the context of Formula I or Formula 2001.

In certain embodiments, provided herein are compounds according to any of Formulas XXIII-XXV:

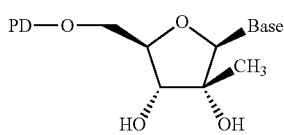

(XXIII)

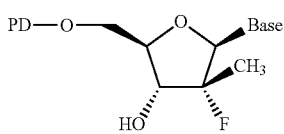

(XXIV)

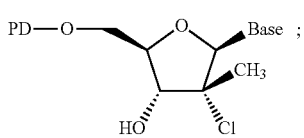

(XXV)

or a pharmaceutically acceptable salt, solvate, stereoisomeric form, tautomeric form, or polymorphic form thereof; where Base and PD are as described in the context of Formula I or Formula 2001.

In certain embodiments, provided herein are compounds according to Formula XXVI:

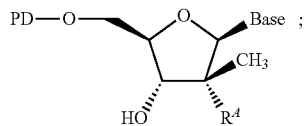

(XXVI)

or a pharmaceutically acceptable salt, solvate, stereoisomeric form, tautomeric form, or polymorphic form thereof; where Base, $R^A$ and PD are as described in the context of Formula I or Formula 2001.

In certain embodiments provided herein are compounds according to any of Formulas I, IX-XVII and XX-XXVI wherein each PD is independently

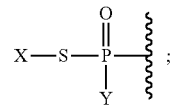

where X and Y are as described in the context of Formula I. In certain embodiments provided herein are compounds according to any of Formulas I, IX-XVII and XX-XXVI wherein each PD is independently

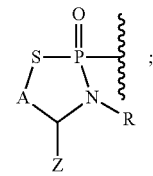

where Z, R and A are as described in the context of Formula I or Formula 2001.

In certain embodiments, provided herein are compounds according to any of Formulas I-VIII or XVIII-XXIX wherein each Base is independently:

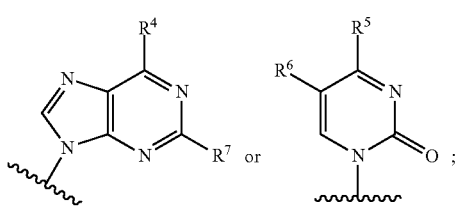

or tautomeric form thereof, wherein: each $R^4$ is independently hydrogen, hydroxyl, alkoxyl, amino or aminoalkyl;

each $R^5$ is independently hydrogen, hydroxyl, amino, or alkoxyl; each $R^6$ is independently hydrogen, halogen, or alkyl; and each $R^7$ is independently hydrogen or —$NH_2$. In an embodiment, each $R^7$ is independently hydrogen or amino.

In certain embodiments provided herein is a compound according to any of formulas 2001, I, II, VII-XVII, XX-XXVI or XXIX wherein: X is

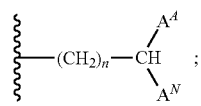

n is an integer selected over the range of 1-10; $A^A$ is —C(O)—O—$R^{100}$; $A^N$ is —NH—C(O)—O—$R^{101}$; and each of $R^{100}$ and $R^{101}$ is independently lower alkyl. In an embodiment, each of $R^{100}$ and $R^{101}$ is independently $C_1$-$C_5$ alkyl.

In certain embodiments provided herein are compounds according to any of Formulas 1-23byii:

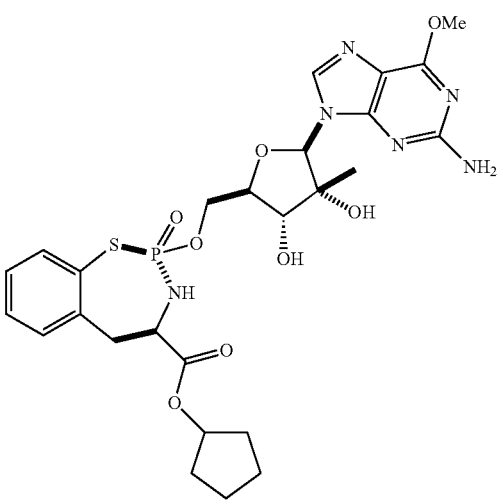

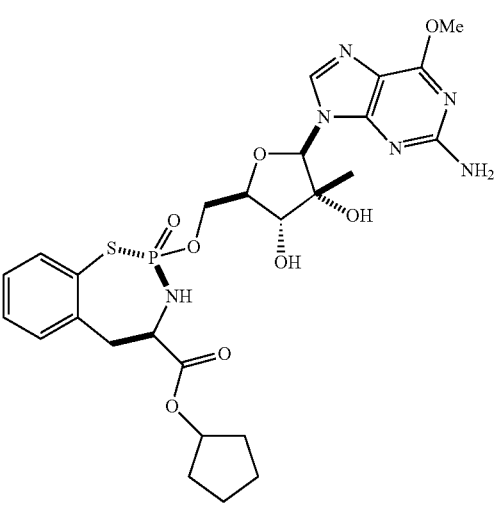

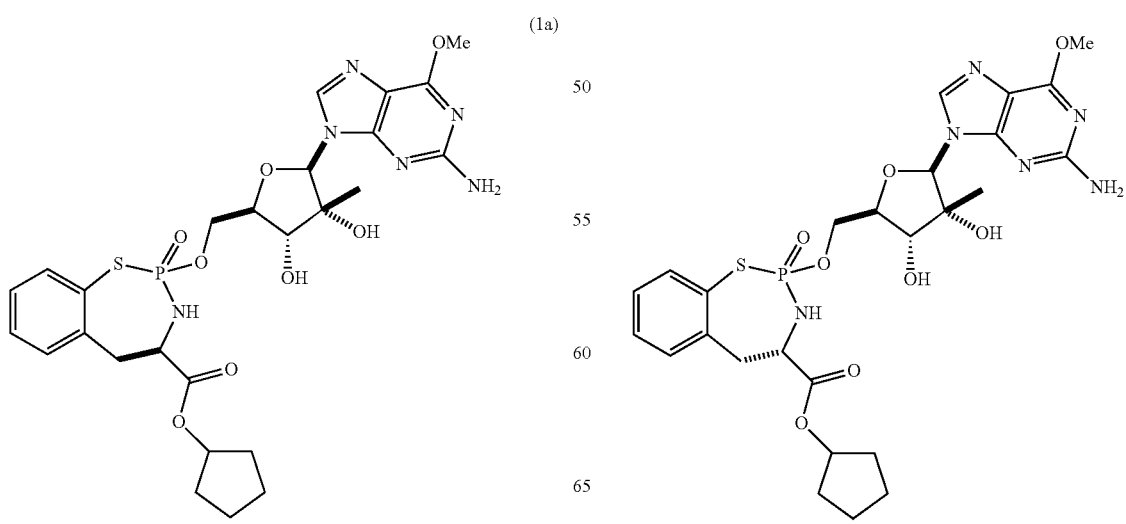

-continued
(1bi)
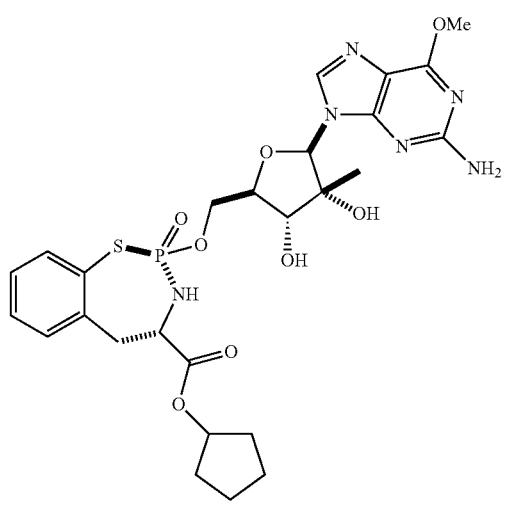
(2a)
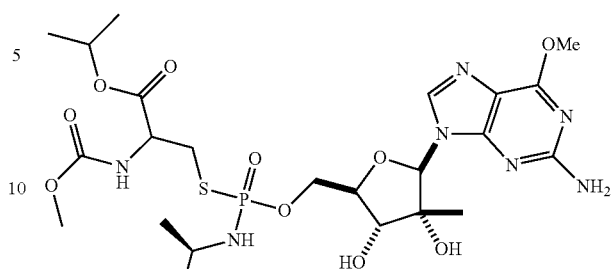
(2ai)
(1bii)
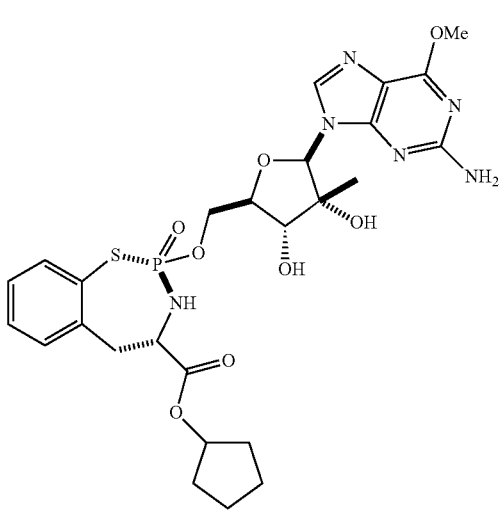
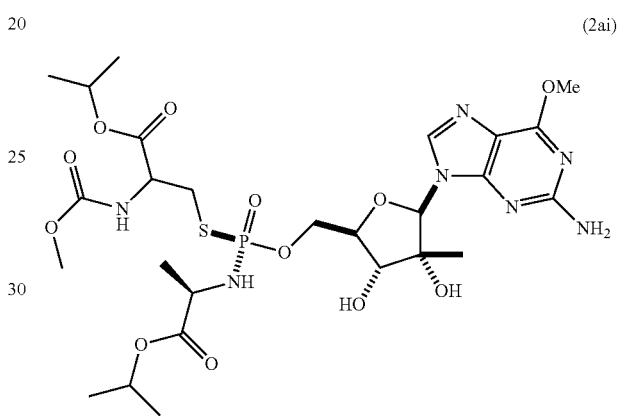
(2aii)
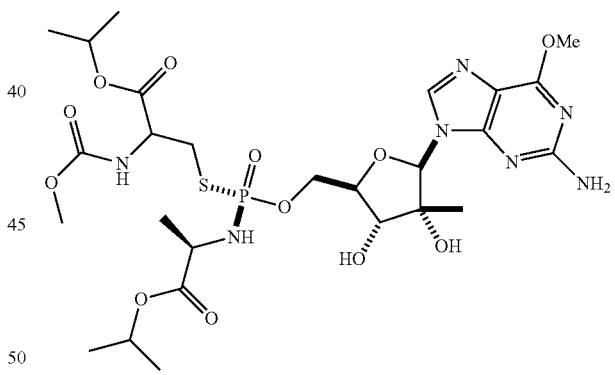
(2)
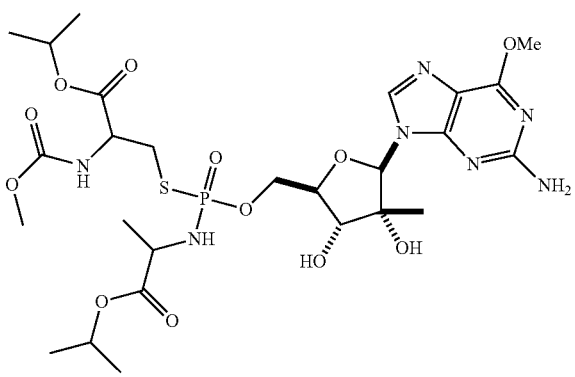
(2b)
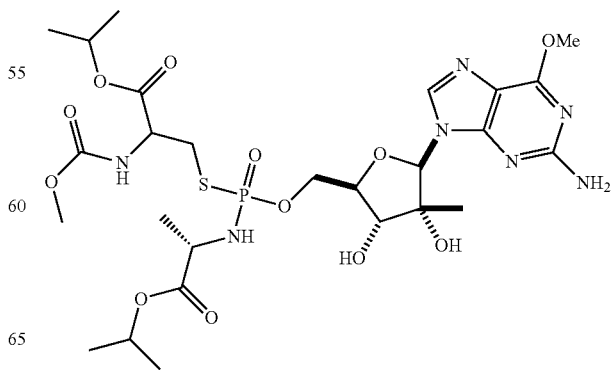

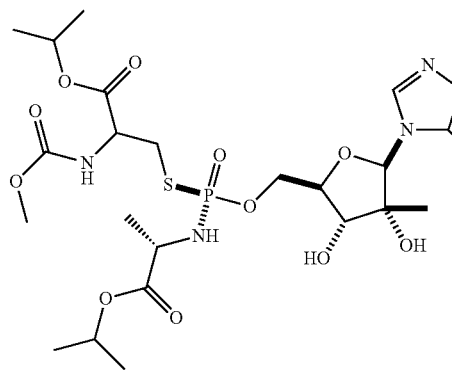
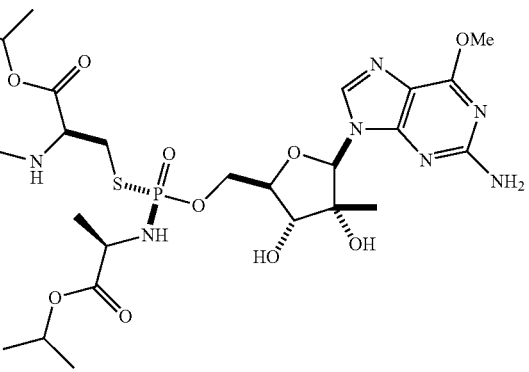

(2ay) 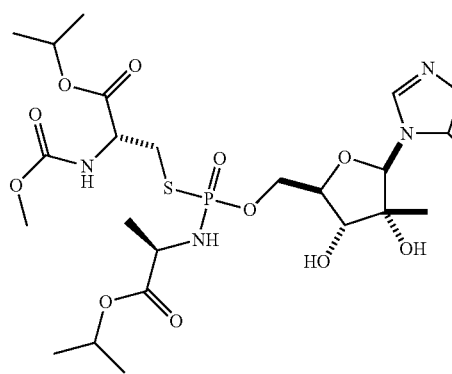
(2byi) 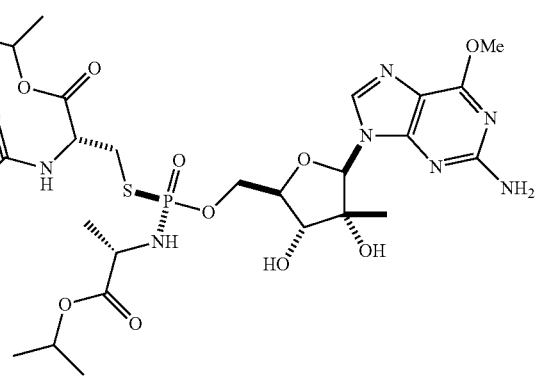
(2ayi) 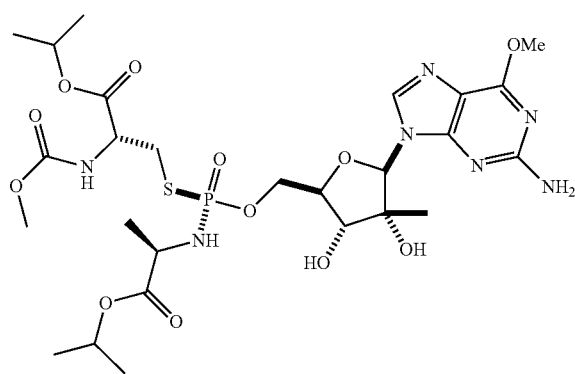
(2byii) 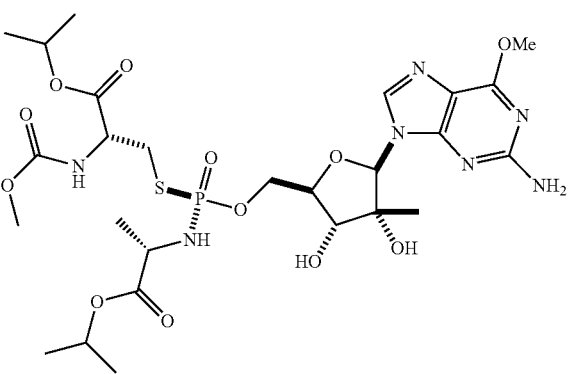
(2ayii) 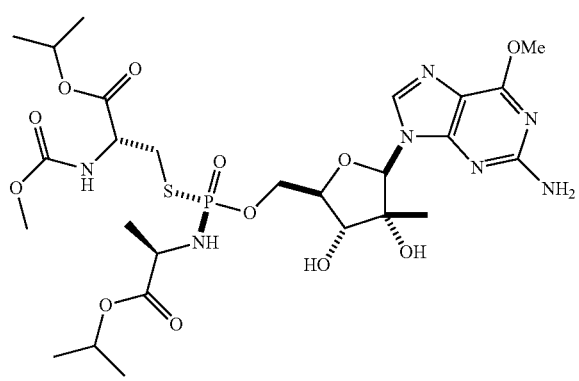
(3) 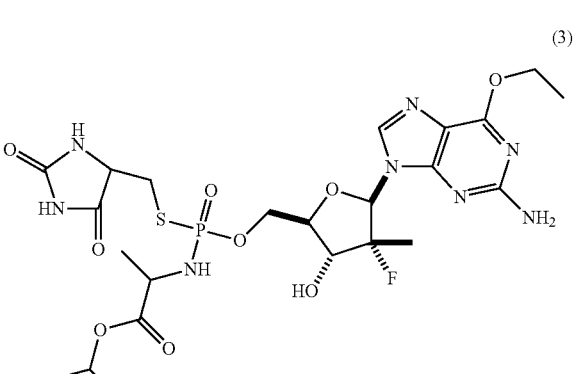
(2by) 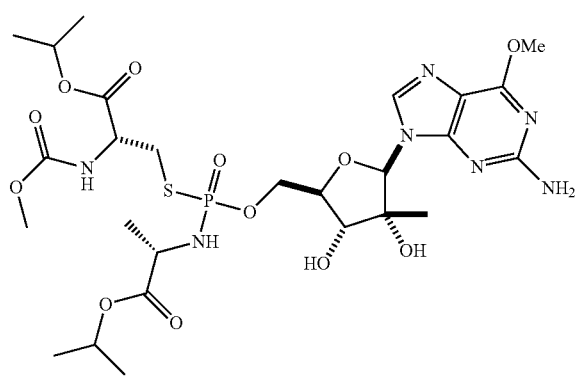
(3a) 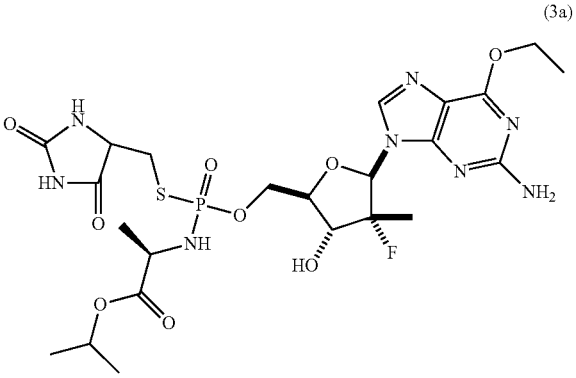

| 31 -continued | 32 -continued |
|---|---|
| (3ai) 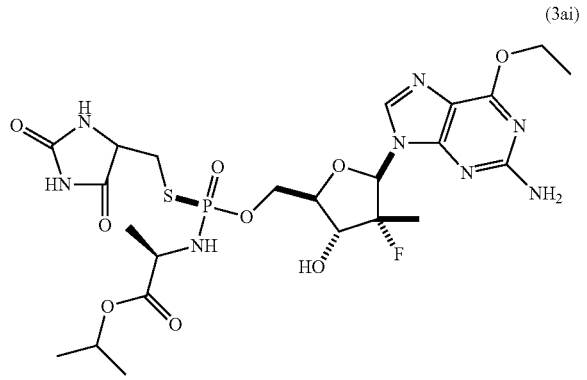 | (3bii) 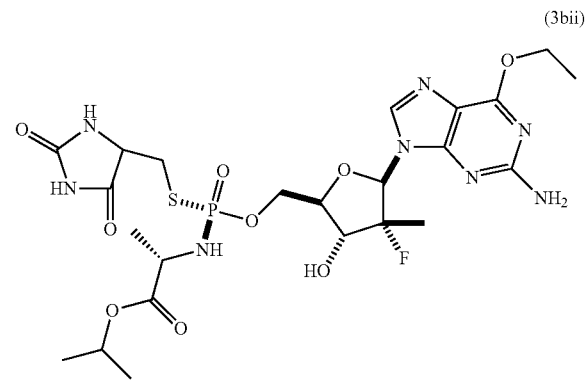 |
| (3aii) 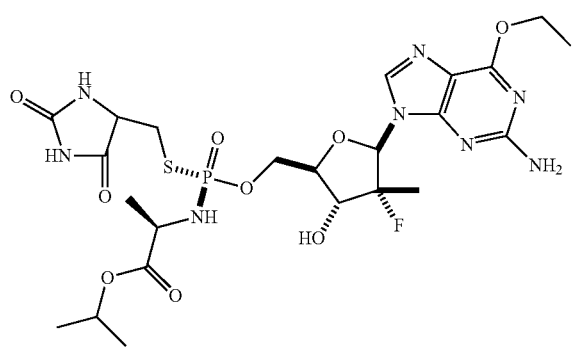 | (3ax) 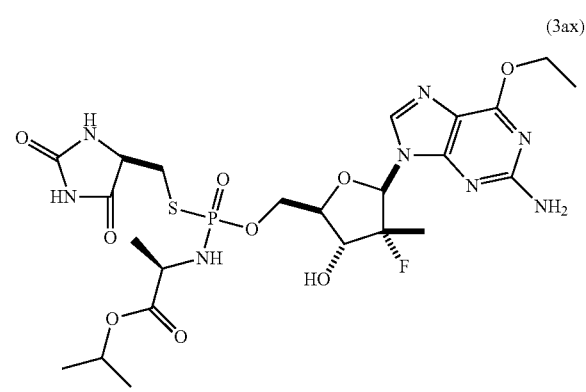 |
| (3b) 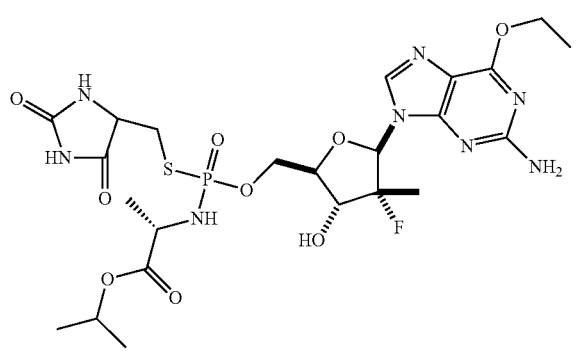 | (3axi) 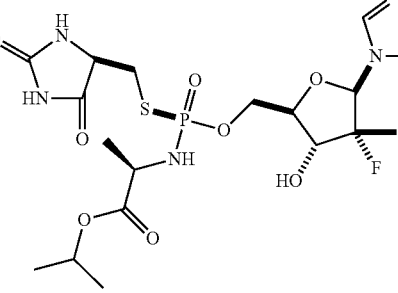 |
| (3bi) 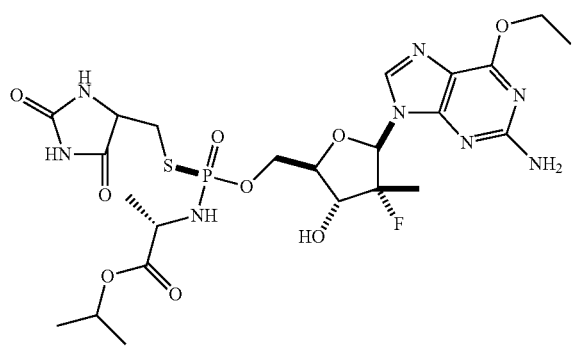 | (3axii) 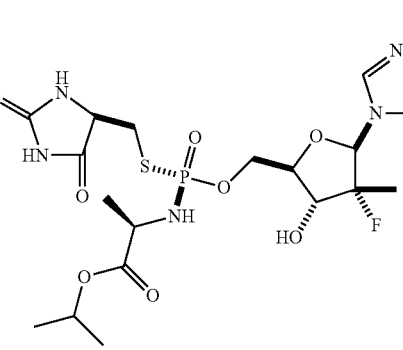 |

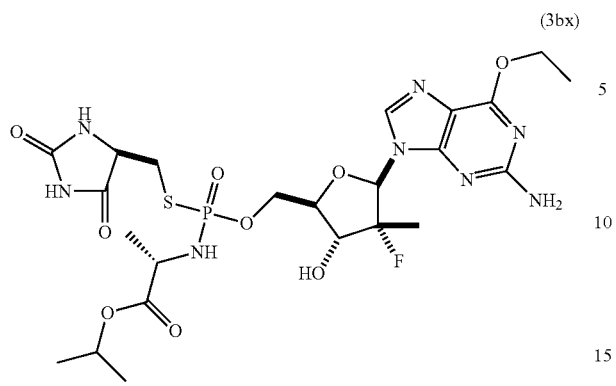
(3bx)
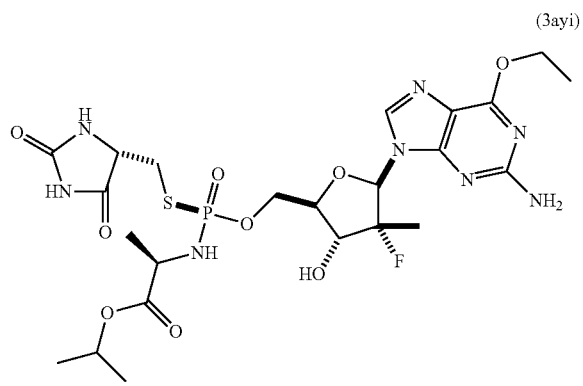
(3ayi)
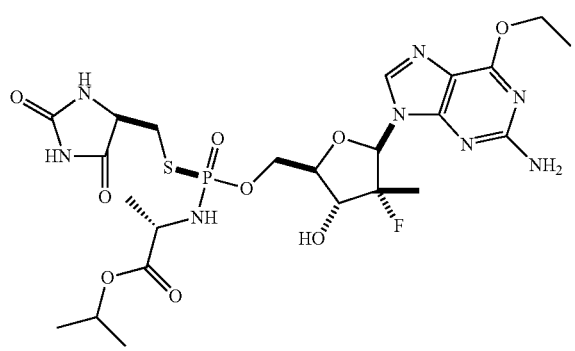
(3bxi)
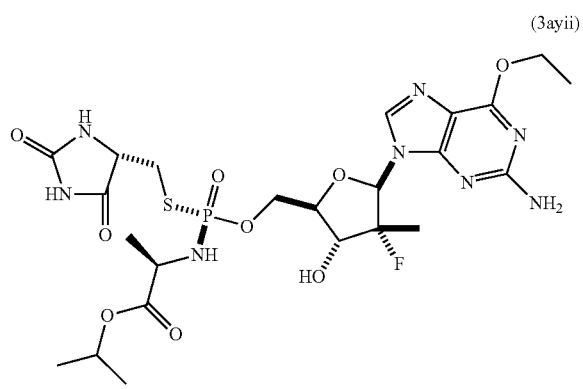
(3ayii)
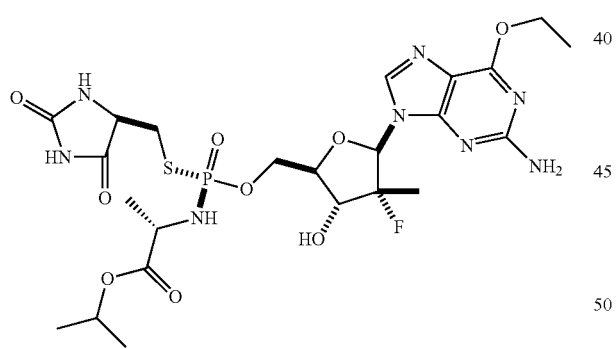
(3bxii)
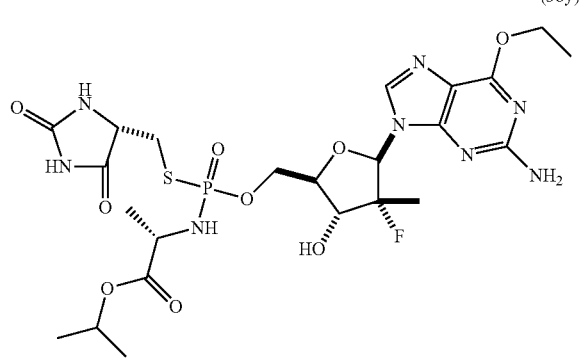
(3by)
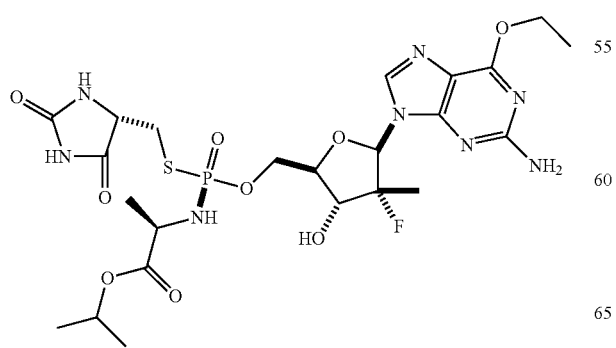
(3ay)
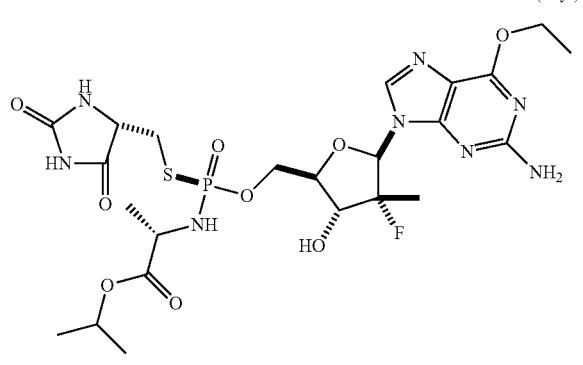
(3byi)

(3byii)
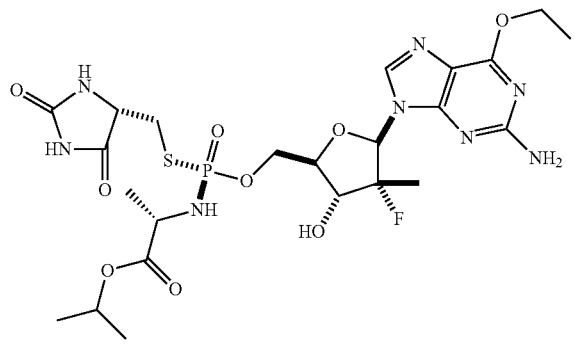
(4)
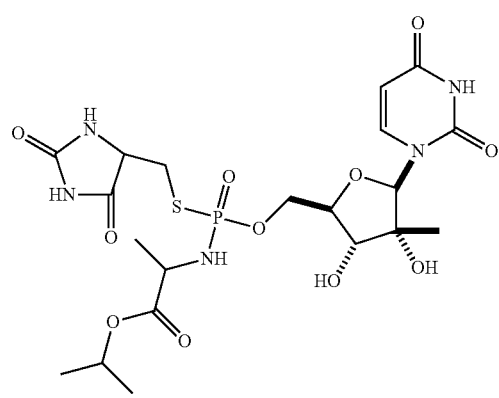
(4a)
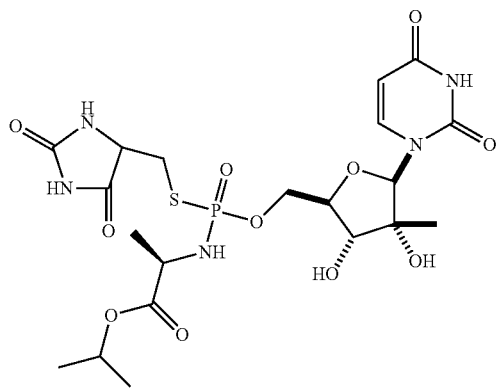
(4ai)
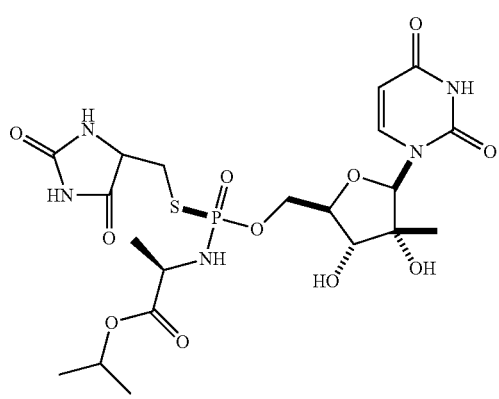
(4aii)
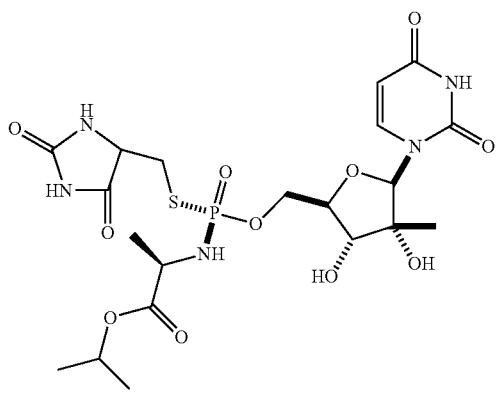
(4b)
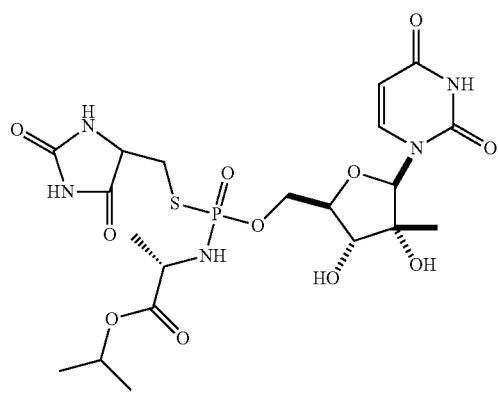
(4bi)
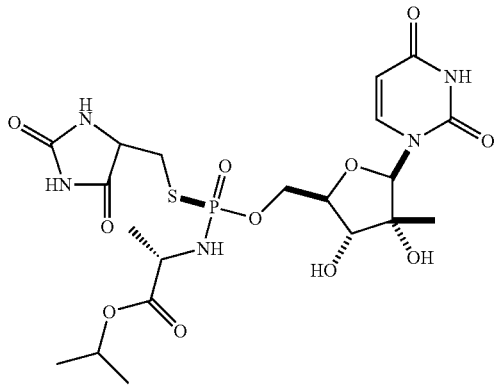
(4bii)
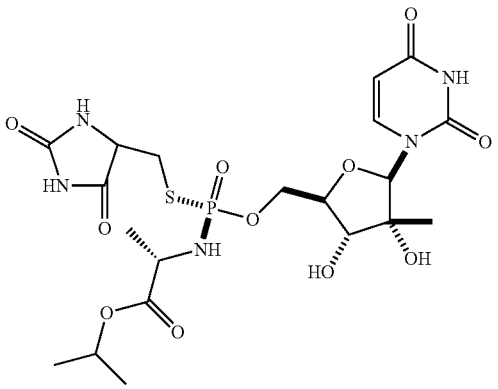

37
-continued
(4ax)
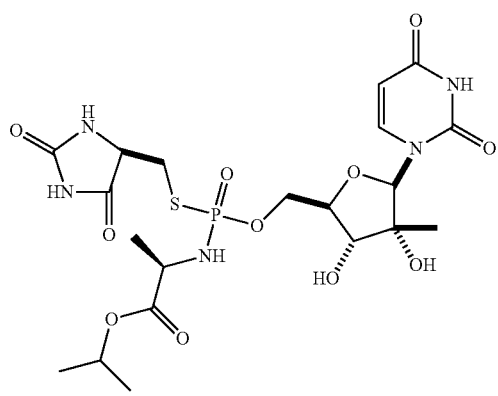
(4axi)
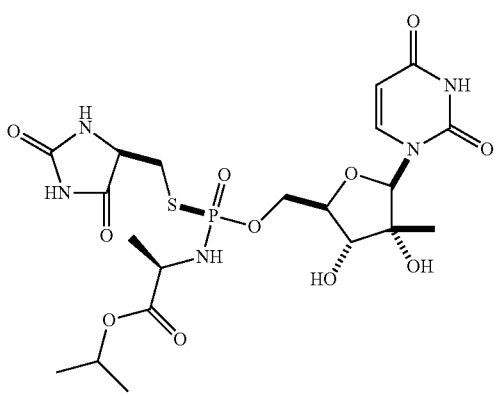
(4axii)
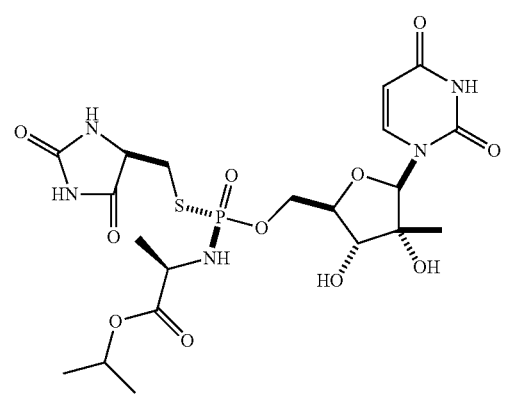
(4bx)
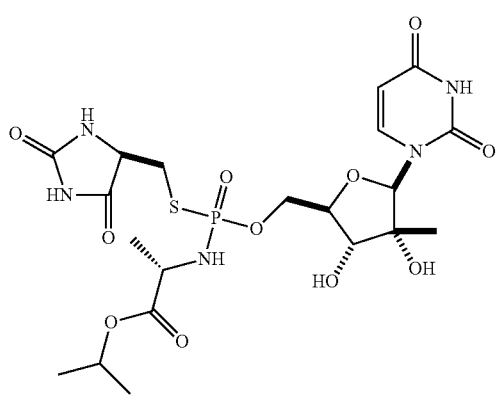
38
-continued
(4bxi)
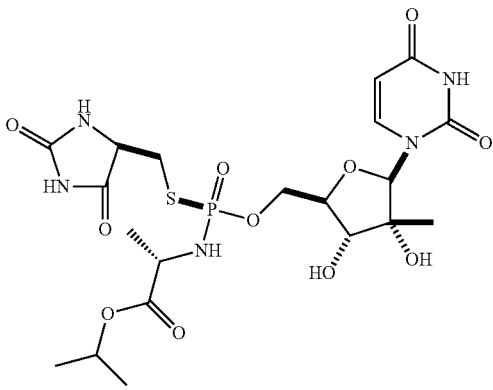
(4bxii)
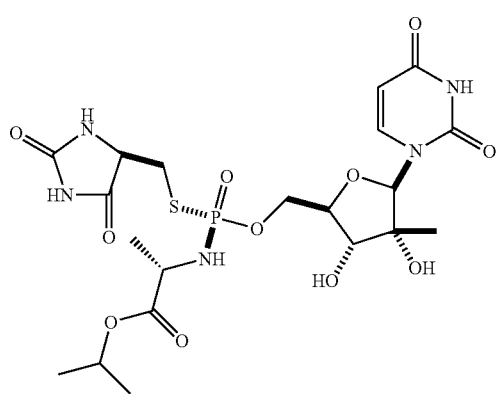
(4ay)
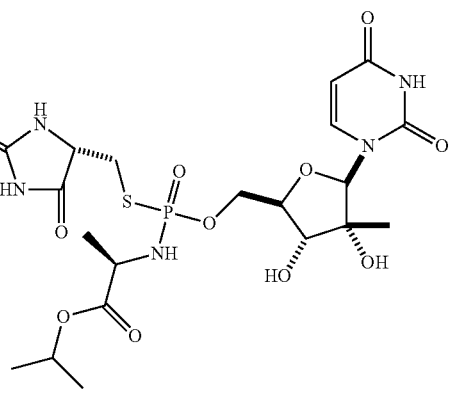
(4ayi)
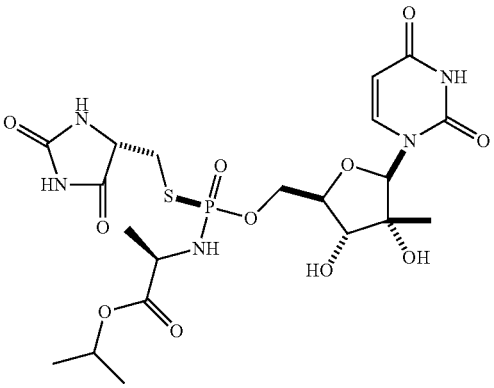

(4ayii)
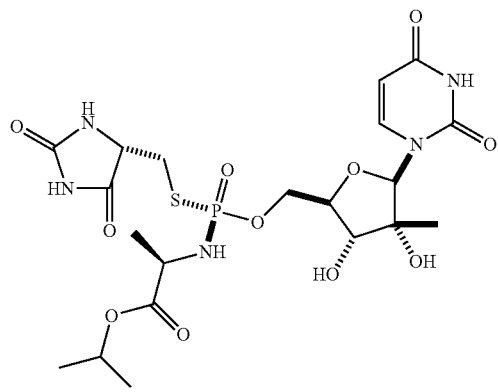
(4by)
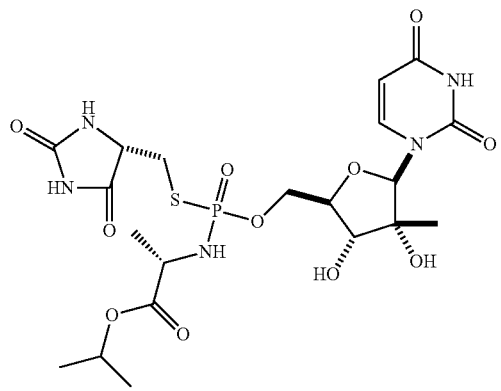
(4byi)
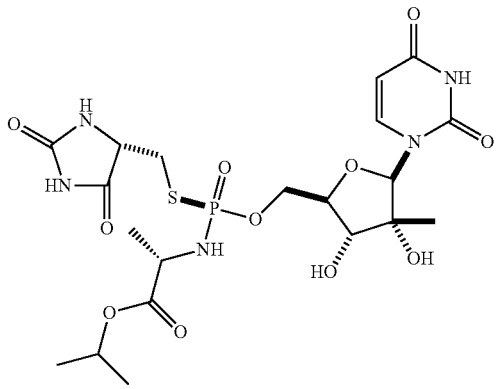
(4byii)
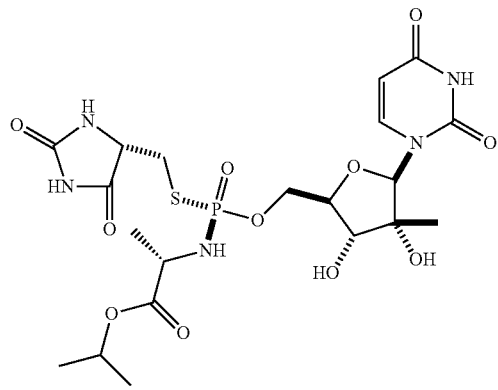
(5)
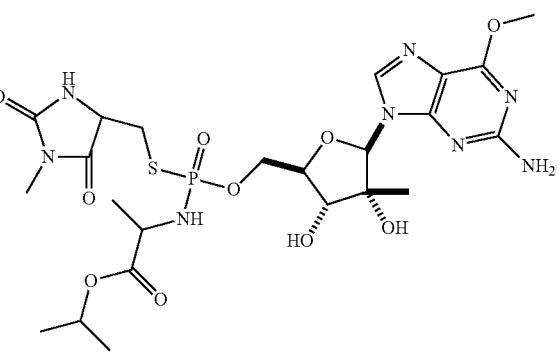
(5a)
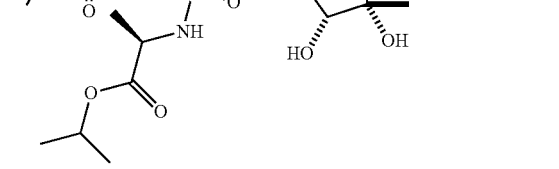
(5ai)
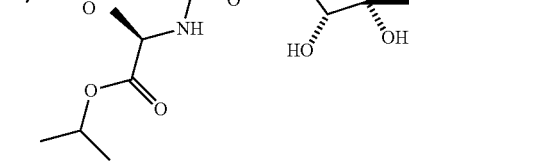
(5aii)
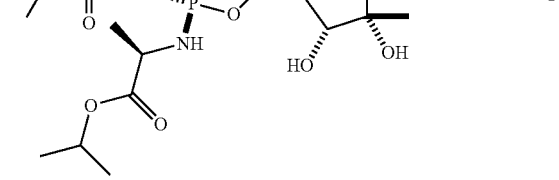

41
-continued
(5b)
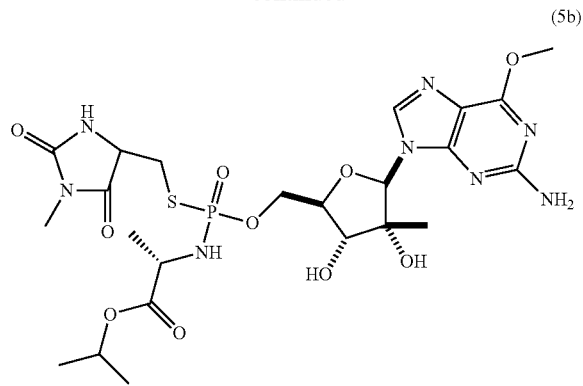
(5bi)
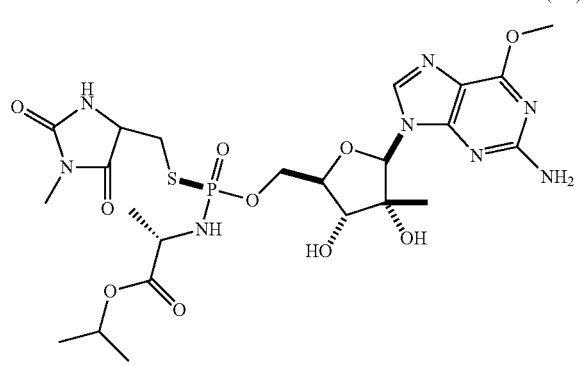
(5bii)
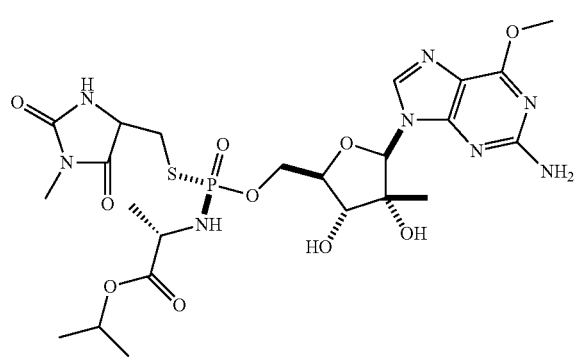
(5ax)
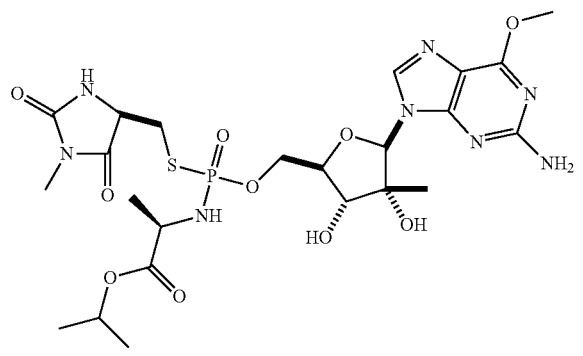
42
-continued
(5axi)
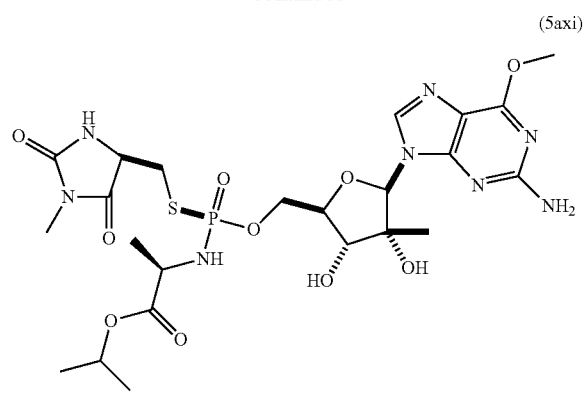
(5axii)
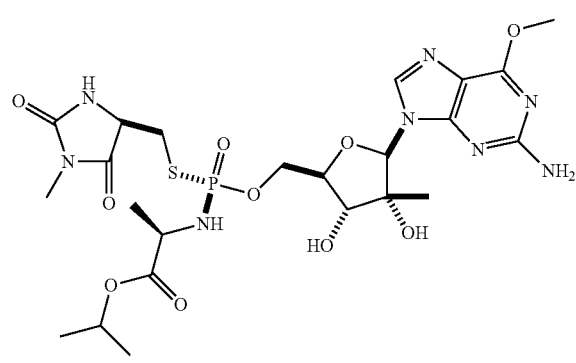
(5bx)
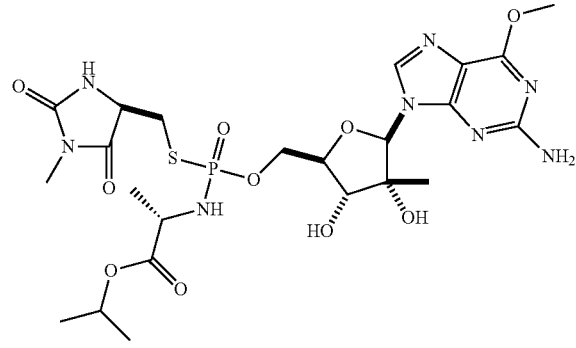
(5bxi)
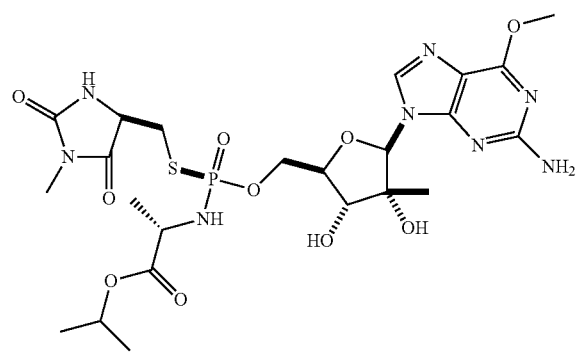

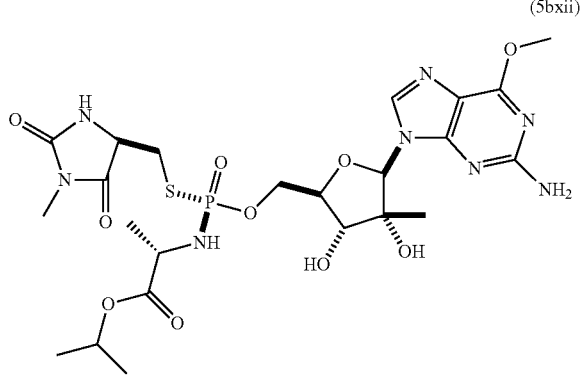
(5bxii)
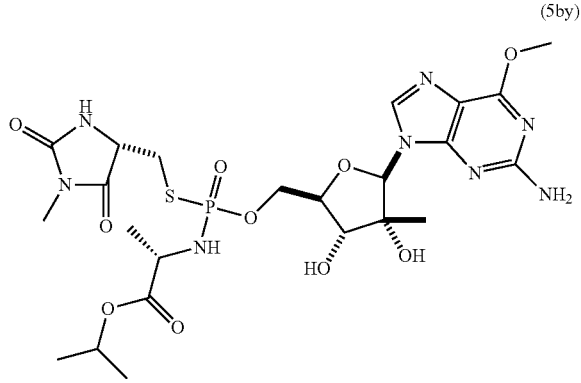
(5by)
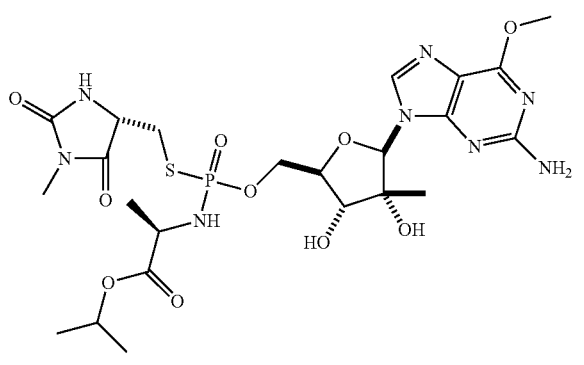
(5ay)
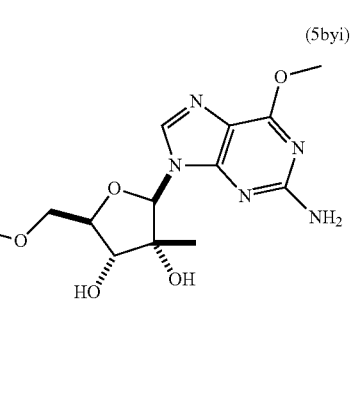
(5byi)
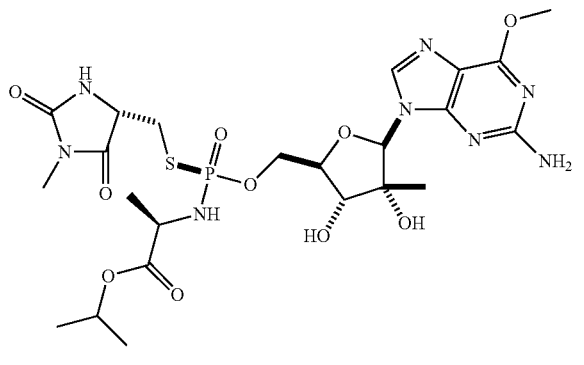
(5ayi)
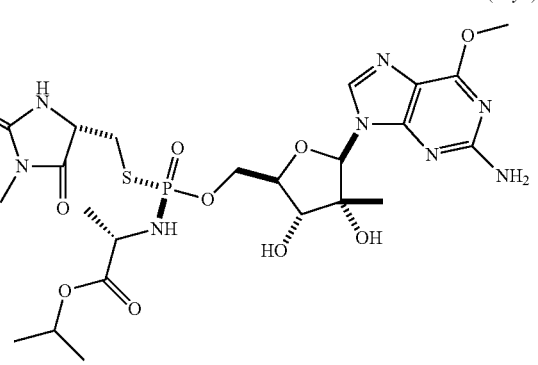
(5byii)
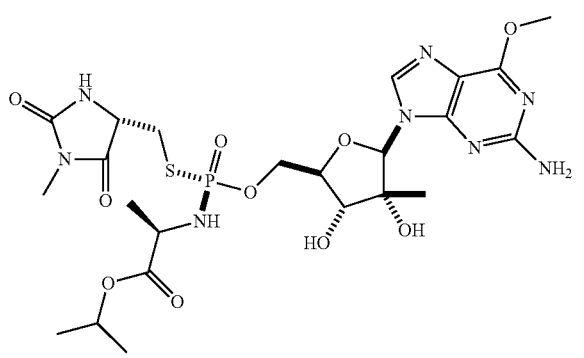
(5ayii)
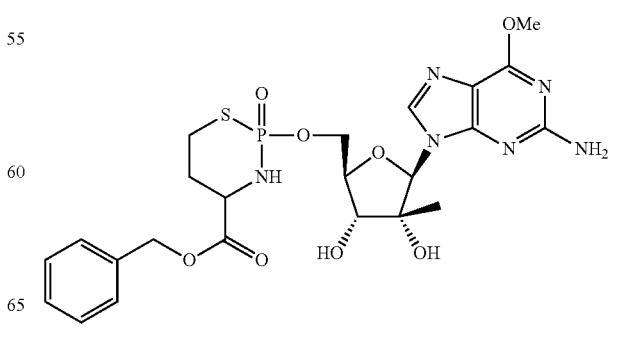
(6)

-continued
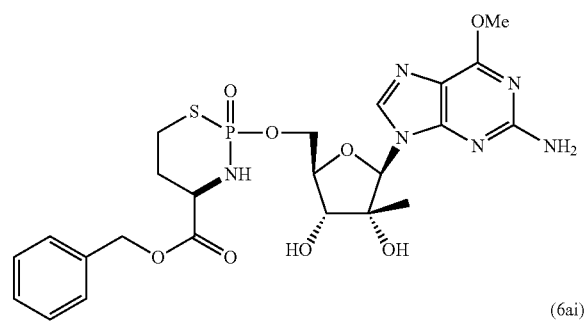
(6a)
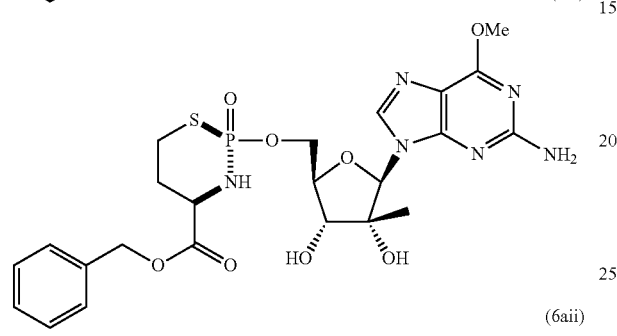
(6ai)
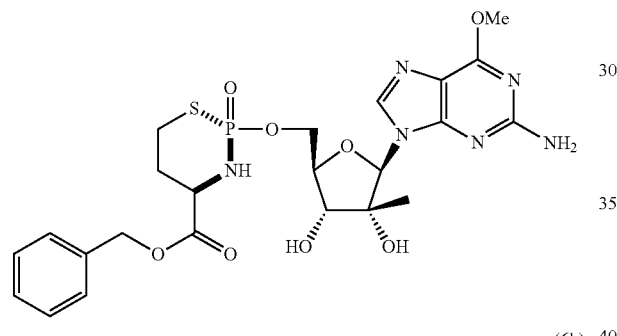
(6aii)
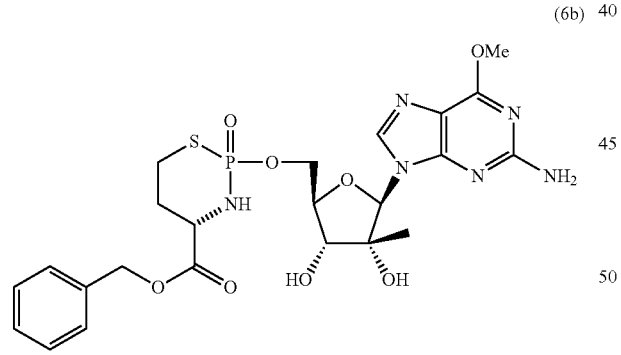
(6b)
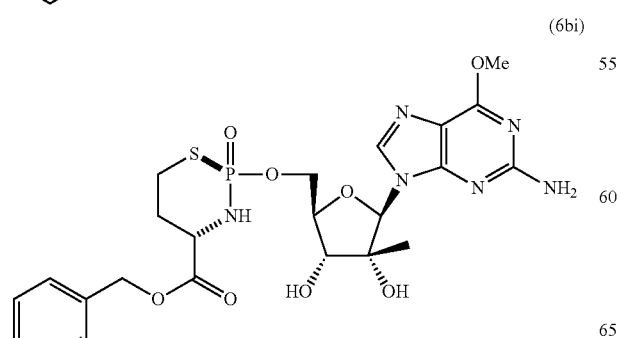
(6bi)
-continued
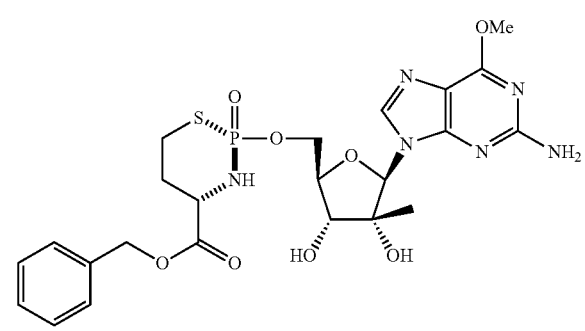
(6bii)
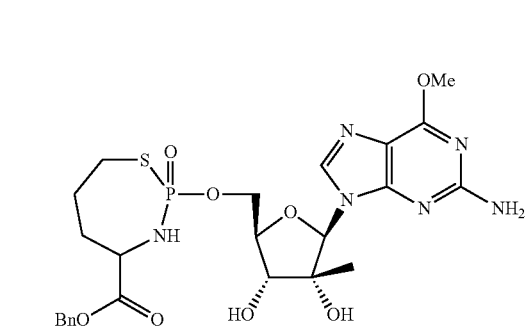
(7)
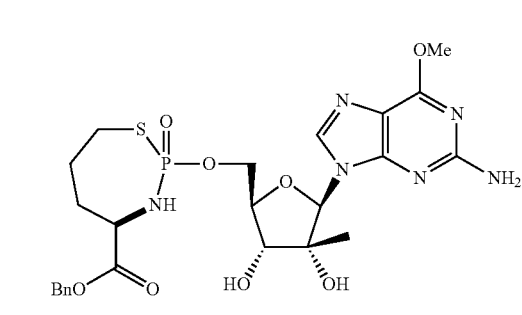
(7a)
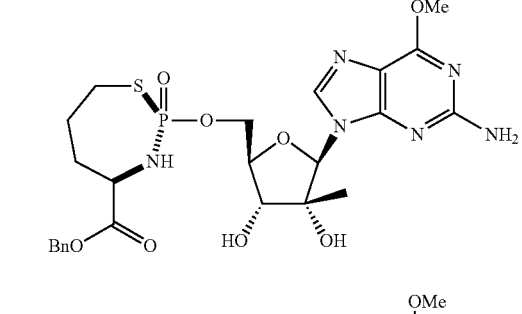
(7ai)
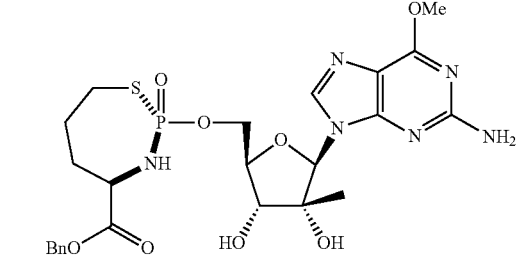
(7aii)

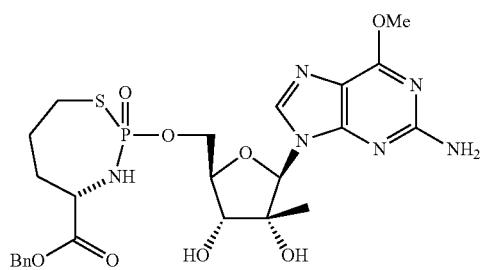
(7b)
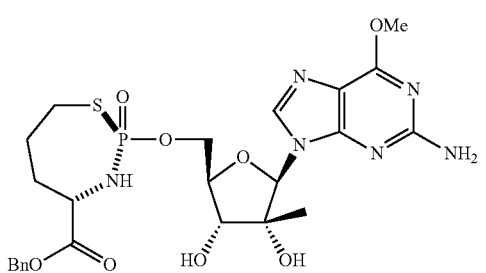
(7bi)
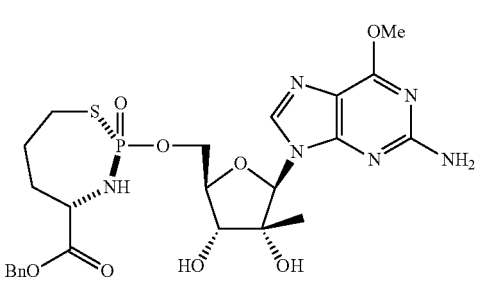
(7bii)
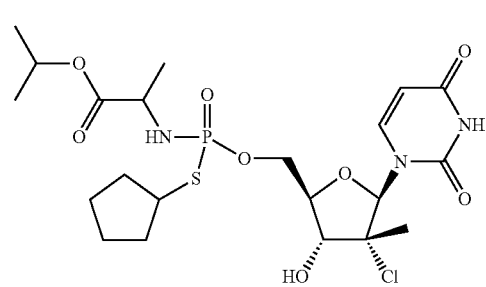
(8)
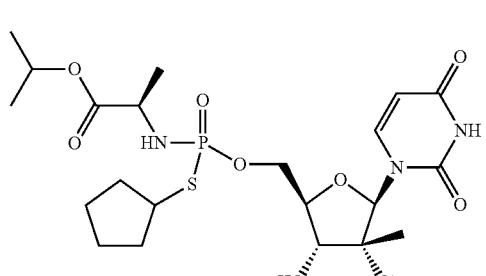
(8a)
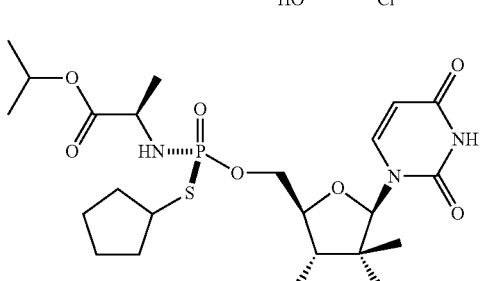
(8ai)
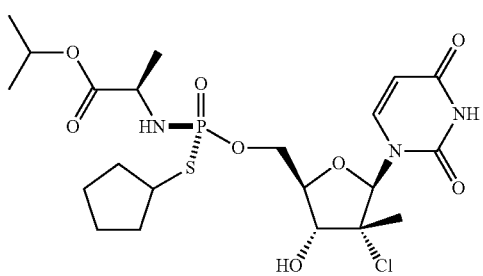
(8aii)
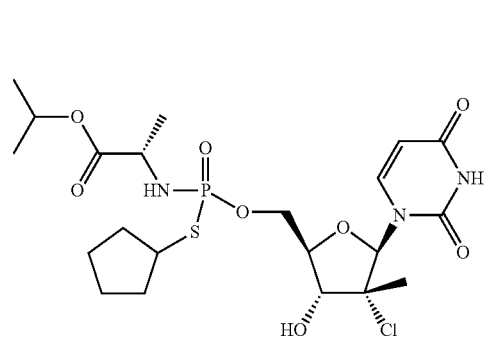
(8b)
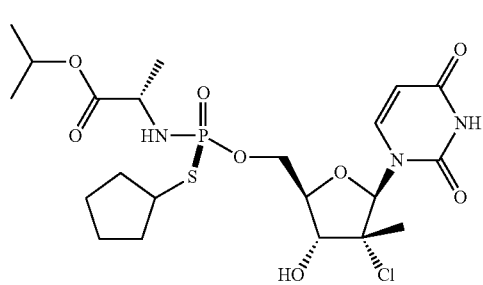
(8bi)
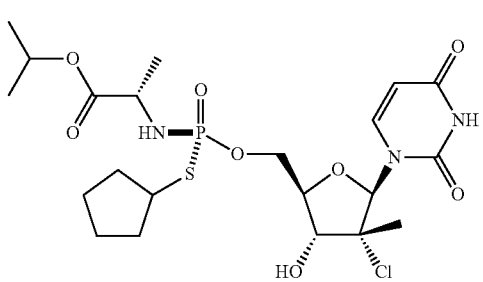
(8bii)
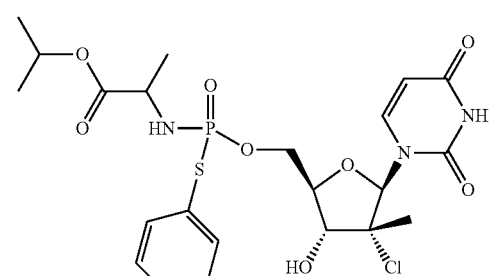
(9)

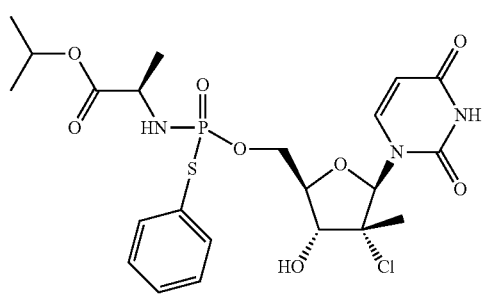 (9a)
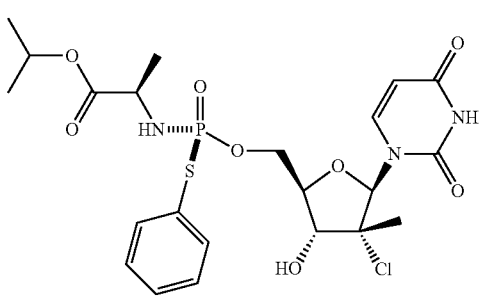 (9ai)
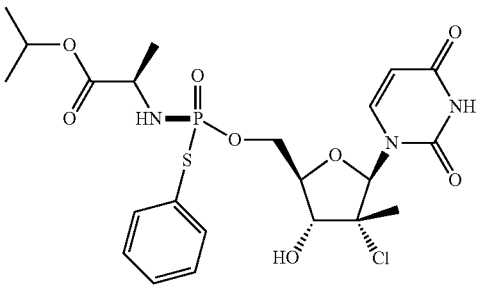 (9aii)
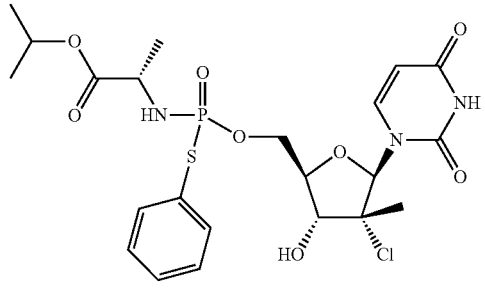 (9b)
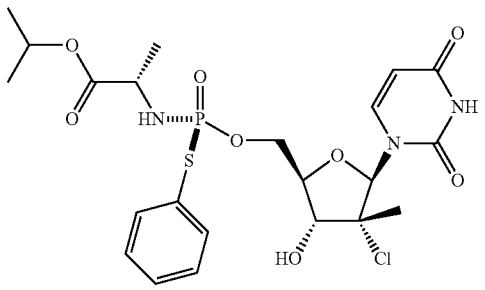 (9bi)
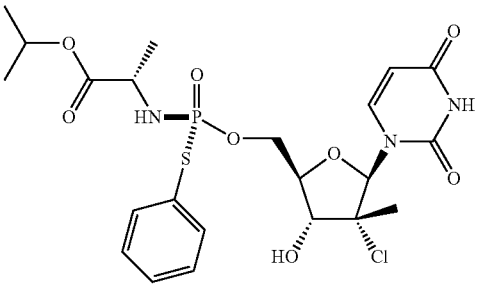 (9bii)
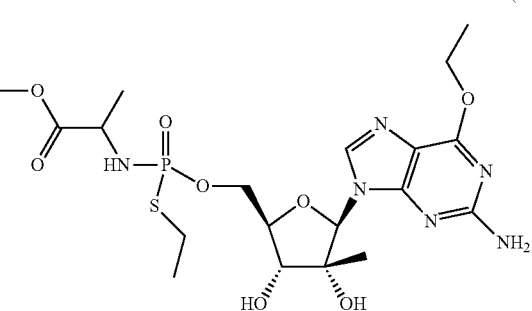 (10)
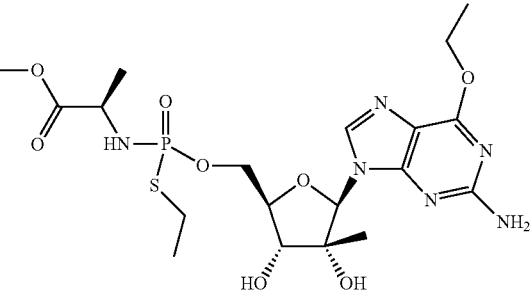 (10a)
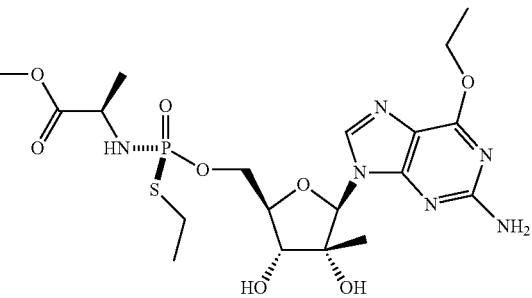 (10ai)
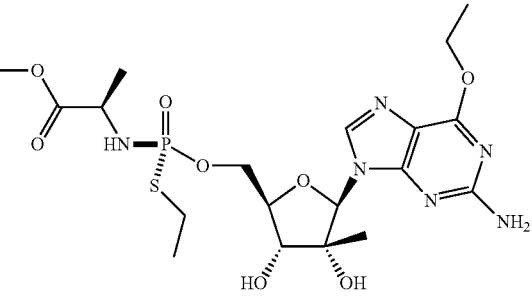 (10aii)

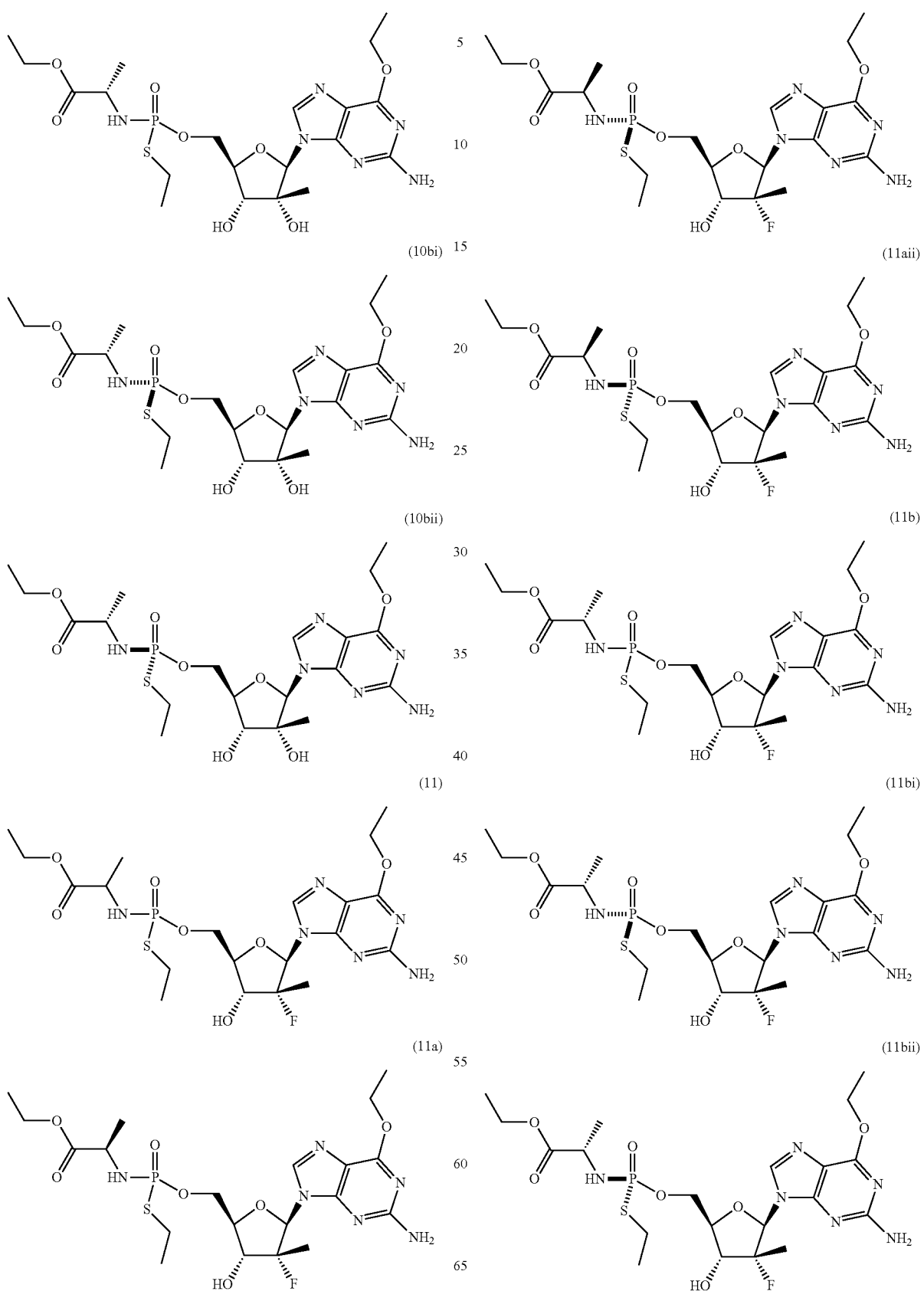

53
-continued
(12)
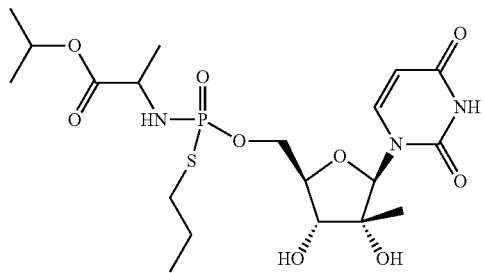
(12a)
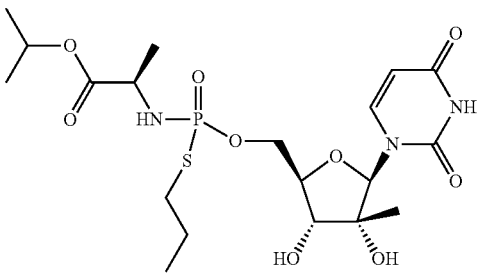
(12ai)
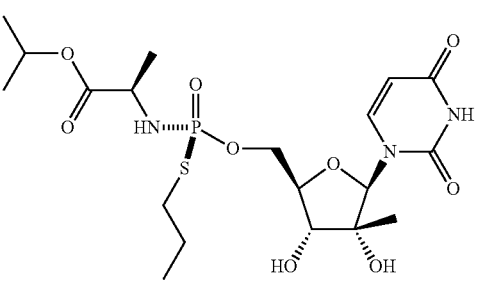
(12aii)
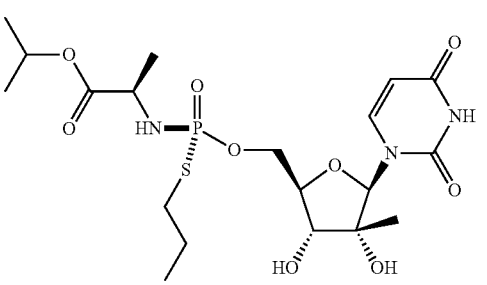
(12b)
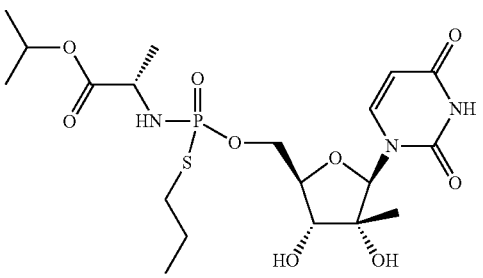
54
-continued
(12bi)
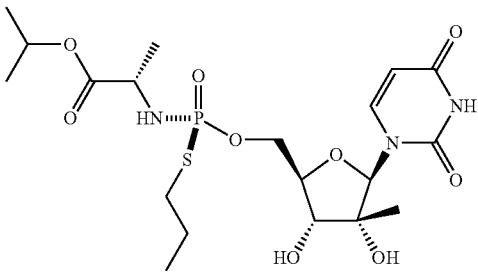
(12bii)
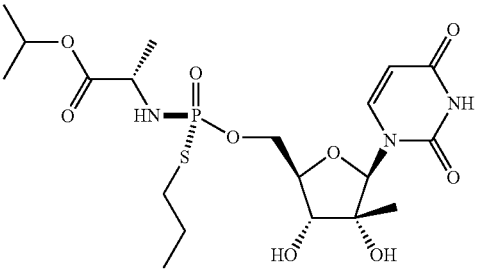
(13)
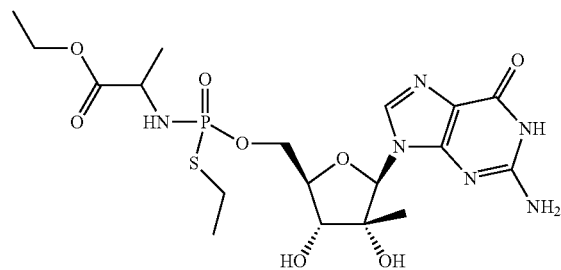
(13a)
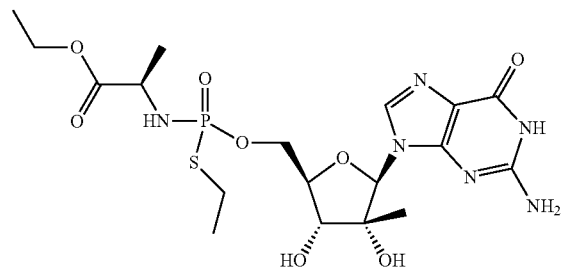
(13ai)
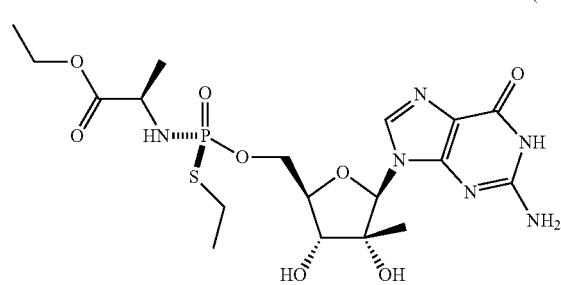

55

(13aii)

(13b)

(13bi)

(13bii)

(14)

56

(14a)

(14ai)

(14aii)

(14b)

(14bi)

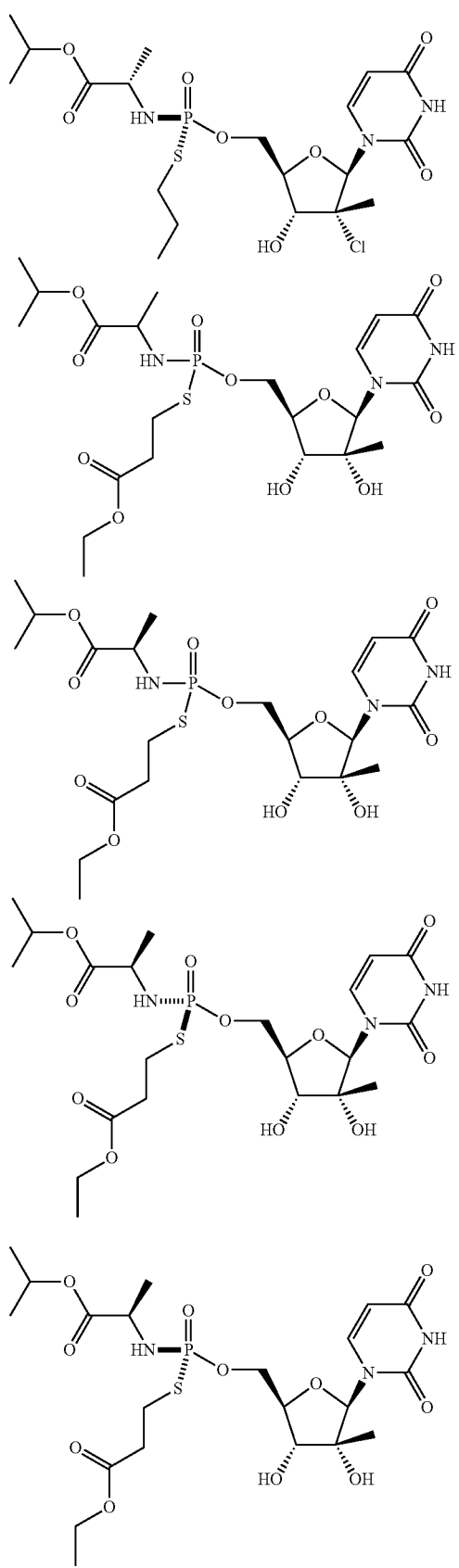
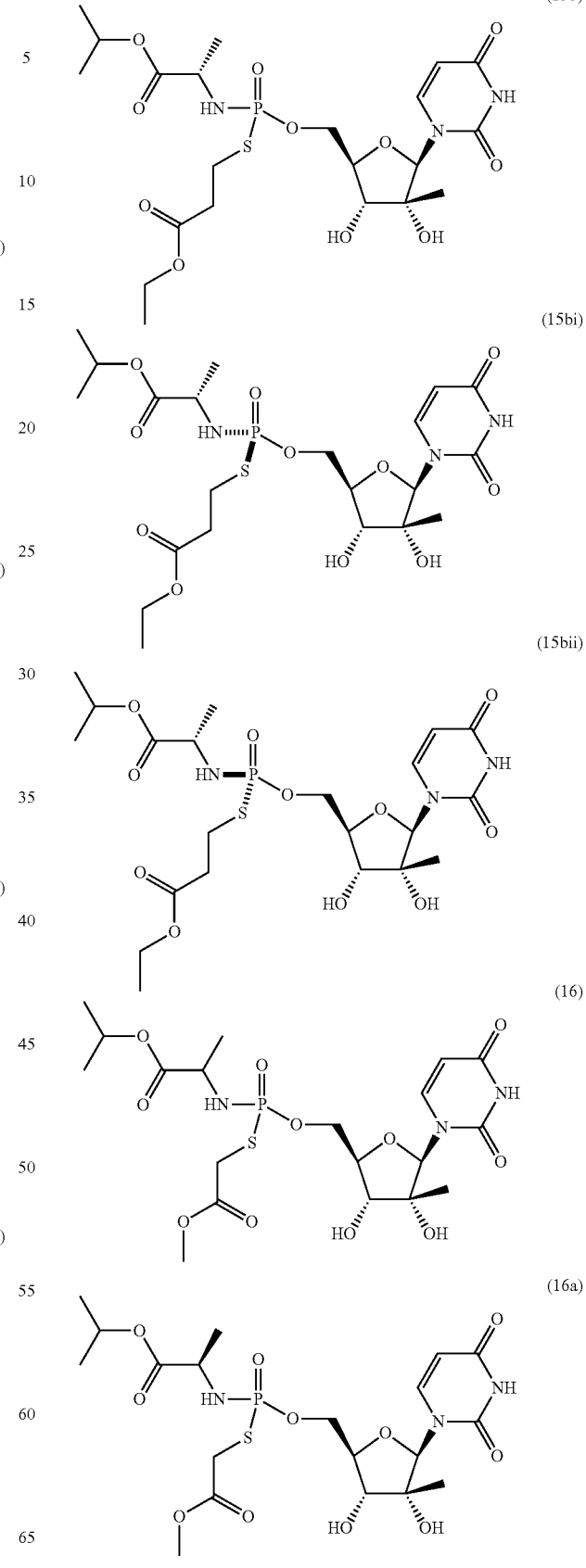

(16ai)
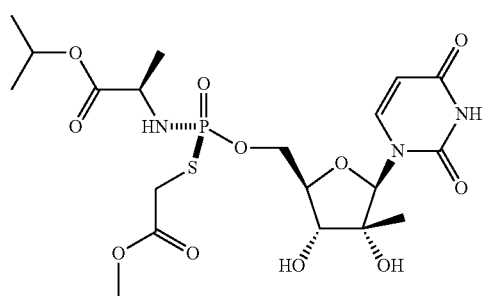
(16aii)
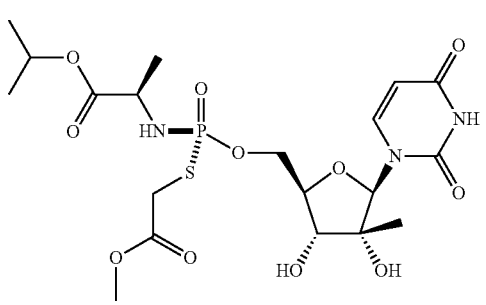
(16b)
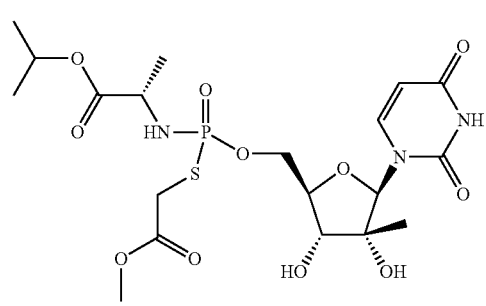
(16bi)
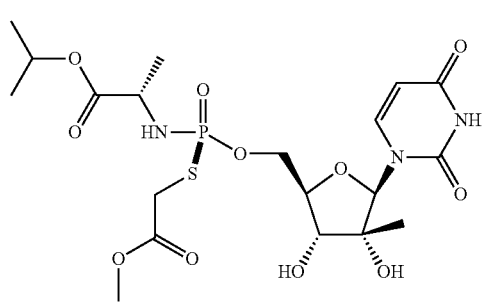
(16bii)
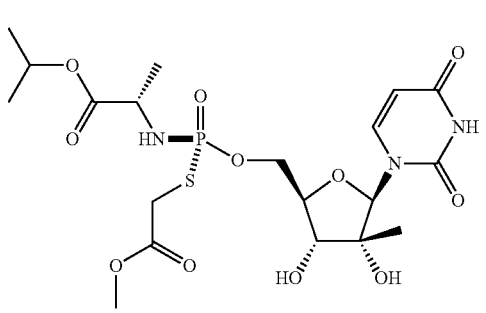
(17)
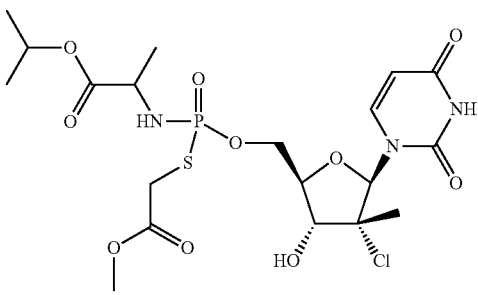
(17a)
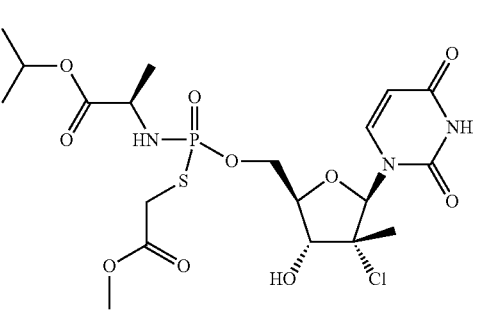
(17ai)
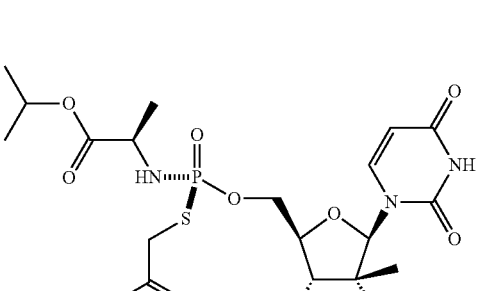
(17aii)
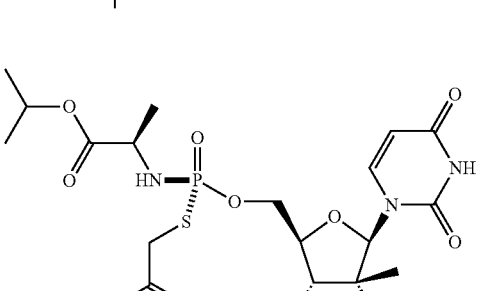
(17b)
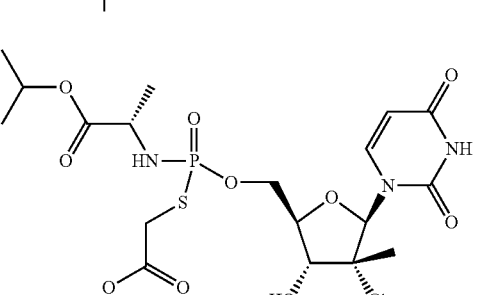

(17bi)
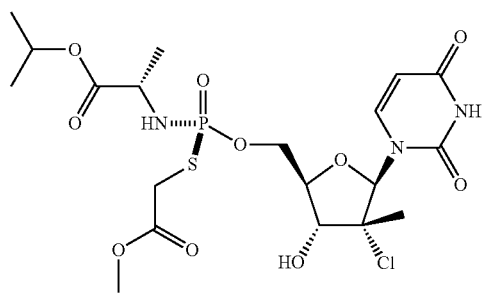
(17bii)
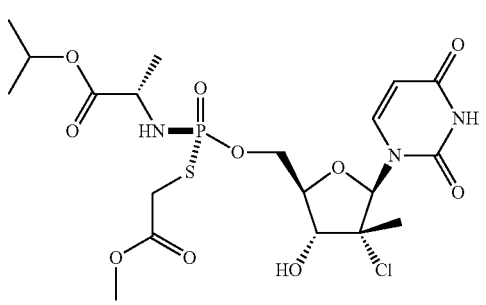
(18)
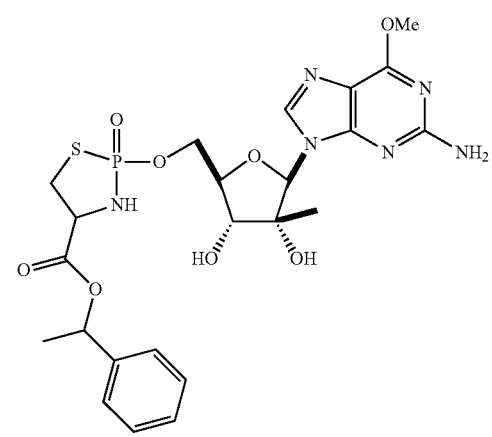
(18a)
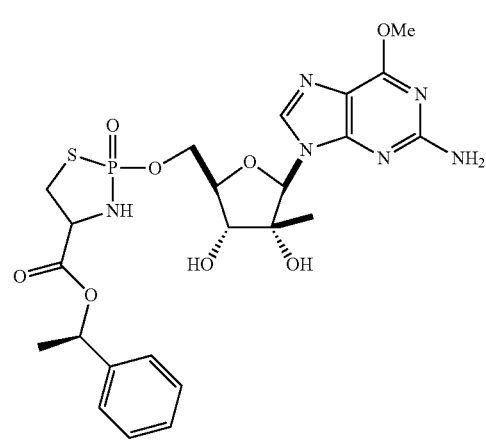
(18ai)
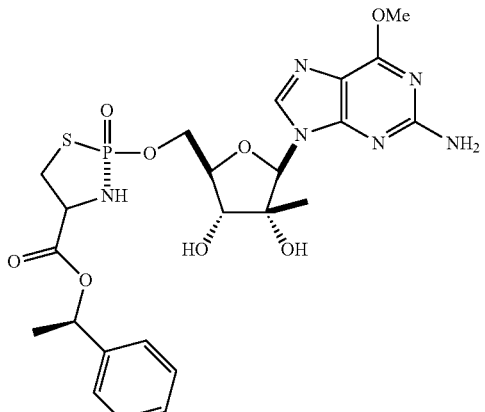
(18aii)
(18b)
(18bi)
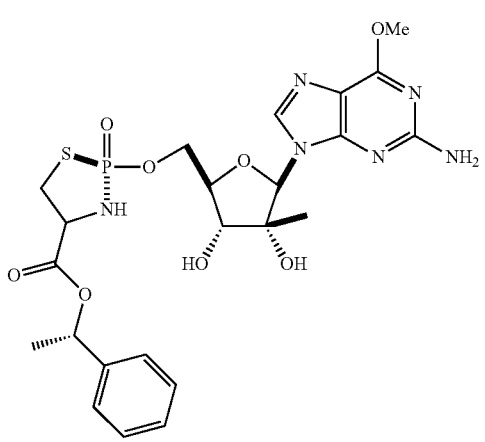

-continued
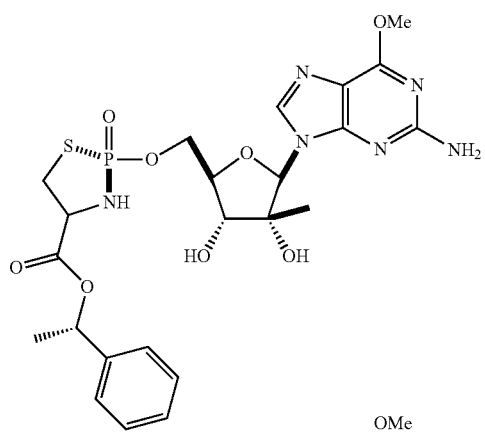
(18bii)
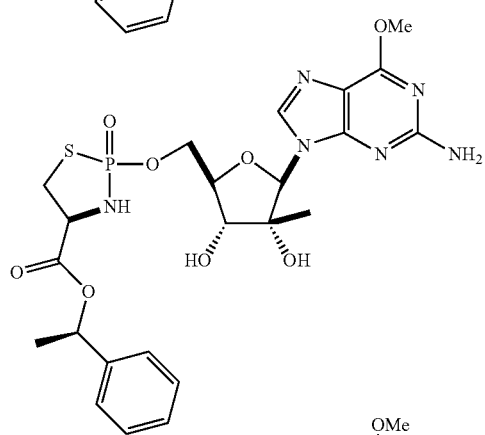
(18ax)
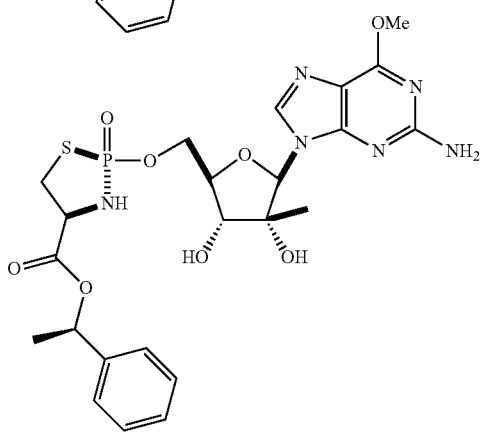
(18axi)
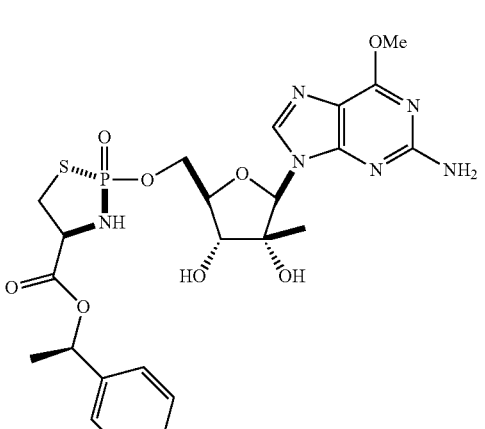
(18axii)
-continued
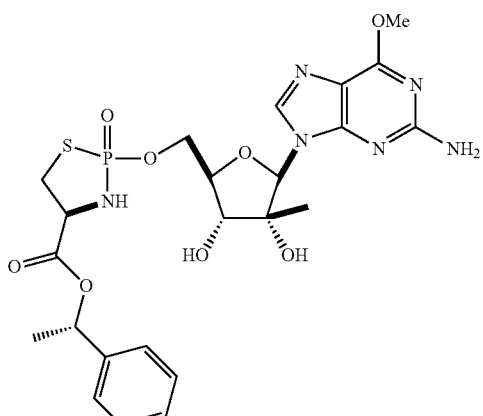
(18bx)
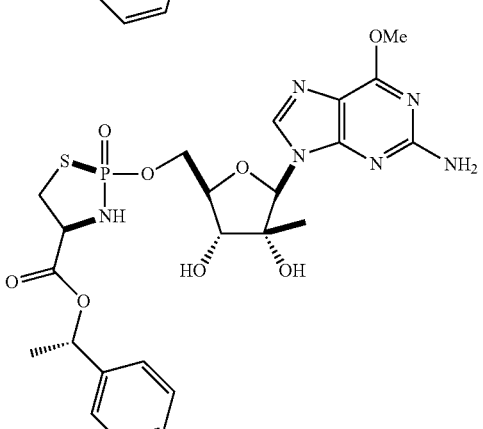
(18bxi)
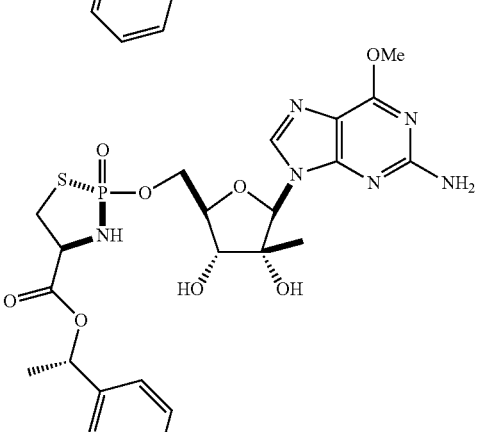
(18bxii)
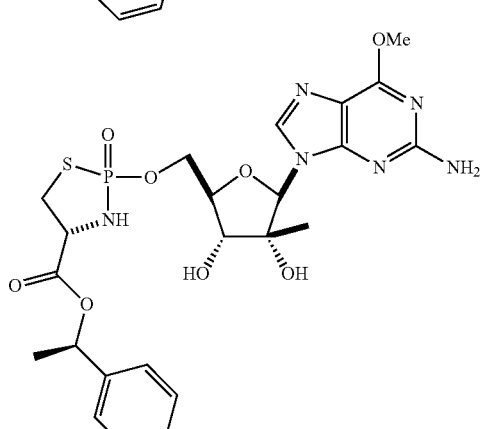
(18ay)

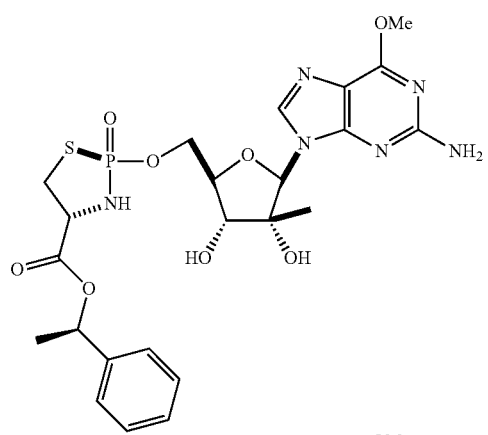
(18ayi)
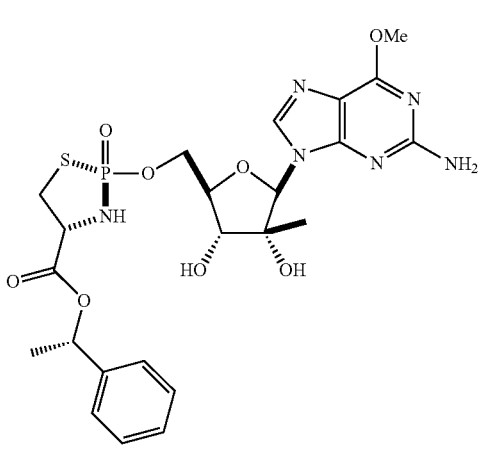
(18byii)
(18ayii)
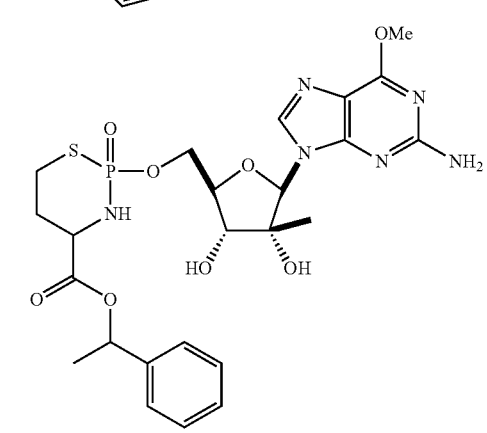
(19)
(18by)
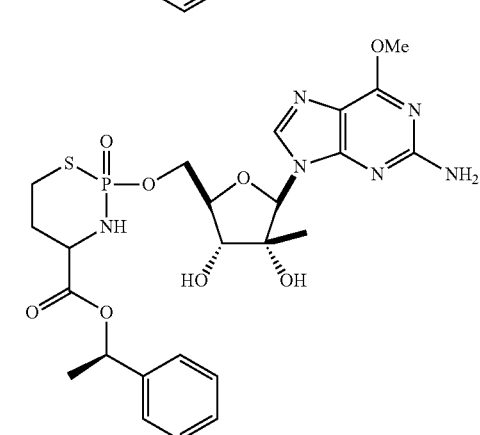
(19a)
(18byi)
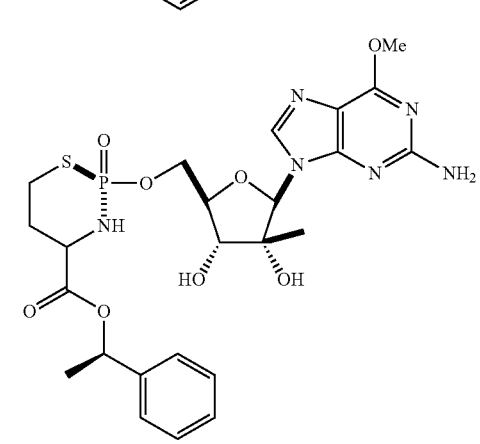
(19ai)

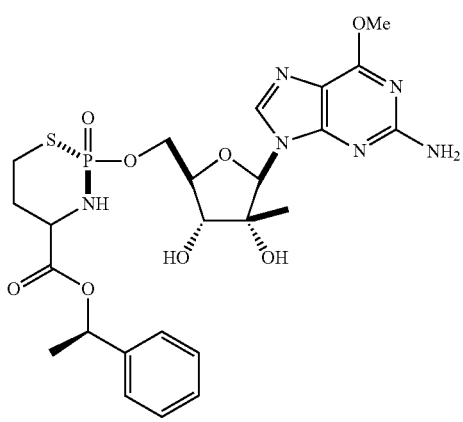
(19aii)
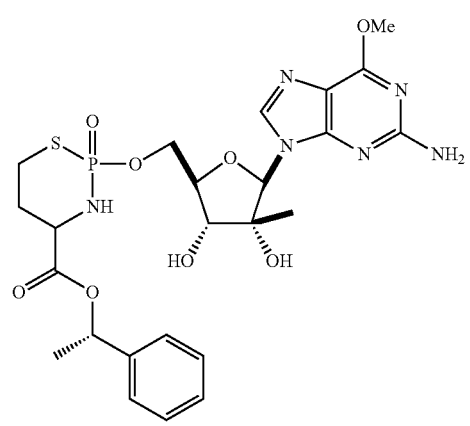
(19b)
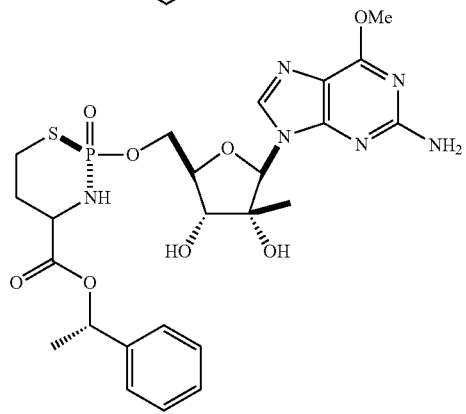
(19bi)
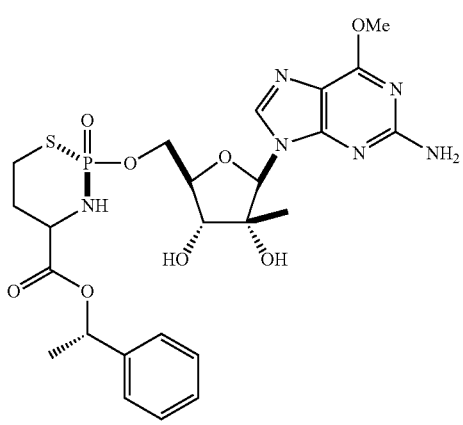
(19bii)
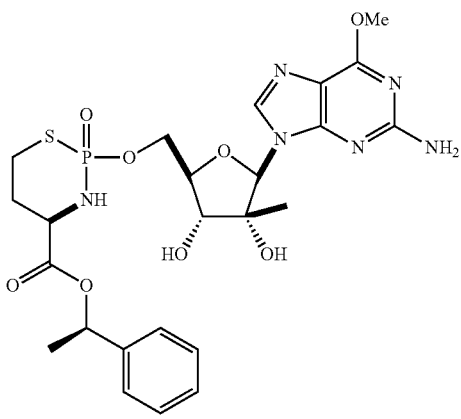
(19ax)
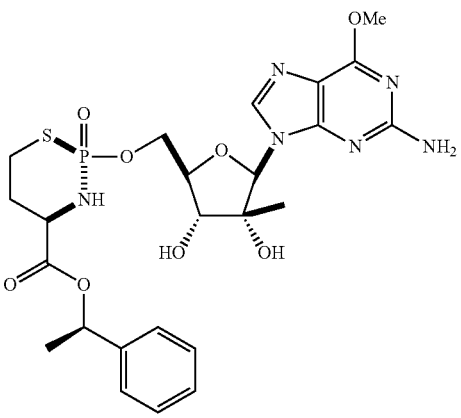
(19axi)
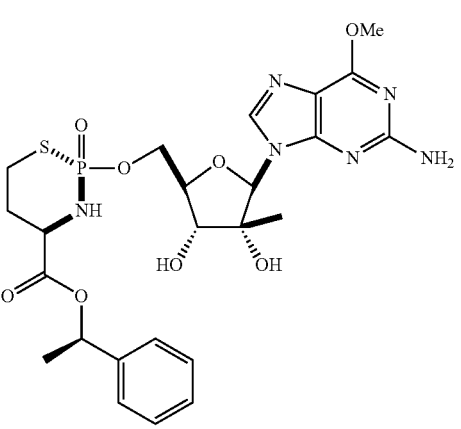
(19axii)
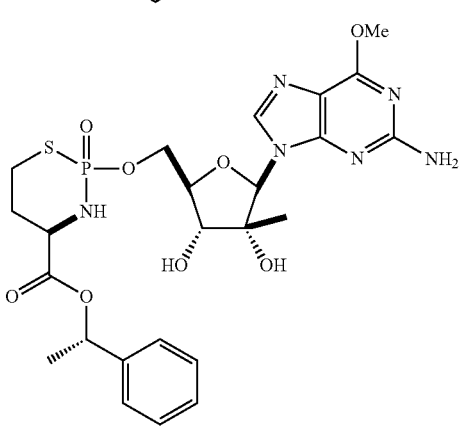
(19bx)

-continued
(19bxi)
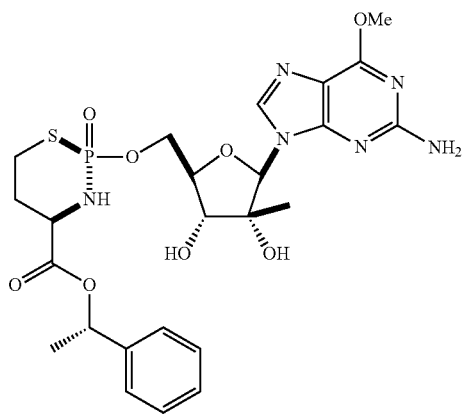
(19bxii)
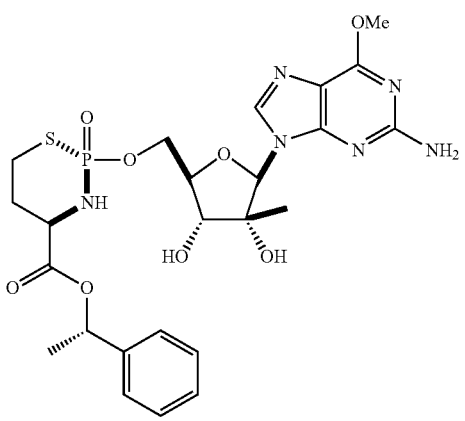
(19ay)
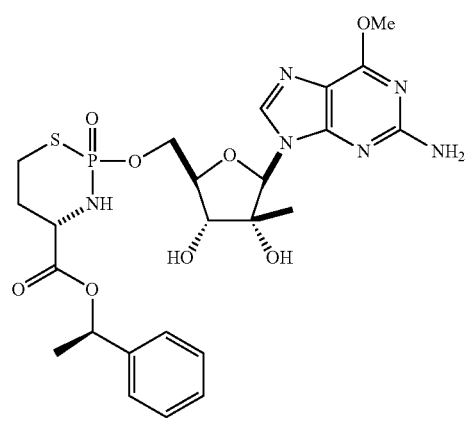
(19ayi)
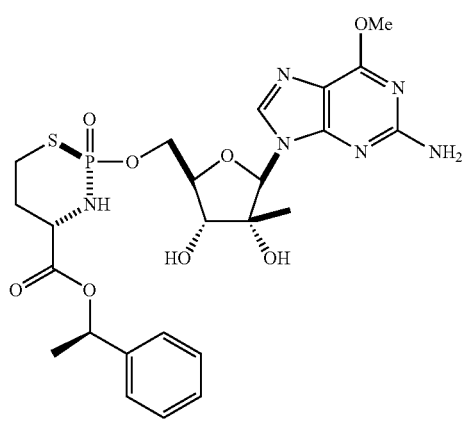
-continued
(19ayii)
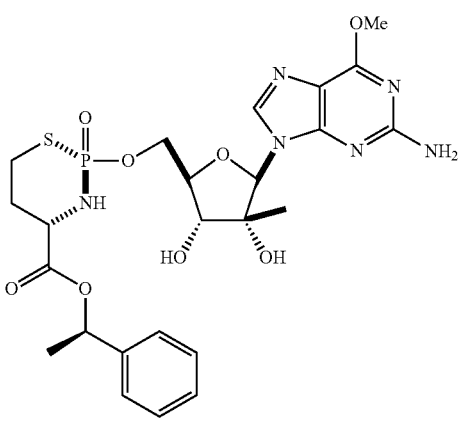
(19by)
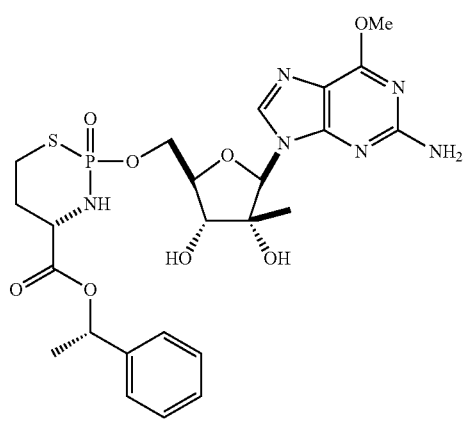
(19byi)
(19byii)
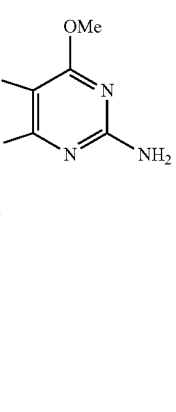

(20)
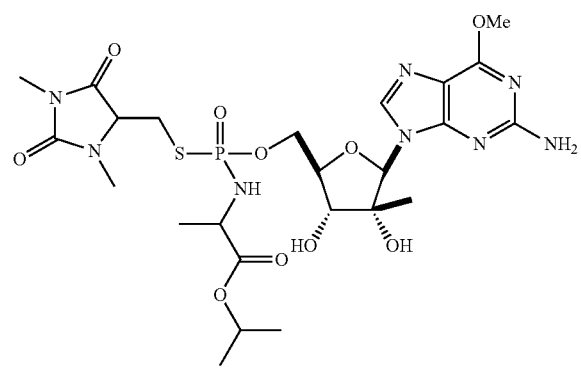
(20a)
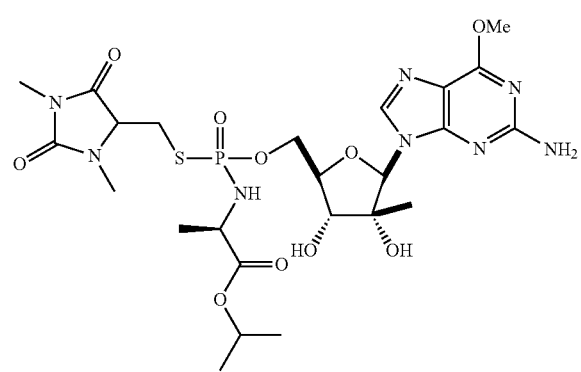
(20ai)
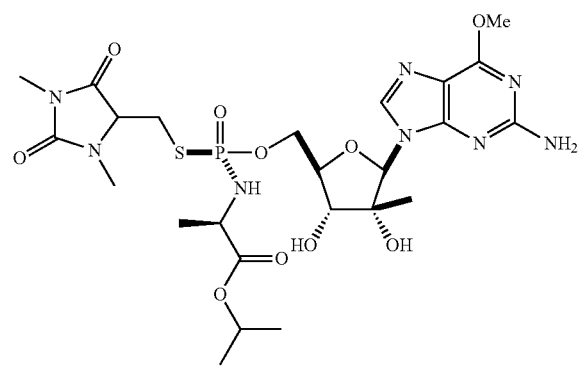
(20aii)
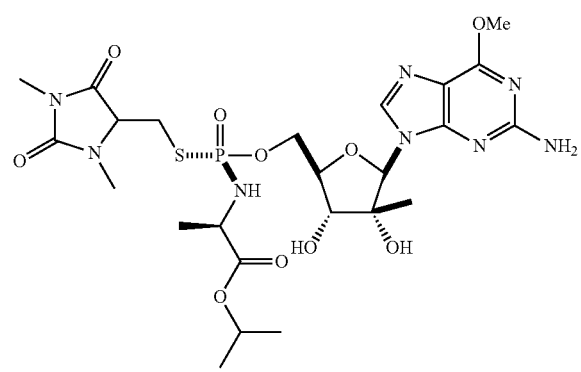
(20b)
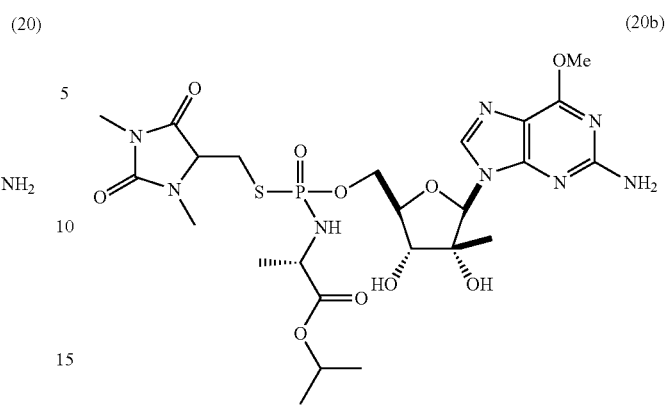
(20bi)
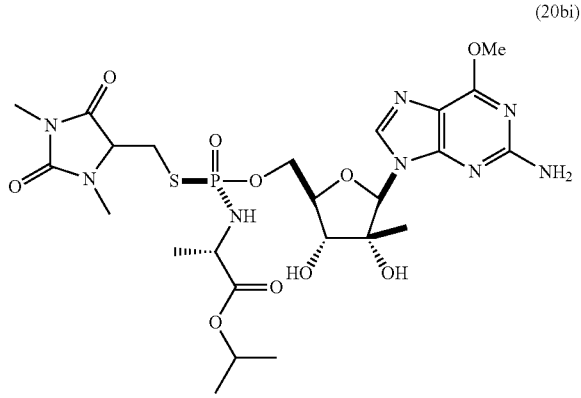
(20bii)
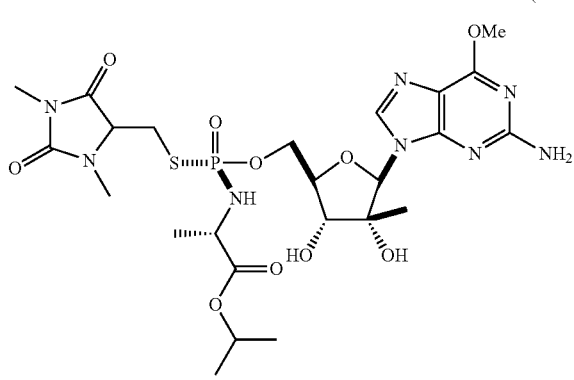
(20ax)
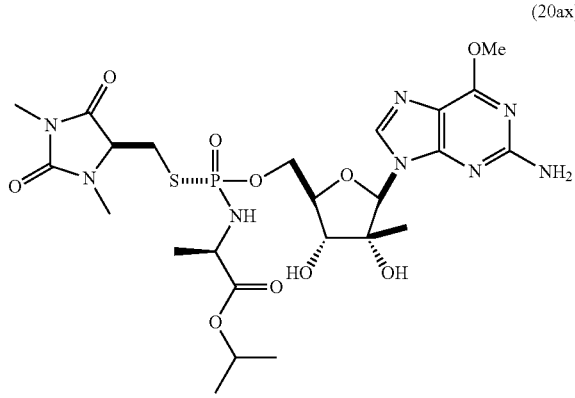

73
-continued
(20axi)
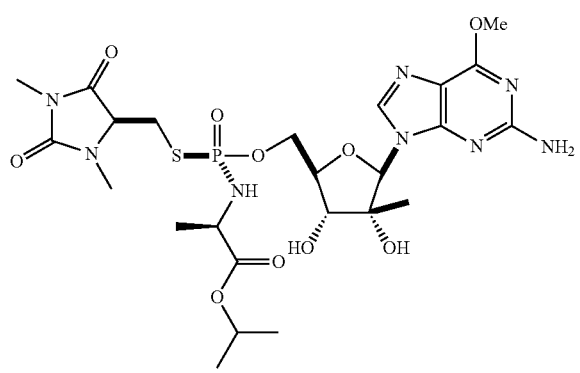
(20axii)
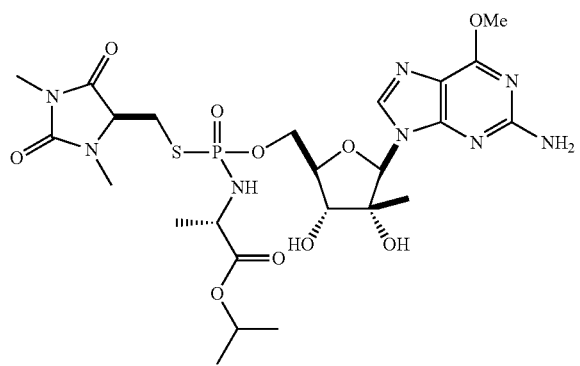
(20bx)
(20bxi)
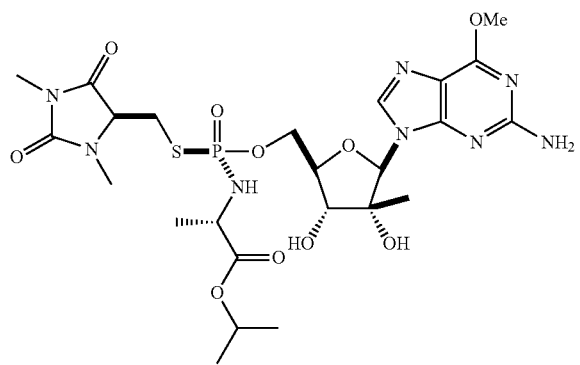
74
-continued
(20bxii)
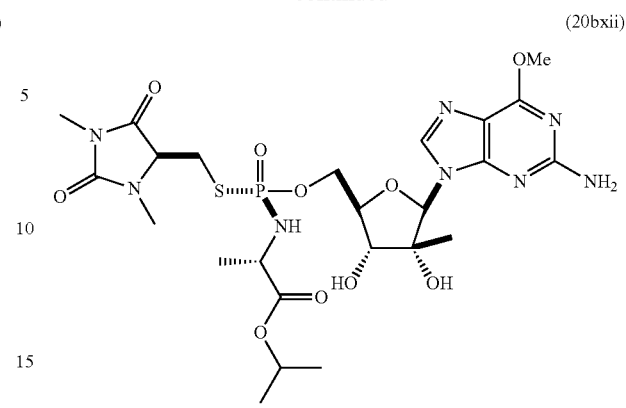
(20ay)
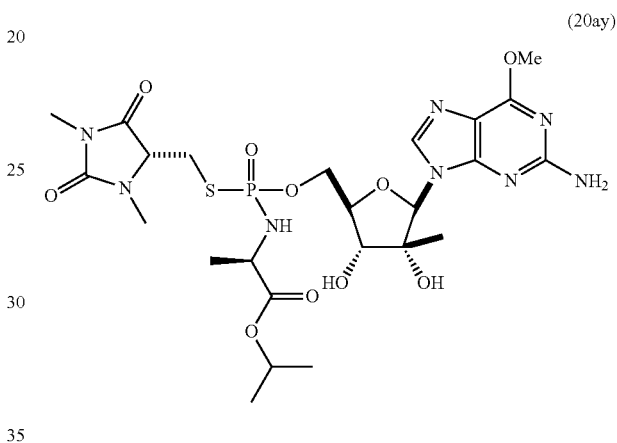
(20ayi)
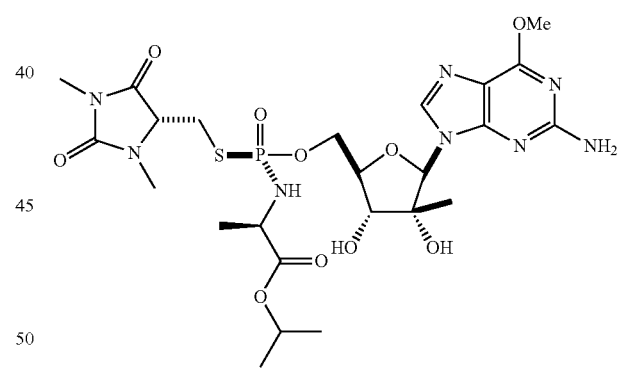
(20ayii)
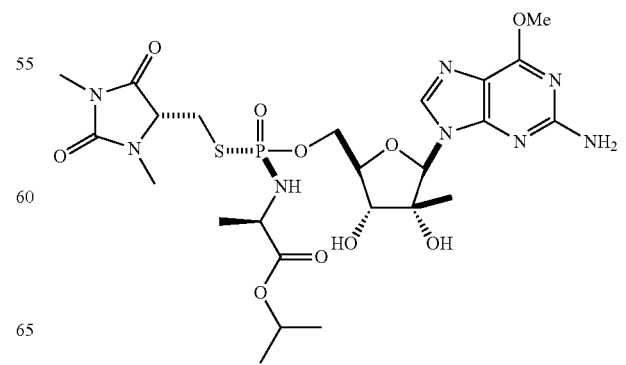

75
-continued
(20by)
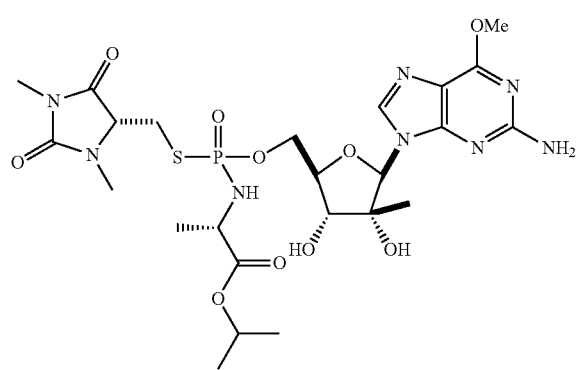
(20byi)
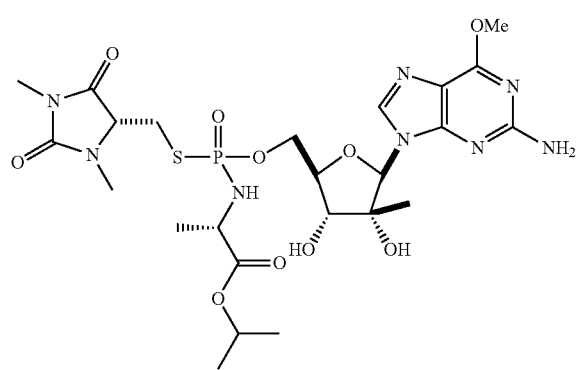
(20byii)
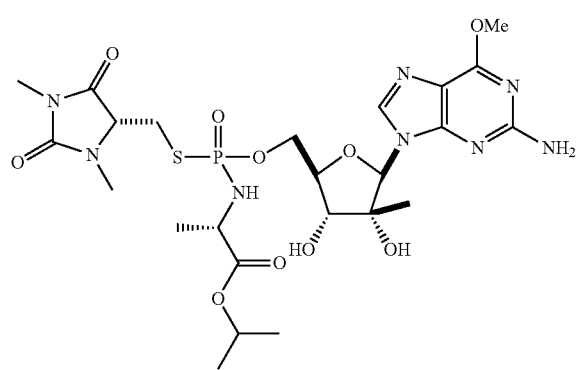
(21)
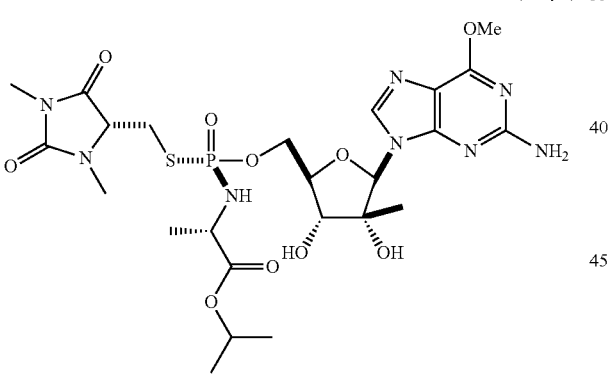
76
-continued
(21a)
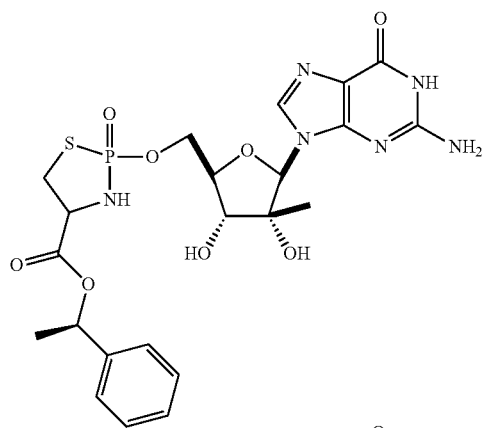
(21ai)
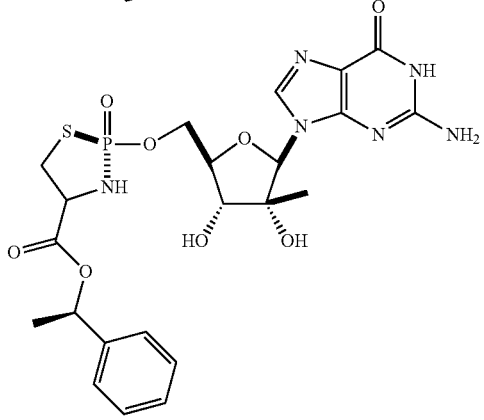
(21aii)
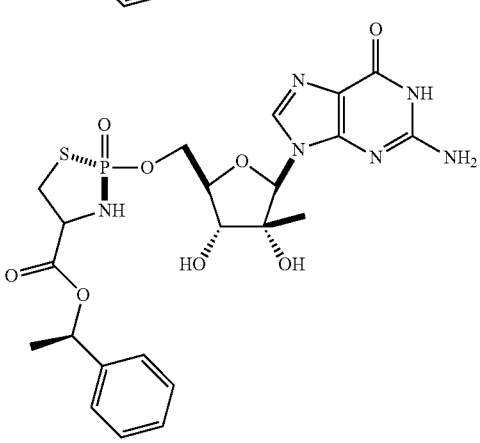
(21b)
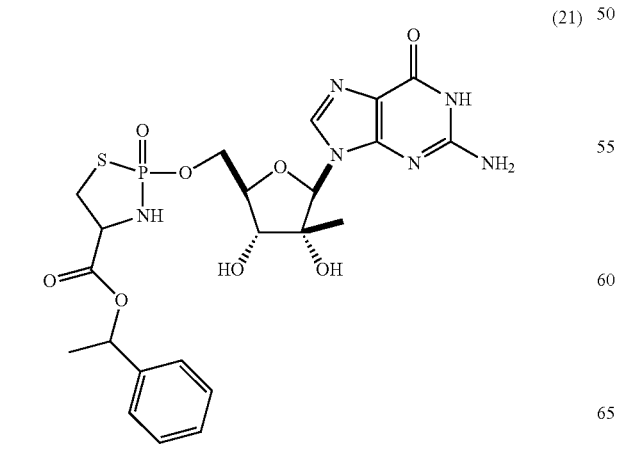

-continued
(21bi)
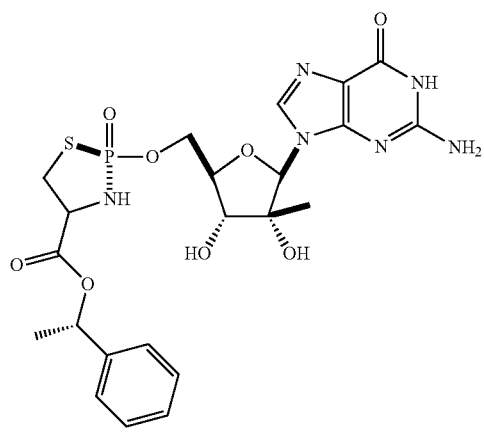
(21bii)
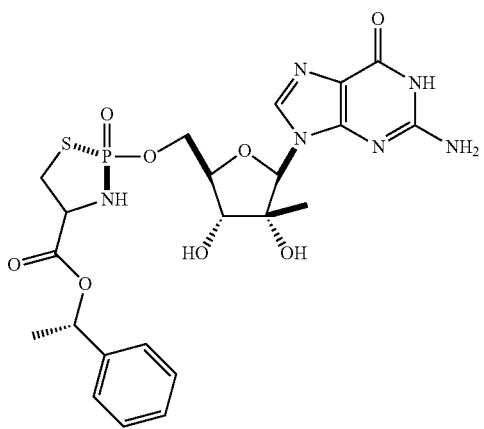
(21ax)
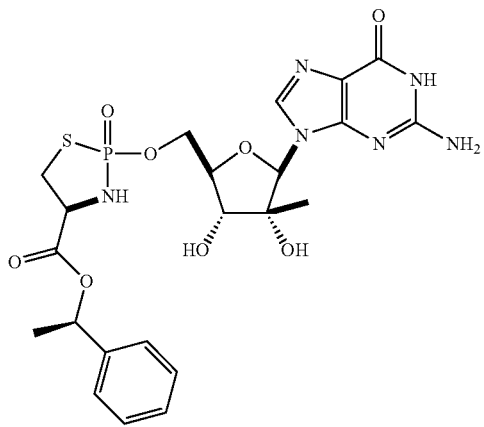
(21axi)
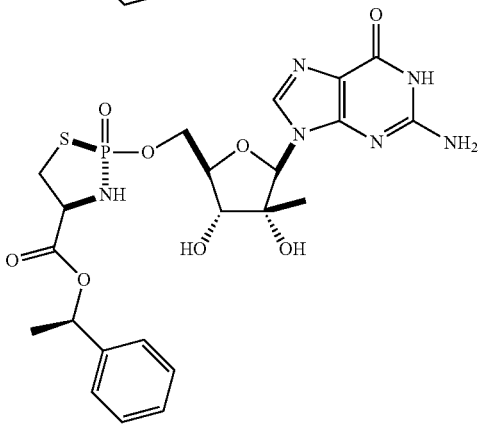
-continued
(21axii)
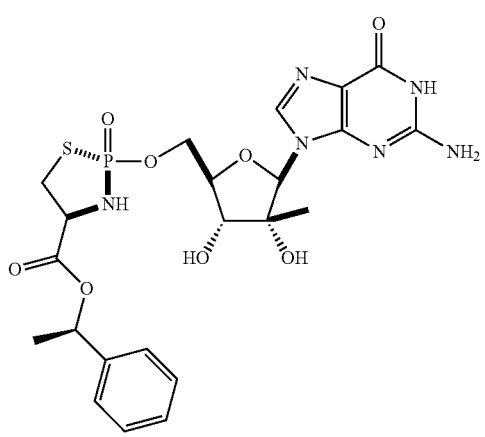
(21bx)
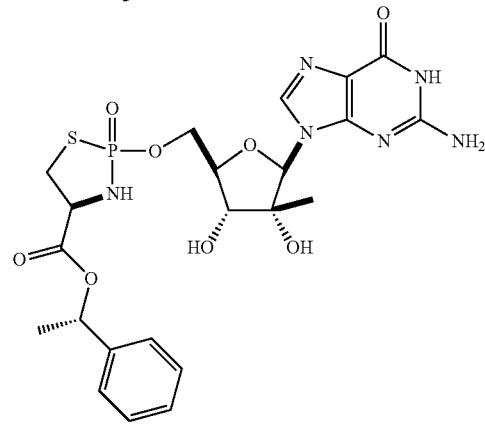
(21bxi)
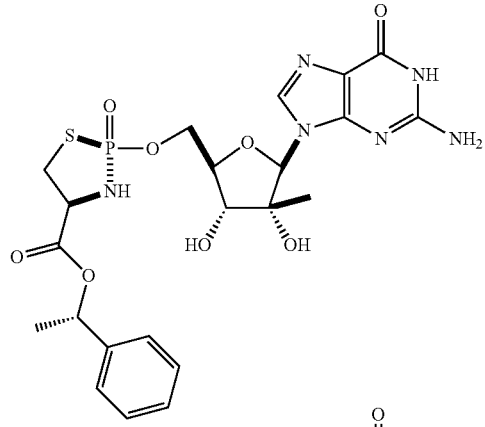
(21bxii)
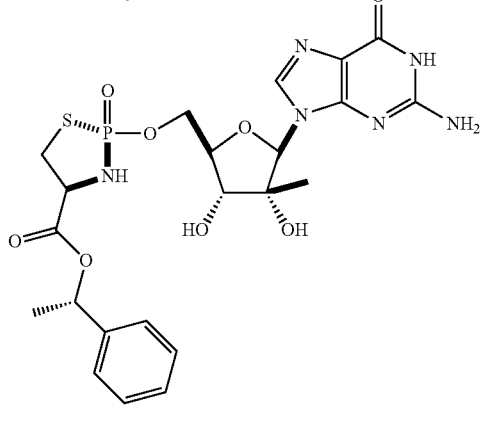

(21ay)
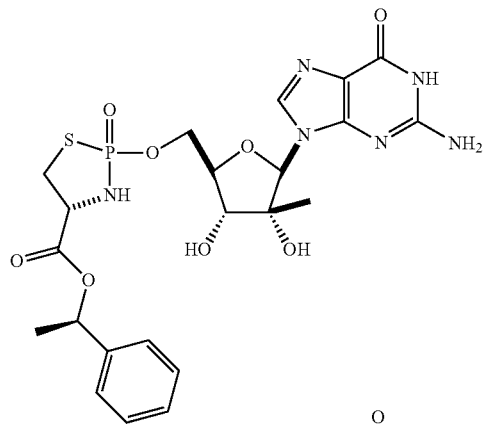
(21ayi)
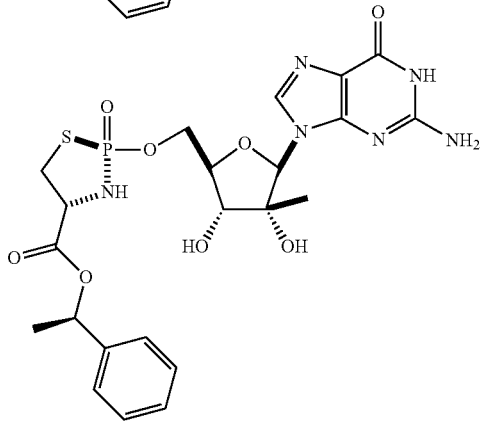
(21ayii)
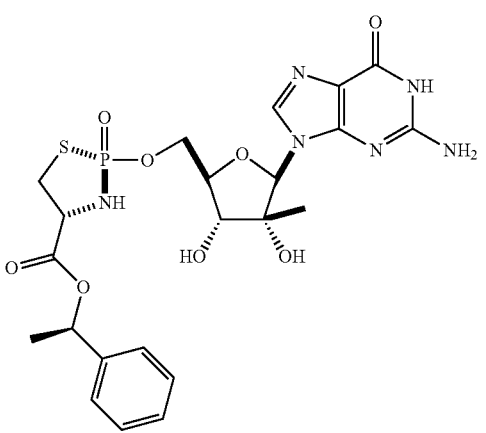
(21by)
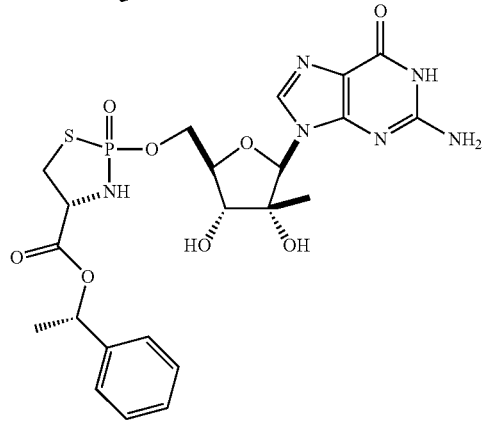
(21byi)
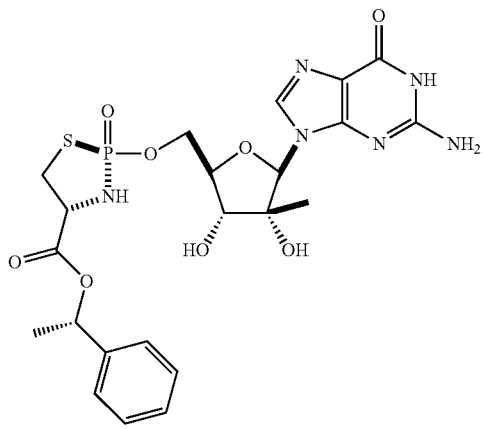
(21byii)
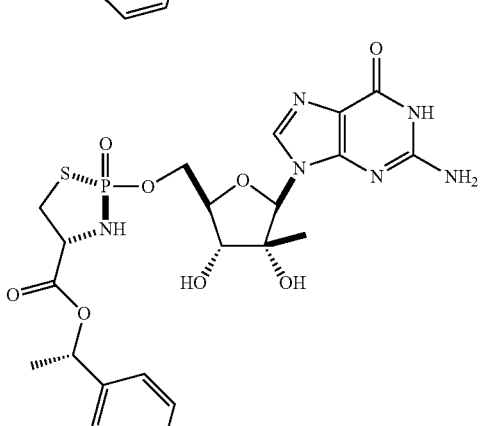
(22)
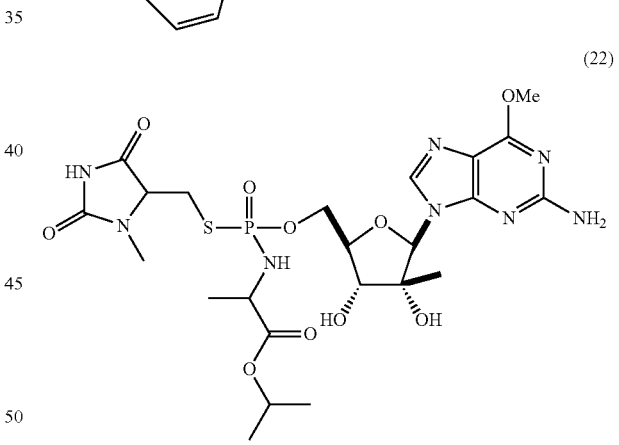
(22a)
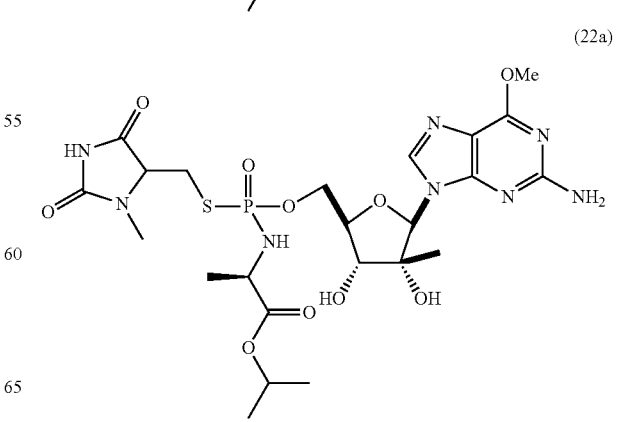

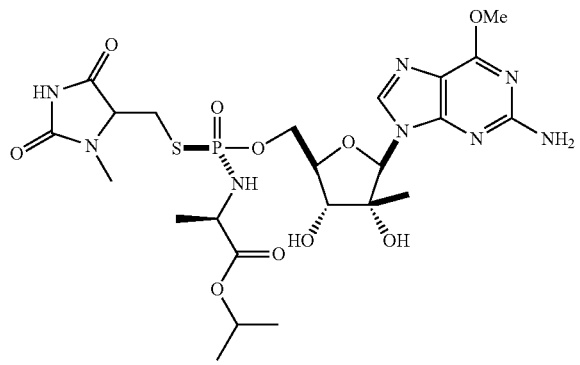
(22ai)
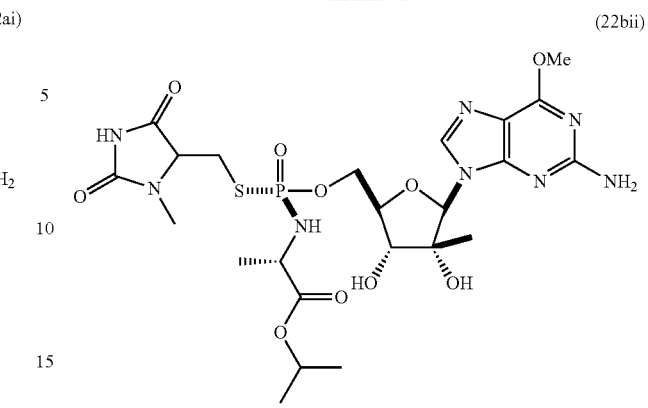
(22bii)
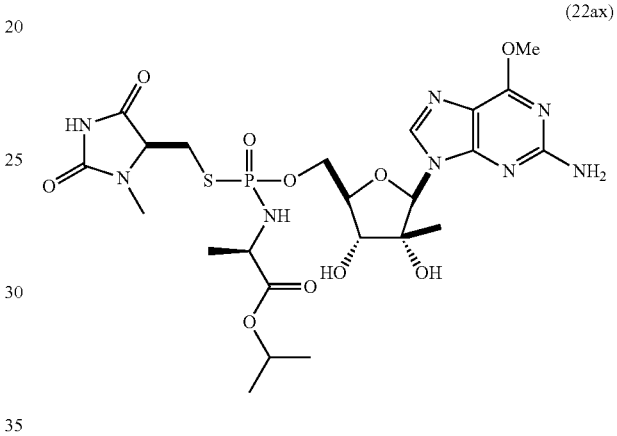
(22ax)
(22aii)
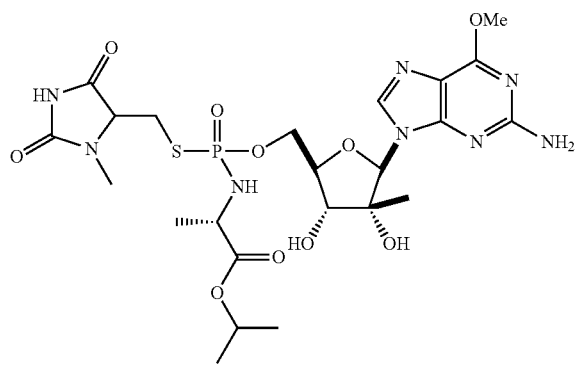
(22b)
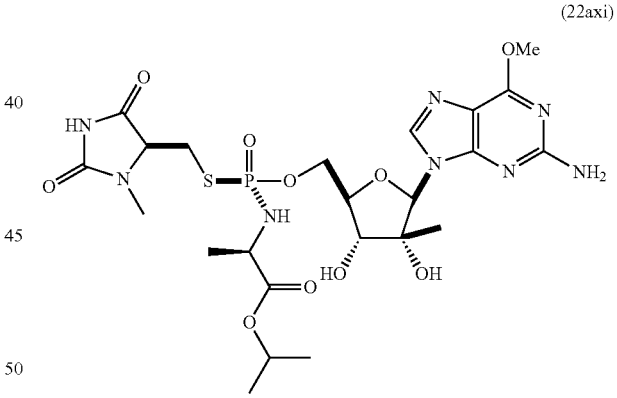
(22axi)
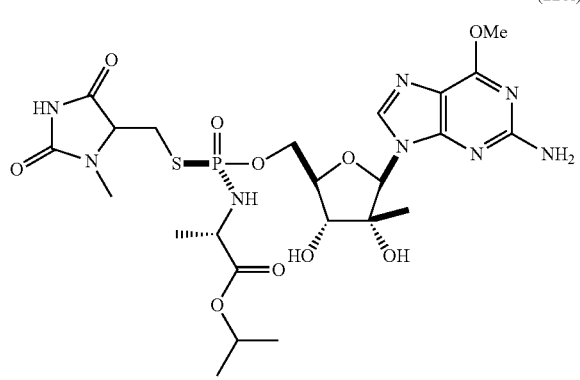
(22bi)
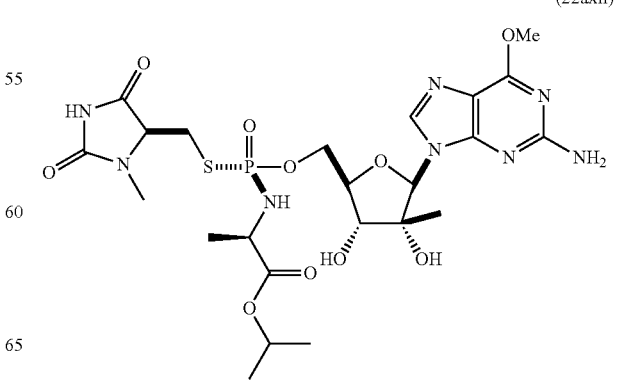
(22axii)

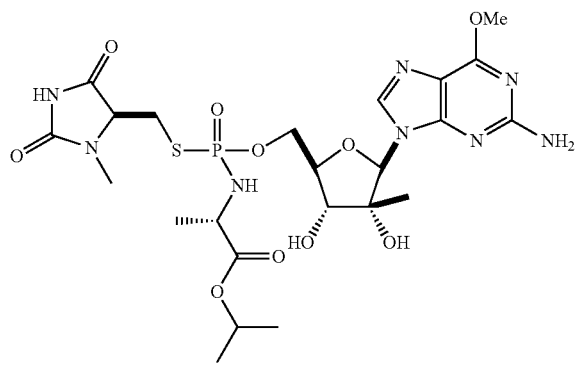
(22bx)
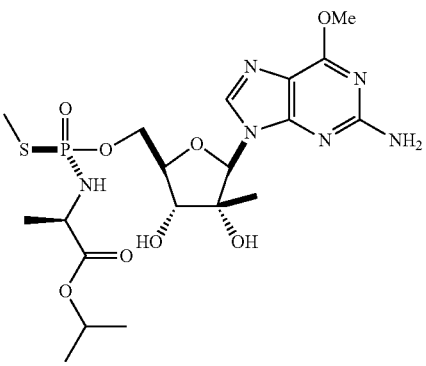
(22ayi)
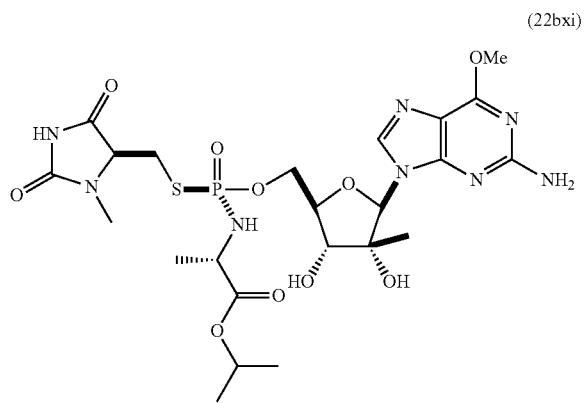
(22bxi)
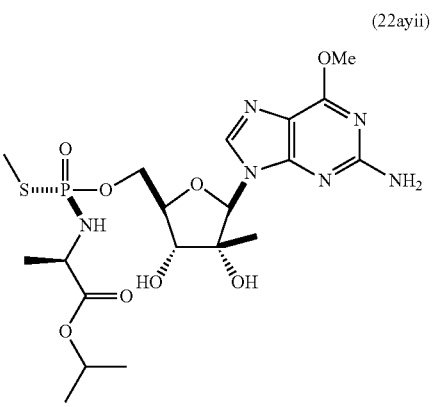
(22ayii)
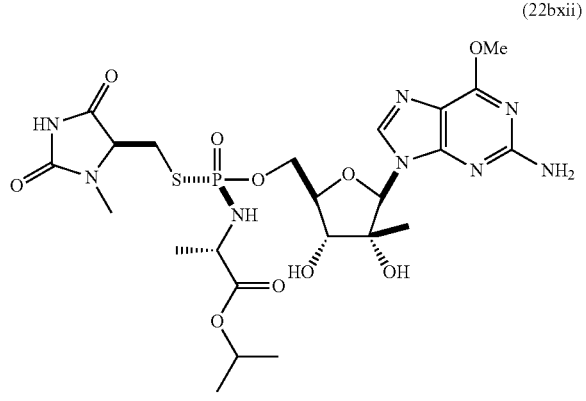
(22bxii)
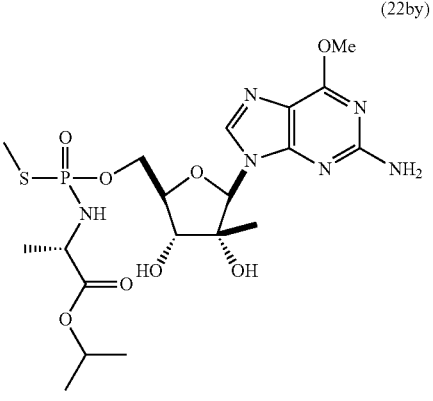
(22by)
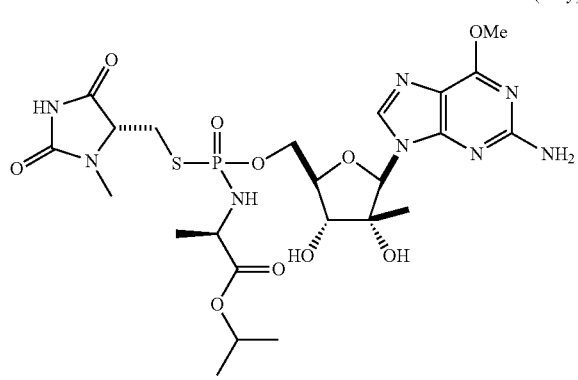
(22ay)
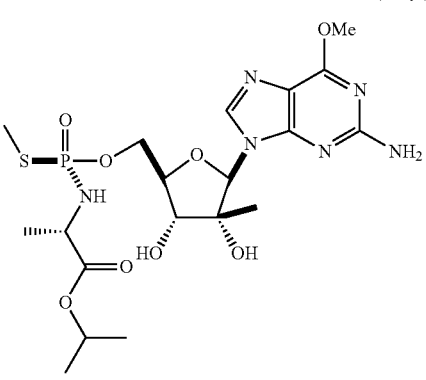
(22byi)

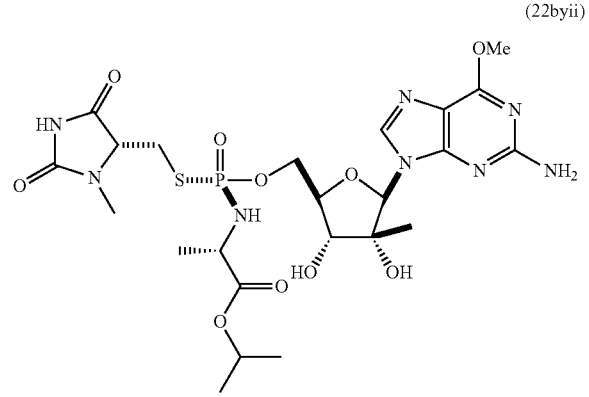
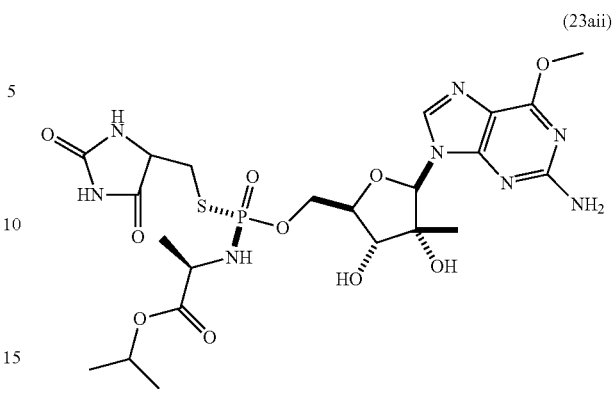

87
-continued
(23ax)
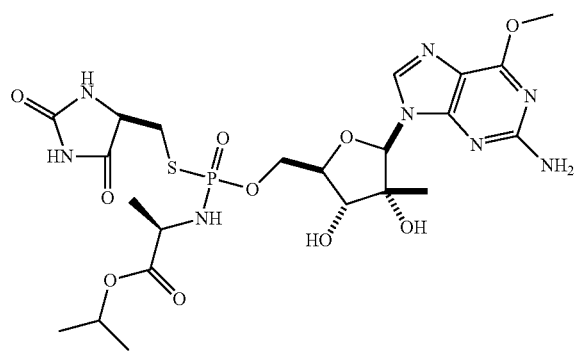
(23axi)
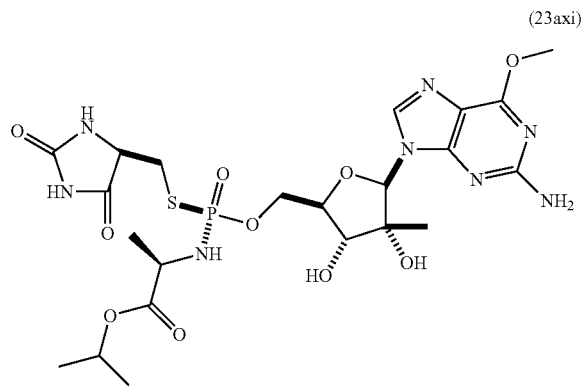
(23axii)
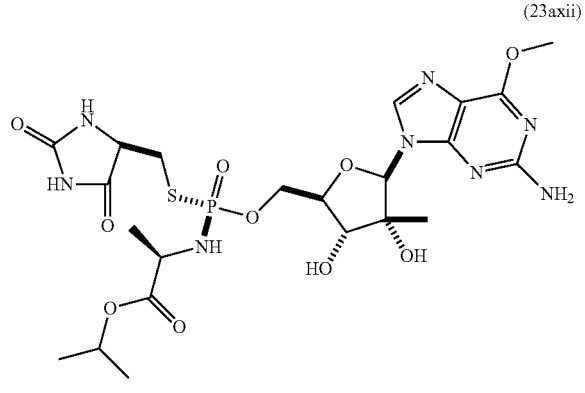
(23bx)
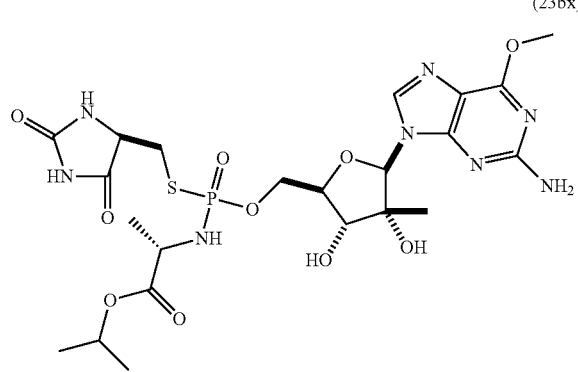
88
-continued
(23bxi)
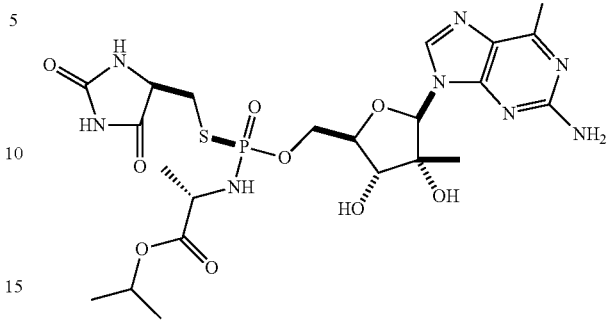
(23bxii)
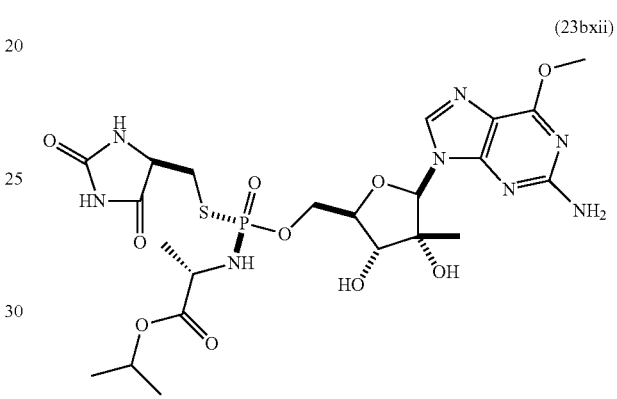
(23ay)
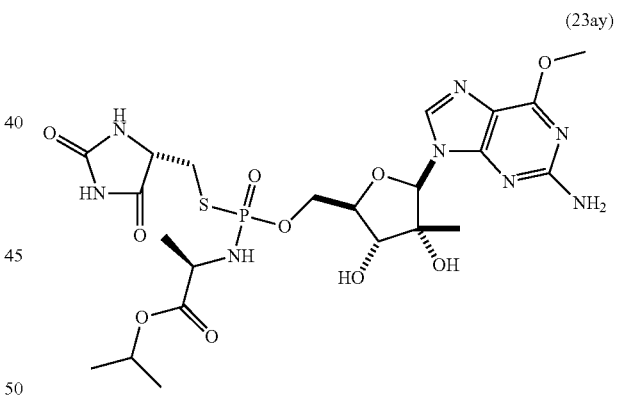
(23ayi)
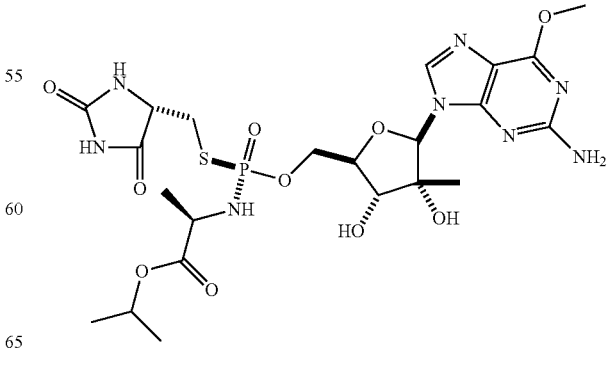

-continued (23ayii)

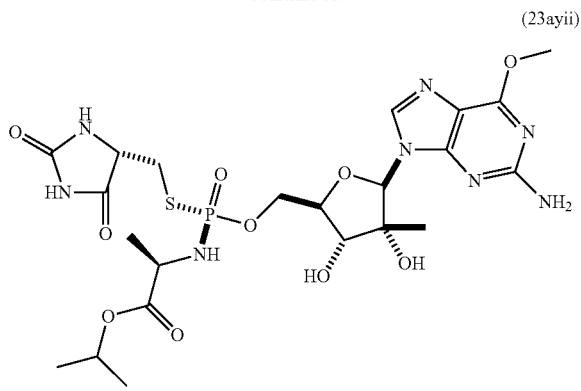

(23by)

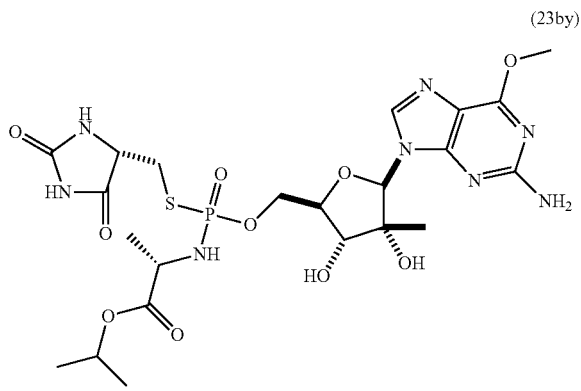

(23byi)

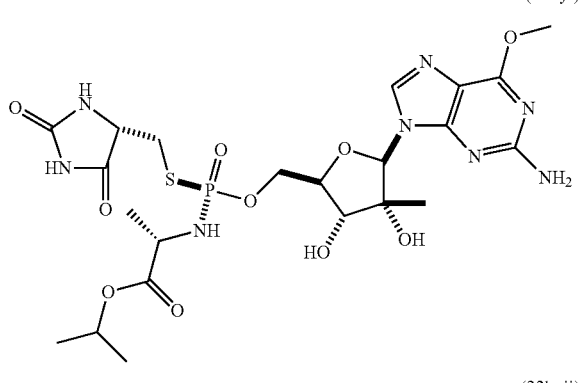

(23byii)

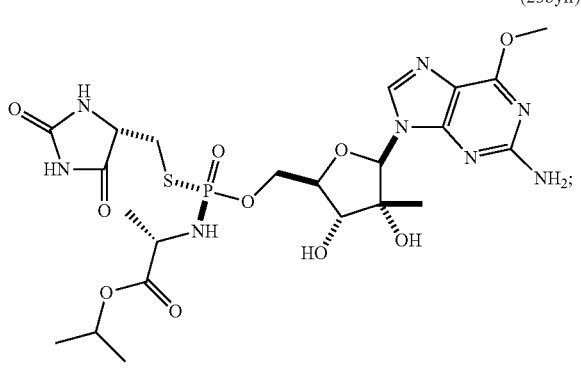

or a pharmaceutically acceptable salt, solvate, stereoisomeric form, tautomeric form, or polymorphic form thereof.

In certain embodiments, provided herein are compounds according to Formula (1001):

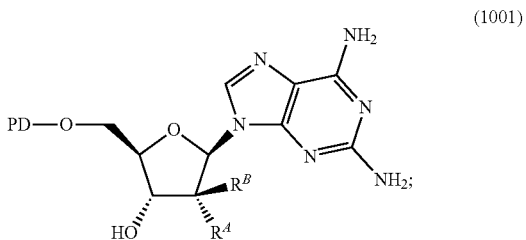

(1001)

or a pharmaceutically acceptable salt, solvate, stereoisomeric form, tautomeric form, or polymorphic form thereof, wherein: $R^A$ is hydroxyl or halo; $R^B$ is methyl or halo; PD is

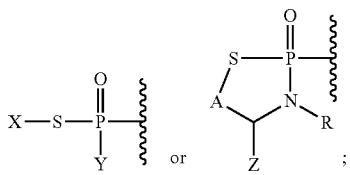

X is alkyl, alkoxycarbonylalkyl, (alkoxycarbonyl)(alkoxycarbonylamino)alkyl, cycloalkyl, heterocycloalkyl, hydantoinylalkyl, or aryl; Y is —$NR^1R^2$ or an N-linked amino acid, or ester thereof; Z is alkyl, alkoxycarbonyl or alkoxyalkylcarbonyl; A is —$CHR^{10}$—, —$CHR^{10}CHR^{11}$—, or —$CHR^{10}CHR^{11}CHR^{12}$—; $R^1$ is hydrogen, alkyl, cycloalkyl, aryl, heteroaryl, arylalkyl, or heteroarylalkyl; $R^2$ is hydrogen or alkyl; R is hydrogen or alkyl; and each of $R^{10}$, $R^{11}$, and $R^{12}$ is independently hydrogen or alkyl; or $R^{10}$ and $R^{11}$, together with the carbon atoms to which they are attached, combine to form a five-, six-, or seven-membered ring.

In certain embodiments, provided herein are compounds according to Formula 1002:

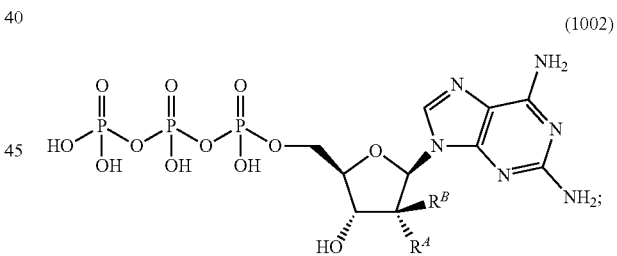

(1002)

or a pharmaceutically acceptable salt, solvate, stereoisomeric form, tautomeric form, or polymorphic form thereof, wherein: $R^A$ is hydroxyl or halo; and $R^B$ is methyl or halo.

In some embodiments, provided herein are:
(a) compounds as described herein, e.g., of Formula 2001, 2001, I-XXIX, 1-23byii and 1001-1002, and pharmaceutically acceptable salts and compositions thereof;
(b) compounds as described herein, e.g., of Formula 2001, I-XXIX, 1-23byii and 1001-1002, and pharmaceutically acceptable salts and compositions thereof for use in the treatment and/or prophylaxis of a liver disorder including Flaviviridae infection, especially in individuals diagnosed as having a Flaviviridae infection or being at risk of becoming infected by hepatitis C;
(c) processes for the preparation of compounds as described herein, e.g., of Formula 2001, I-XXIX, 1-23byii and 1001-1002, as described in more detail elsewhere herein;

(d) pharmaceutical formulations comprising a compound as described herein, e.g., of Formula 2001, I-XXIX, 1-23byii and 1001-1002, or a pharmaceutically acceptable salt thereof together with a pharmaceutically acceptable carrier or diluent;

(e) pharmaceutical formulations comprising a compound as described herein, e.g., of Formula 2001, I-XXIX, 1-23byii and 1001-1002, or a pharmaceutically acceptable salt thereof together with one or more other effective anti-HCV agents, optionally in a pharmaceutically acceptable carrier or diluent;

(f) a method for the treatment and/or prophylaxis of a host infected with Flaviviridae that includes the administration of an effective amount of a compound as described herein, e.g., of Formula 2001, I-XXIX, 1-23byii and 1001-1002, its pharmaceutically acceptable salt or composition; or (g) a method for the treatment and/or prophylaxis of a host infected with Flaviviridae that includes the administration of an effective amount of a compounds as described herein, e.g., of Formula 2001, I-XXIX, 1-23byii and 1001-1002, its pharmaceutically acceptable salt or composition in combination and/or alternation with one or more effective anti-HCV agent.

Optically Active Compounds

It is appreciated that compounds provided herein have several chiral centers and may exist in and be isolated in optically active and racemic forms. Some compounds may exhibit polymorphism. It is to be understood that any racemic, optically-active, diastereomeric, polymorphic, or stereoisomeric form, or mixtures thereof, of a compound provided herein, which possess the useful properties described herein is within the scope of the invention. It being well known in the art how to prepare optically active forms (for example, by resolution of the racemic form by recrystallization techniques, by synthesis from optically-active starting materials, by chiral synthesis, or by chromatographic separation using a chiral stationary phase).

In particular, since the 1' and 4' carbons of a nucleoside are chiral, their non-hydrogen substituents (the base and the CHOR groups, respectively) can be either cis (on the same side) or trans (on opposite sides) with respect to the sugar ring system. The four optical isomers therefore are represented by the following configurations (when orienting the sugar moiety in a horizontal plane such that the oxygen atom is in the back): cis (with both groups "up", which corresponds to the configuration of naturally occurring β-D nucleosides), cis (with both groups "down", which is a non-naturally occurring β-L configuration), trans (with the C2' substituent "up" and the C4' substituent "down"), and trans (with the C2' substituent "down" and the C4' substituent "up"). The "D-nucleosides" are cis nucleosides in a natural configuration and the "L-nucleosides" are cis nucleosides in the non-naturally occurring configuration.

Likewise, most amino acids are chiral (designated as L or D, wherein the L enantiomer is the naturally occurring configuration) and can exist as separate enantiomers.

Examples of methods to obtain optically active materials are known in the art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

In some embodiments, provided is a composition of a thiophosphate nucleoside compound that comprises a substantially pure designated enantiomer of the thiophosphate nucleoside compound. In certain embodiments, in the methods and compounds of this invention, the compounds are substantially free of other enantiomers. In some embodiments, a composition includes a compound that is at least 85%, 90%, 95%, 98%, 99%, or 100% by weight, of the compound, the remainder comprising other chemical species or enantiomers.

Isotopically Enriched Compounds

Also provided herein are isotopically enriched compounds, including but not limited to isotopically enriched thiophosphate nucleoside compounds.

Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrees the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g., Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators, and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable KIE that will affect the pharmacokinetic, pharmacologic, and/or toxicological profiles of a compound provided herein in comparison with a similar compound having a natural isotopic composition.

Preparation of Compounds

The compounds provided herein can be prepared, isolated, or obtained by any method apparent to those of skill in the art. Compounds provided herein can be prepared according to the Exemplary Preparation Scheme provided below. Reaction conditions, steps, and reactants not provided in the Exemplary Preparation Scheme would be apparent to, and known by, those skilled in the art.

Exemplary Preparation Schemes

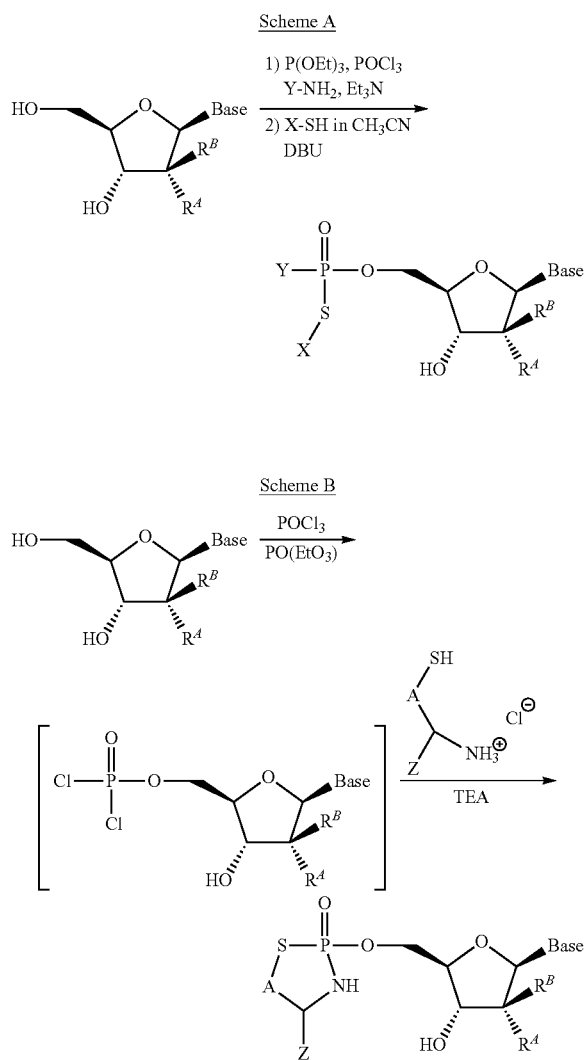

In the Exemplary Preparation Schemes, Base, $R^A$, $R^B$, X, Y, Z and A are as described in the context of Formula I or 2001. Additional steps and reagents not provided in the Exemplary Preparation Schemes would be known to those of skill in the art. Exemplary methods of preparation are described in detail in the Examples herein.

Pharmaceutical Compositions and Methods of Administration

Thiophosphate nucleoside compounds can be formulated into pharmaceutical compositions using methods available in the art and those disclosed herein. Any of the compounds disclosed herein can be provided in the appropriate pharmaceutical composition and be administered by a suitable route of administration.

The methods provided herein encompass administering pharmaceutical compositions containing at least one compound as described herein, including a compound of general Formula 2001, I-XXIX, 1-23byii and 1001-1002, if appropriate in the salt form, either used alone or in the form of a combination with one or more compatible and pharmaceutically acceptable carriers, such as diluents or adjuvants, or with another anti-HCV agent.

In certain embodiments, the second agent can be formulated or packaged with the compound provided herein. Of course, the second agent will only be formulated with the compound provided herein when, according to the judgment of those of skill in the art, such co-formulation should not interfere with the activity of either agent or the method of administration. In certain embodiments, the compound provided herein and the second agent are formulated separately. They can be packaged together, or packaged separately, for the convenience of the practitioner of skill in the art.

In clinical practice the active agents provided herein may be administered by any conventional route, in particular orally, parenterally, rectally or by inhalation (e.g. in the form of aerosols). In certain embodiments, the compound provided herein is administered orally.

Use may be made, as solid compositions for oral administration, of tablets, pills, hard gelatin capsules, powders or granules. In these compositions, the active product is mixed with one or more inert diluents or adjuvants, such as sucrose, lactose, or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups, and elixirs containing inert diluents, such as water or liquid paraffin. These compositions can also comprise substances other than diluents, for example wetting, sweetening, or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing, and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides, or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, for example, in the U.S. Pharmocopia (USP) SP (XXI)/NF (XVI). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, New York, 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, for example, an animal subject, such as a mammalian subject, for example, a human subject.

A pharmaceutical composition is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intratumoral, intra-synovial, and rectal administration. In a specific embodiment, the composition is formulated in accordance with routine procedures as a pharmaceutical composition adapted for intravenous, subcutaneous, intramuscular, oral, intranasal, or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. For example, a dosage form used in the initial treatment of viral infection may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington's Pharmaceutical Sciences, 20th ed., Mack Publishing, Easton Pa. (2000).

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500, or 1000 mg of the active compound.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 20th ed., Mack Publishing, Easton Pa. (2000).

In certain embodiments, the oral dosage forms are solid and prepared under anhydrous conditions with anhydrous ingredients, as described in detail herein. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; each of which is incorporated herein by reference in its entirety. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompassed herein are single unit dosage forms suitable for oral administration such as, but not limited to, tablets, capsules, gelcaps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In certain embodiments, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16$^{th}$, 18th and 20$^{th}$ eds., Mack Publishing, Easton Pa. (1980, 1990 & 2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are nontoxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, $16^{th}$, 18th and $20^{th}$ eds., Mack Publishing, Easton Pa. (1980, 1990 & 2000).

Depending on the specific tissue to be treated, additional components may be used prior to, in conjunction with, or subsequent to treatment with active ingredients provided. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates, or solvates of the active ingredients can be used to further adjust the properties of the resulting composition.

Dosage and Unit Dosage Forms

In human therapeutics, the doctor will determine the posology which he considers most appropriate according to a preventive or curative treatment and according to the age, weight, stage of the infection and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

In further aspects, provided are methods of treating or preventing an HCV infection in a subject by administering, to a subject in need thereof, an effective amount of a compound provided herein, or a pharmaceutically acceptable salt thereof. The amount of the compound or composition which will be effective in the prevention or treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.20 mg/kg and 2.00 mg/kg, or between 0.30 mg/kg and 1.50 mg/kg of the subject's body weight.

In certain embodiments, the recommended daily dose range of a composition provided herein for the conditions described herein lie within the range of from about 0.1 mg to about 1000 mg per day, given as a single once-a-day dose or as divided doses throughout a day. In certain embodiments, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiment, the dosage of the composition provided herein, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of a compound or composition provided herein followed by one or more maintenance doses. In such embodiments, the loading dose can be, for instance, about 60 to about 400 mg per day, or about 100 to about 200 mg per day for one day to five weeks. The loading dose can be followed by one or more maintenance doses. In certain embodiments, each maintenance does is, independently, about from about 10 mg to about 200 mg per day, between about 25 mg and about 150 mg per day, or between about 25 and about 80 mg per day. Maintenance doses can be administered daily and can be administered as single doses, or as divided doses.

In certain embodiments, a dose of a compound or composition provided herein can be administered to achieve a steady-state concentration of the active ingredient in blood or serum of the subject. The steady-state concentration can be determined by measurement according to techniques available to those of skill or can be based on the physical characteristics of the subject such as height, weight, and age. In certain embodiments, a sufficient amount of a compound or composition provided herein is administered to achieve a steady-state concentration in blood or serum of the subject of from about 300 to about 4000 ng/mL, from about 400 to about 1600 ng/mL, or from about 600 to about 1200 ng/mL. In some embodiments, loading doses can be administered to achieve steady-state blood or serum concentrations of about 1200 to about 8000 ng/mL, or about 2000 to about 4000 ng/mL for one to five days. In certain embodiments, maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, provided herein are unit dosages comprising a compound, or a pharmaceutically acceptable salt thereof, in a form suitable for administration. Such forms are described in detail herein. In certain embodiments, the unit dosage comprises 1 to 1000 mg, 5 to 250 mg, or 10 to 50 mg active ingredient. In particular embodiments, the unit dosages comprise about 1, 5, 10, 25, 50, 100, 125, 250, 500, or 1000 mg active ingredient. Such unit dosages can be prepared according to techniques familiar to those of skill in the art.

The dosages of the second agents are to be used in the combination therapies provided herein. In certain embodiments, dosages lower than those which have been or are currently being used to prevent or treat HCV infection are used in the combination therapies provided herein. The recommended dosages of second agents can be obtained from the knowledge of those of skill. For those second agents that are approved for clinical use, recommended dosages are described in, for example, Hardman et al., eds., 1996, Goodman & Gilman's The Pharmacological Basis Of Basis Of Therapeutics 9$^{th}$ Ed, Mc-Graw-Hill, New York; Physician's Desk Reference (PDR) 57$^{th}$ Ed., 2003, Medical Economics Co., Inc., Montvale, N.J., which are incorporated herein by reference in its entirety.

In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In various embodiments, the therapies are administered no more than 24 hours apart or no more than 48 hours apart. In certain embodiments, two or more therapies are administered within the same patient visit. In other embodiments, the compound provided herein and the second agent are administered concurrently.

In other embodiments, the compound provided herein and the second agent are administered at about 2 to 4 days apart, at about 4 to 6 days apart, at about 1 week part, at about 1 to 2 weeks apart, or more than 2 weeks apart.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, a compound provided herein and a second agent are administered to a patient, for example, a mammal, such as a human, in a sequence and within a time interval such that the compound provided herein can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In certain embodiments, the compound provided herein and the second active agent exert their effect at times which overlap. Each second active agent can be administered separately, in any appropriate form and by any suitable route. In other embodiments, the compound provided herein is administered before, concurrently or after administration of the second active agent.

In certain embodiments, the compound provided herein and the second agent are cyclically administered to a patient. Cycling therapy involves the administration of a first agent (e.g., a first prophylactic or therapeutic agents) for a period of time, followed by the administration of a second agent and/or third agent (e.g., a second and/or third prophylactic or therapeutic agents) for a period of time and repeating this sequential administration. Cycling therapy can reduce the development of resistance to one or more of the therapies, avoid or reduce the side effects of one of the therapies, and/or improve the efficacy of the treatment.

In certain embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the compound provided herein can work together with the second active agent. For example, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound provided herein. In certain embodiments, the compound provided herein is administered concurrently with one or more second agents in the same pharmaceutical composition. In another embodiment, a compound provided herein is administered concurrently with one or more second agents in separate pharmaceutical compositions. In still another embodiment, a compound provided herein is administered prior to or subsequent to administration of a second agent. Also contemplated are administration of a compound provided herein and a second agent by the same or different routes of administration, e.g., oral and parenteral. In certain embodiments, when the compound provided herein is administered concurrently with a second agent that potentially produces adverse side effects including, but not limited to, toxicity, the second active agent can advantageously be administered at a dose that falls below the threshold that the adverse side effect is elicited.

Kits

Also provided are kits for use in methods of treatment of a liver disorder such as HCV infections. The kits can include a compound or composition provided herein, a second agent or composition, and instructions providing information to a health care provider regarding usage for treating the disorder. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 days. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Methods of Use

Provided herein is a method for inhibiting replication of a virus in a host, which comprises contacting the host with a therapeutically effective amount of a thiophosphate nucleoside disclosed herein, e.g., a thiophosphate nucleoside compound of Formula 2001, I-XXIX, 1-23byii and 1001-1002, including a single enantiomer, a mixture of an enantiomeric pair, an individual diastereomer, a mixture of diastereomers, or a tautomeric form thereof or a pharmaceutically acceptable salt, solvate, prodrug, phosphate, or active metabolite thereof.

Provided herein is a method for inhibiting replication of a virus in a cell, which comprises contacting the cell with a therapeutically effective amount of a thiophosphate nucleoside compound disclosed herein, e.g., a thiophosphate nucleoside compound of Formula 2001, I-XXIX, 1-23byii and 1001-1002, including a single enantiomer, a mixture of an enantiomeric pair, an individual diastereomer, a mixture of diastereomers, or a tautomeric form thereof; or a pharmaceutically acceptable salt, solvate, prodrug, phosphate, or active metabolite thereof.

Provided herein is a method for inhibiting replication of a virus, which comprises contacting the virus with a therapeutically effective amount of a thiophosphate nucleoside compound disclosed herein, e.g., a thiophosphate nucleoside compound of Formula 2001, I-XXIX, 1-23byii and 1001-1002, including a single enantiomer, a mixture of an enantiomeric pair, an individual diastereomer, a mixture of diastereomers, or a tautomeric form thereof; or a pharmaceutically acceptable salt, solvate, prodrug, phosphate, or active metabolite thereof.

Provided herein is a method for inhibiting the activity of a polymerase, which comprises contacting the polymerase with a ester or malonate of a thiophosphate nucleoside compound disclosed herein, e.g., a thiophosphate nucleoside compound of Formula 2001, I-XXIX, 1-23byii and 1001-1002, including a single enantiomer, a mixture of an enantiomeric pair, an individual diastereomer, a mixture of diastereomers, or a tautomeric form thereof; or a pharmaceutically acceptable salt, solvate, prodrug, phosphate, or active metabolite thereof.

In certain embodiments, provided herein are methods for the treatment and/or prophylaxis of a host infected with Flaviviridae that includes the administration of an effective amount of a thiophosphate nucleoside compound disclosed herein, e.g., a thiophosphate nucleoside compound of Formula 2001, I-XXIX, 1-23byii and 1001-1002, including a single enantiomer, a mixture of an enantiomeric pair, an individual diastereomer, a mixture of diastereomers, or a tautomeric form thereof; or a pharmaceutically acceptable salt, solvate, prodrug, phosphate, or active metabolite thereof.

In certain embodiments, provided herein are methods for treating an HCV infection in a subject. In certain embodiments, the methods encompass the step of administering to a subject in need thereof an amount of a compound effective for the treatment or prevention of an HCV infection in combination with a second agent effective for the treatment or prevention of the infection. The compound can be any compound as described herein, and the second agent can be any second agent described in the art or herein. In certain embodiments, the compound is in the form of a pharmaceutical composition or dosage form, as described elsewhere herein.

In certain embodiments, provided herein are methods for the treatment and/or prophylaxis of a host infected with Flaviviridae that includes the administration of an effective amount of a compounds provided herein, or a pharmaceutically acceptable salt thereof. In certain embodiments, provided herein are methods for treating an HCV infection in a subject. In certain embodiments, the methods encompass the step of administering to a subject in need thereof an amount of a compound effective for the treatment or prevention of an HCV infection in combination with a second agent effective for the treatment or prevention of the infection. The compound can be any compound as described herein, and the second agent can be any second agent described in the art or herein. In certain embodiments, the compound is in the form of a pharmaceutical composition or dosage form, as described elsewhere herein.

Flaviviridae which can be treated are, e.g., discussed generally in *Fields Virology*, Fifth Ed., Editors: Knipe, D. M., and Howley, P. M., Lippincott Williams & Wilkins Publishers, Philadelphia, Pa., Chapters 33-35, 2006. In a particular embodiment of the invention, the Flaviviridae is HCV. In an alternate embodiment, the Flaviviridae is a flavivirus or pestivirus. In certain embodiments, the Flaviviridae can be from any class of Flaviviridae. In certain embodiments, the Flaviviridae is a mammalian tick-borne virus. In certain embodiments, the Flaviviridae is a seabird tick-borne virus. In certain embodiments, the Flaviviridae is a mosquito-borne virus. In certain embodiments, the Flaviviridae is an Aroa virus. In certain embodiments, the Flaviviridae is a Dengue virus. In certain embodiments, the Flaviviridae is a Japanese encephalitis virus. In certain embodiments, the Flaviviridae is a Kokobera virus. In certain embodiments, the Flaviviridae is a Ntaya virus. In certain embodiments, the Flaviviridae is a Spondweni virus. In certain embodiments, the Flaviviridae is a Yellow fever virus. In certain embodiments, the Flaviviridae is a Entebbe virus. In certain embodiments, the Flaviviridae is a Modoc virus. In certain embodiments, the Flaviviridae is a Rio Bravo virus.

Specific flaviviruses which can be treated include, without limitation: Absettarov, Aedes, Alfuy, Alkhurma, Apoi, Aroa, Bagaza, Banzi, Bukalasa bat, Bouboui, Bussuquara, Cacipacore, Calbertado, Carey Island, Cell fusing agent, Cowbone Ridge, Culex, Dakar bat, Dengue 1, Dengue 2, Dengue 3, Dengue 4, Edge Hill, Entebbe bat, Gadgets Gully, Hanzalova, Hypr, Ilheus, Israel turkey meningoencephalitis, Japanese encephalitis, Jugra, Jutiapa, Kadam, Kamiti River, Karshi, Kedougou, Kokobera, Koutango, Kumlinge, Kunjin, Kyasanur Forest disease, Langat, Louping ill, Meaban, Modoc, Montana myotis leukoencephalitis, Murray valley encephalitis, Nakiwogo, Naranjal, Negishi, Ntaya, Omsk hemorrhagic fever, Phnom-Penh bat, Powassan, Quang Binh, Rio Bravo, Rocio, Royal Farm, Russian spring-summer encephalitis, Saboya, St. Louis encephalitis, Sal Vieja, San Perlita, Saumarez Reef, Sepik, Sokuluk, Spondweni, Stratford, Tembusu, Tick-borne encephalitis, Turkish sheep encephalitis, Tyuleniy, Uganda S, Usutu, Wesselsbron, West Nile, Yaounde, Yellow fever, Yokose, and Zika.

Pestiviruses which can be treated are discussed generally in *Fields Virology*, Fifth Ed., Editors: Knipe, D. M., and Howley, P. M., Lippincott Williams & Wilkins Publishers, Philadelphia, Pa., Chapters 33-35, 2006. Specific pestiviruses which can be treated include, without limitation: bovine viral diarrhea virus ("BVDV"), classical swine fever virus ("CSFV," also called hog cholera virus), and border disease virus ("BDV").

In certain embodiments, the subject can be any subject infected with, or at risk for infection with, HCV. Infection or risk for infection can be determined according to any technique deemed suitable by the practitioner of skill in the art. In certain embodiments, subjects are humans infected with HCV.

In certain embodiments, the subject has never received therapy or prophylaxis for an HCV infection. In further embodiments, the subject has previously received therapy or prophylaxis for an HCV infection. For instance, in certain embodiments, the subject has not responded to an HCV therapy. For example, under current interferon therapy, up to 50% or more HCV subjects do not respond to therapy. In certain embodiments, the subject can be a subject that received therapy but continued to suffer from viral infection or one or more symptoms thereof. In certain embodiments, the subject can be a subject that received therapy but failed to achieve a sustained virologic response. In certain embodiments, the subject has received therapy for an HCV infection but has failed to show, for example, a 2 $\log_{10}$ decline in HCV RNA levels after 12 weeks of therapy. It is believed that subjects who have not shown more than 2 $\log_{10}$ reduction in serum HCV RNA after 12 weeks of therapy have a 97-100% chance of not responding.

In certain embodiments, the subject is a subject that discontinued an HCV therapy because of one or more adverse events associated with the therapy. In certain embodiments, the subject is a subject where current therapy is not indicated. For instance, certain therapies for HCV are associated with neuropsychiatric events. Interferon (IFN)-alfa plus ribavirin is associated with a high rate of depression. Depressive symptoms have been linked to a worse outcome in a number of medical disorders. Life-threatening or fatal neuropsychiatric events, including suicide, suicidal and homicidal ideation, depression, relapse of drug addiction/overdose, and aggressive behavior have occurred in subjects with and without a previous psychiatric disorder during HCV therapy. Interferon-induced depression is a limitation for the treatment of chronic hepatitis C, especially for subjects with psychiatric disorders. Psychiatric side effects are common with interferon therapy and responsible for about 10% to 20% of discontinuations of current therapy for HCV infection.

Accordingly, provided are methods of treating or preventing an HCV infection in subjects where the risk of neuropsychiatric events, such as depression, contraindicates treatment with current HCV therapy. In certain embodiments, provided are methods of treating or preventing HCV infection in subjects where a neuropsychiatric event, such as depression, or risk of such indicates discontinuation of treatment with current HCV therapy. Further provided are methods of treating or preventing HCV infection in subjects where a neuropsychiatric event, such as depression, or risk of such indicates dose reduction of current HCV therapy.

Current therapy is also contraindicated in subjects that are hypersensitive to interferon or ribavirin, or both, or any other component of a pharmaceutical product for administration of interferon or ribavirin. Current therapy is not indicated in subjects with hemoglobinopathies (e.g., thalassemia major, sickle-cell anemia) and other subjects at risk from the hematologic side effects of current therapy. Common hematologic side effects include bone marrow suppression, neutropenia, and thrombocytopenia. Furthermore, ribavirin is toxic to red blood cells and is associated with hemolysis. Accordingly, in certain embodiments, provided are methods of treating or preventing HCV infection in subjects hypersensitive to interferon or ribavirin, or both, subjects with a hemoglobinopathy, for instance thalassemia major subjects and sickle-cell anemia subjects, and other subjects at risk from the hematologic side effects of current therapy.

In certain embodiments, the subject has received an HCV therapy and discontinued that therapy prior to administration of a method provided herein. In further embodiments, the subject has received therapy and continues to receive that therapy along with administration of a method provided herein. The methods can be co-administered with other therapy for HBC and/or HCV according to the judgment of one of skill in the art. In certain embodiments, the methods or compositions provided herein can be co-administered with a reduced dose of the other therapy for HBC and/or HCV.

In certain embodiments, provided are methods of treating a subject that is refractory to treatment with interferon. For instance, in some embodiments, the subject can be a subject that has failed to respond to treatment with one or more agents, wherein the one or more agents are an interferon, interferon α, pegylated interferon α, interferon plus ribavirin, interferon α plus ribavirin, and/or pegylated interferon α plus ribavirin. In some embodiments, the subject can be a subject that has responded poorly to treatment with one or more agents, wherein the one or more agents are interferon, interferon α, pegylated interferon α, interferon plus ribavirin, interferon α plus ribavirin, and/or pegylated interferon α plus ribavirin. A pro-drug form of ribavirin, such as taribavirin, may also be used.

In certain embodiments, the subject has, or is at risk for, co-infection of HCV with HIV. For instance, in the United States, 30% of HIV subjects are co-infected with HCV and evidence indicates that people infected with HIV have a much more rapid course of their hepatitis C infection. Maier and Wu, 2002, *World J Gastroenterol* 8:577-57. The methods provided herein can be used to treat or prevent HCV infection in such subjects. It is believed that elimination of HCV in these subjects will lower mortality due to end-stage liver disease. Indeed, the risk of progressive liver disease is higher in subjects with severe AIDS-defining immunodeficiency than in those without. See, e.g., Lesens et al., 1999, *J Infect Dis* 179:1254-1258. In certain embodiments, compounds provided herein have been shown to suppress HIV in HIV subjects. Thus, in certain embodiments, provided are methods of treating or preventing HIV infection and HCV infection in subjects in need thereof.

In certain embodiments, the compounds or compositions are administered to a subject following liver transplant. Hepatitis C is a leading cause of liver transplantation in the U.S., and many subjects that undergo liver transplantation remain HCV positive following transplantation. In certain embodiments, provided are methods of treating such recurrent HCV subjects with a compound or composition provided herein. In certain embodiments, provided are methods of treating a subject before, during or following liver transplant to prevent recurrent HCV infection.

Assay Methods

Compounds can be assayed for HCV activity according to any assay known to those of skill in the art.

Further, compounds can be assayed for accumulation in liver cells of a subject according to any assay known to those of skill in the art. In certain embodiments, a compound can be administered to the subject, and a liver cell of the subject can be assayed for the compound or a derivative thereof, e.g. a nucleoside, nucleoside phosphate or nucleoside triphosphate derivative thereof.

In certain embodiments, a thiophosphate nucleoside compound is administered to cells, such as liver cells, in vivo or in vitro, and the nucleoside triphosphate levels delivered intracellularly are measured, to indicate delivery of the compound and triphosphorylation in the cell. The levels of intracellular nucleoside triphosphate can be measured using analytical techniques known in the art. Methods of detecting ddATP are described herein below by way of example, but other nucleoside triphosphates can be readily detected using the appropriate controls, calibration samples, and assay techniques.

In certain embodiments, ddATP concentrations are measured in a sample by comparison to calibration standards made from control samples. The ddATP concentrations in a sample can be measured using an analytical method such as HPLC LC MS. In certain embodiments, a test sample is compared to a calibration curve created with known concentrations of ddATP to thereby obtain the concentration of that sample.

In certain embodiments, the samples are manipulated to remove impurities such as salts ($Na^+$, $K^+$, etc.) before analysis. In certain embodiments, the lower limit of quantitation is about ~0.2 pmol/mL for hepatocyte cellular extracts particularly where reduced salt is present.

In certain embodiments, the method allows successfully measuring triphosphate nucleotides formed at levels of 1-10,000 pmol per million cells in e.g. cultured hepatocytes and HepG2 cells.

Second Therapeutic Agents

In certain embodiments, the compounds and compositions provided herein are useful in methods of treatment of a liver disorder, that comprise further administration of a second agent effective for the treatment of the disorder, such as HCV infection in a subject in need thereof. The second agent can be any agent known to those of skill in the art to be effective for the treatment of the disorder, including those currently approved by the FDA.

In certain embodiments, a compound provided herein is administered in combination with one second agent. In further embodiments, a second agent is administered in combination with two second agents. In still further embodiments, a second agent is administered in combination with two or more second agents.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage, or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The active compounds provided herein can be administered in combination or alternation with another therapeutic agent, in particular an anti-HCV agent. In combination therapy, effective dosages of two or more agents are administered together, whereas in alternation or sequential-step therapy, an effective dosage of each agent is administered serially or sequentially. The dosages given will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. In certain embodiments, an anti-HCV (or anti-pestivirus or anti-flavivirus) compound that exhibits an $EC_{50}$ of 10-15 µM. In certain embodiments, less than 1-5 µM, is desirable.

It has been recognized that drug-resistant variants of flaviviruses, pestiviruses, or HCV can emerge after prolonged treatment with an antiviral agent. Drug resistance most typically occurs by mutation of a gene that encodes for an enzyme used in viral replication. The efficacy of a drug against the viral infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

Any of the viral treatments described in the Background of the Invention can be used in combination or alternation with the compounds described in this specification. Non-limiting examples of second agents include:

HCV Protease inhibitors: Examples include Medivir HCV Protease Inhibitor simeprevir (HCV-PI or TMC435) (Medivir/Tibotec); MK-7009 (Merck), RG7227 (ITMN-191) (Roche/Pharmasset/InterMune), boceprevir (SCH 503034) (Schering), SCH 446211 (Schering), narlaprevir SCH900518 (Schering/Merck), ABT-450 (Abbott/Enanta), ACH-1625 (Achillion), BI 201335 (Boehringer Ingelheim), PHX1766 (Phenomix), VX-500 (Vertex) and telaprevir (VX-950) (Vertex). Further examples of protease inhibitors include substrate-based NS3 protease inhibitors (Attwood et al., Antiviral peptide derivatives, PCT WO 98/22496, 1998; Attwood et al., *Antiviral Chemistry and Chemotherapy* 1999, 10, 259-273; Attwood et al., Preparation and use of amino acid derivatives as anti-viral agents, German Patent Pub. DE 19914474; Tung et al., Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (Llinas-Brunet et al, Hepatitis C inhibitor peptide analogues, PCT WO 99/07734); Non-substrate-based NS3 protease inhibitors such as 2,4,6-trihydroxy-3-nitro-benzamide derivatives (Sudo K. et al., *Biochemical and Biophysical Research Communications*, 1997, 238, 643-647; Sudo K. et al., *Antiviral Chemistry and Chemotherapy*, 1998, 9, 186), including RD3-4082 and RD3-4078, the former substituted on the amide with a 14 carbon chain and the latter processing a para-phenoxyphenyl group; and Sch 68631, a phenanthrenequinone, an HCV protease inhibitor (Chu M. et al., *Tetrahedron Letters* 37:7229-7232, 1996).

SCH 351633, isolated from the fungus *Penicillium griseofulvum*, was identified as a protease inhibitor (Chu M. et al., *Bioorganic and Medicinal Chemistry Letters* 9:1949-1952). Eglin c, isolated from leech, is a potent inhibitor of several serine proteases such as *S. griseus* proteases A and B, α-chymotrypsin, chymase and subtilisin. Qasim M. A. et al., *Biochemistry* 36:1598-1607, 1997.

U.S. patents disclosing protease inhibitors for the treatment of HCV include, for example, U.S. Pat. No. 6,004,933 to Spruce et al., which discloses a class of cysteine protease inhibitors for inhibiting HCV endopeptidase 2; U.S. Pat. No. 5,990,276 to Zhang et al., which discloses synthetic inhibitors of hepatitis C virus NS3 protease; U.S. Pat. No. 5,538,865 to Reyes et a; WO 02/008251 to Corvas International, Inc., and U.S. Pat. No. 7,169,760, US2005/176648, WO 02/08187 and WO 02/008256 to Schering Corporation. HCV inhibitor tripeptides are disclosed in U.S. Pat. Nos. 6,534,523, 6,410,531, and U.S. Pat. No. 6,420,380 to Boehringer Ingelheim and WO 02/060926 to Bristol Myers Squibb. Diaryl peptides as NS3 serine protease inhibitors of HCV are disclosed in WO 02/48172 and U.S. Pat. No. 6,911,428 to Schering Corporation. Imidazoleidinones as NS3 serine protease inhibitors of HCV are disclosed in WO 02/08198 and U.S. Pat. No. 6,838, 475 to Schering Corporation and WO 02/48157 and U.S. Pat. No. 6,727,366 to Bristol Myers Squibb. WO 98/17679 and U.S. Pat. No. 6,265,380 to Vertex Pharmaceuticals and WO 02/48116 and U.S. Pat. No. 6,653,295 to Bristol Myers Squibb also disclose HCV protease inhibitors. Further examples of HCV serine protease inhibitors are provided in U.S. Pat. No. 6,872,805 (Bristol-Myers Squibb); WO 2006000085 (Boehringer Ingelheim); U.S. Pat. No. 7,208, 600 (Vertex); US 2006/0046956 (Schering-Plough); WO 2007/001406 (Chiron); US 2005/0153877; WO 2006/119061 (Merck); WO 00/09543 (Boehringer Ingelheim), U.S. Pat. No. 6,323,180 (Boehringer Ingelheim) WO 03/064456 (Boehringer Ingelheim), U.S. Pat. No. 6,642,204 (Boehringer Ingelheim), WO 03/064416 (Boehringer Ingelheim), U.S. Pat. No. 7,091,184 (Boehringer Ingelheim), WO 03/053349 (Bristol-Myers Squibb), U.S. Pat. No. 6,867,185, WO 03/099316 (Bristol-Myers Squibb), U.S. Pat. No. 6,869,964, WO 03/099274 (Bristol-Myers Squibb), U.S. Pat. No. 6,995, 174, WO 2004/032827 (Bristol-Myers Squibb), U.S. Pat. No. 7,041,698, WO 2004/043339 and U.S. Pat. No. 6,878,722 (Bristol-Myers Squibb).

Thiazolidine derivatives which show relevant inhibition in a reverse-phase HPLC assay with an NS3/4A fusion protein and NS5A/5B substrate (Sudo K. et al., *Antiviral Research*, 1996, 32, 9-18), especially compound RD-1-6250, possessing a fused cinnamoyl moiety substituted with a long alkyl chain, RD4 6205 and RD4 6193;

Thiazolidines and benzanilides identified in Kakiuchi N. et al., J. EBS Letters 421, 217-220; Takeshita N. et al., *Analytical Biochemistry*, 1997, 247, 242-246;

A phenanthrenequinone possessing activity against protease in a SDS-PAGE and autoradiography assay isolated from the fermentation culture broth of *Streptomyces* sp., SCH 68631 (Chu M. et al., *Tetrahedron Letters*, 1996, 37, 7229-7232), and SCH 351633, isolated from the fungus *Penicillium griseofulvum*, which demonstrates activity in a scintillation proximity assay (Chu M. et al., *Bioorganic and Medicinal Chemistry Letters* 9, 1949-1952);

Helicase inhibitors (Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

HCV polymerase inhibitors, including nucleoside and non-nucleoside polymerase inhibitors, such as ribavirin, viramidine, clemizole, filibuvir (PF-00868554), HCV POL, NM 283 (valopicitabine), MK-0608, 7-Fluoro-MK-0608, MK-3281, IDX-375, ABT-072, ABT-333, 0 598, BI 207127, GS 9190, PSI-6130, R1626, PSI-6206, PSI-938, PSI-7851, PSI-7977 (sofosbuvir, Sovaldi), RG1479, RG7128, HCV-796 VCH-759 or VCH-916;

Gliotoxin (Ferrari R. et al., *Journal of Virology*, 1999, 73, 1649-1654), and the natural product cerulenin (Lohmann V. et al., *Virology*, 1998, 249, 108-118);

Interfering RNA (iRNA) based antivirals, including short interfering RNA (siRNA) based antivirals, such as Sirna-034 and others described in International Patent Publication Nos. WO/03/070750 and WO 2005/012525, and US Patent Publication No. US 2004/0209831;

HCV NS5A inhibitors, such as BMS-790052 (daclatasvir, Bristol-Myers Squibb), PPI-461 (Presidio Pharmaceuticals), PPI-1301 (Presidio Pharmaceuticals), IDX-719 (samatasvir, Idenix Pharmaceuticals), AZD7295 (Arrow Therapeutics, AstraZeneca), EDP-239 (Enanta), ACH-2928 (Achillion), ACH-3102 (Achillion), ABT-267 (Abbott), or GS-5885 (Gilead);

Antisense phosphorothioate oligodeoxynucleotides (S-ODN) complementary to sequence stretches in the 5' non-coding region (NCR) of the virus (Alt M. et al., *Hepatology*, 1995, 22, 707-717), or nucleotides 326-348 comprising the 3' end of the NCR and nucleotides 371-388 located in the core coding region of the HCV RNA (Alt M. et al., *Archives of Virology*, 1997, 142, 589-599; Galderisi U. et al., *Journal of Cellular Physiology*, 1999, 181, 251-257);

Inhibitors of IRES-dependent translation (Ikeda N et al., Agent for the prevention and treatment of hepatitis C, Japanese Patent Pub. JP-08268890; Kai Y. et al., Prevention and treatment of viral diseases, Japanese Patent Pub. JP-10101591);

HCV entry inhibitors, such as celgosivir (MK-3253) (MI-GENIX Inc.), SP-30 (Samaritan Pharmaceuticals), ITX4520 (iTherX), ITX5061 (iTherX), PRO-206 (Progenics Pharmaceuticals) and other entry inhibitors by Progenics Pharmaceuticals, e.g., as disclosed in U.S. Patent Publication No. 2006/0198855.

Ribozymes, such as nuclease-resistant ribozymes (Maccjak, D. J. et al., *Hepatology* 1999, 30, abstract 995) and those disclosed in U.S. Pat. No. 6,043,077 to Barber et al., and U.S. Pat. Nos. 5,869,253 and 5,610,054 to Draper et al.; and Nucleoside analogs have also been developed for the treatment of Flaviviridae infections.

In certain embodiments, the compounds provided herein can be administered in combination with any of the compounds described by Idenix Pharmaceuticals in International Publication Nos. WO 01/90121, WO 01/92282, WO 2004/003000, WO 2004/002422 and WO 2004/002999.

Other patent applications disclosing the use of certain nucleoside analogs that can be used as second agents to treat hepatitis C virus include: PCT/CA00/01316 (WO 01/32153; filed Nov. 3, 2000) and PCT/CA01/00197 (WO 01/60315; filed Feb. 19, 2001) filed by BioChem Pharma, Inc. (now Shire Biochem, Inc.); PCT/US02/01531 (WO 02/057425; filed Jan. 18, 2002); PCT/US02/03086 (WO 02/057287; filed Jan. 18, 2002); U.S. Pat. Nos. 7,202,224; 7,125,855; 7,105, 499; and 6,777,395 by Merck & Co., Inc.; PCT/EP01/09633 (WO 02/18404; published Aug. 21, 2001); US 2006/0040890; 2005/0038240; 2004/0121980; 6,846,810; 6,784, 166; and 6,660,721 by Roche; PCT Publication Nos. WO 01/79246 (filed Apr. 13, 2001), WO 02/32920 (filed Oct. 18, 2001) and WO 02/48165; US 2005/0009737; US 2005/0009737; 7,094,770; and 6,927,291 by Pharmasset, Ltd.

Further compounds that can be used as second agents to treat hepatitis C virus are disclosed in PCT Publication No. WO 99/43691 to Emory University, entitled "2'-Fluoronucleosides". The use of certain 2'-fluoronucleosides to treat HCV is disclosed.

Other compounds that can be used as second agents include 1-amino-alkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), benzimidazoles (U.S. Pat. No. 5,891,874 to Colacino et al.), plant extracts (U.S. Pat. No. 5,837,257 to Tsai et al., U.S. Pat. No. 5,725,859 to Omer et al., and U.S. Pat. No. 6,056,961), and piperidines (U.S. Pat. No. 5,830,905 to Diana et al.).

In certain embodiments, a compound of Formula 2001, I-XXIX, 1-23byii and 1001-1002, or a composition comprising a compound of Formula 2001, I-XXIX, 1-23byii and 1001-1002, is administered in combination or alternation with a second anti-viral agent, wherein the second anti-viral agent is an interferon, a nucleotide analogue, a polymerase inhibitor, an NS3 protease inhibitor, an NS5A inhibitor, an entry inhibitor, a non-nucleoside polymerase inhibitor, a cyclosporine immune inhibitor, an NS4A antagonist, an NS4B-RNA binding inhibitor, a locked nucleic acid mRNA inhibitor, a cyclophilin inhibitor, or combination thereof.

Exemplary Second Therapeutic Agents for Treatment of HCV

In certain embodiments, one or more compounds provided herein can be administered in combination or alternation with an anti-hepatitis C virus interferon, such as Intron A® (interferon alfa-2b) and; Roferon A® (Recombinant interferon alfa-2a), Infergen® (consensus interferon; interferon alfa-con-1), PEG-Intron® (pegylated interferon alfa-2b), and Pegasys® (pegylated interferon alfa-2a). In certain embodiments, one or more compounds provided herein can be administered in combination or alternation with ribavirin and in combination or alternation with an anti-hepatitis C virus interferon. In certain embodiments, one or more compounds provided herein can be administered in combination or alternation with ribavirin, in combination or alternation with an anti-hepatitis C virus interferon, and in combination or alternation with an anti-hepatitis C virus protease inhibitor. In certain embodiments, one or more compounds provided herein can be administered in combination or alternation with ribavirin. In certain embodiments, one or more compounds provided herein can be administered in combination or alternation with an anti-hepatitis C virus interferon and without ribavirin. In certain embodiments, one or more compounds provided herein can be administered in combination or alternation with an anti-hepatitis C virus interferon, in combination or alternation with an anti-hepatitis C virus protease inhibitor, and without ribavirin.

In certain embodiments, the anti-hepatitis C virus interferon is infergen, IL-29 (PEGInterferon lambda), R7025 (Maxy-alpha), Belerofon, Oral Interferon alpha, BLX-883 (Locteron), omega interferon, multiferon, medusa interferon, Albuferon or REBIF®.

In certain embodiments, one or more compounds provided herein can be administered in combination or alternation with an anti-hepatitis C virus polymerase inhibitor, such as ribavirin, viramidine, HCV POL, NM 283 (valopicitabine), MK-0608, 7-Fluoro-MK-0608, PSI-6130, R1626, PSI-6206, PSI-938, R1479, HCV-796, VX-950 (Telaprevir, Vertex), GS 9190 NN (Gilead), GS 9256 (Gilead), PSI-7792 (BMS), BI 207127 (BI), R7128 (Roche), PSI-7977 (sofosbuvir, Sovaldi; Pharmasset), PSI-938 (Pharmasset), VX-222 (Vertex), ALS-2200 (Vertex), ALS-2158 (Vertex), MK-0608 (Merck), TMC649128 (Medivir), PF-868554 (Pfizer), PF-4878691 (Pfizer), ANA598 (Roche), VCH-759 (Vertex), IDX184 (Idenix), IDX375 (Idenix), A-837093 (Abbott), GS 9190 (Gilead), GSK625433 (GlaxoSmithKline), ABT-072 (Abbott), ABT-333 (Abbott), INX-189 (Inhibitex), or EDP-239 (Enanta).

In certain embodiments, the one or more compounds provided herein can be administered in combination with ribavarin and an anti-hepatitis C virus interferon, such as Intron A® (interferon alfa-2b) and Pegasys® (Peginterferon alfa-2a); Roferon A® (Recombinant interferon alfa-2a), Infergen® (consensus interferon; interferon alfacon-1), PEG-Intron® (pegylated interferon alfa-2b), Zalbin (albinterferon alfa-2b), omega interferon, pegylated interferon lambda, and Pegasys® (pegylated interferon alfa-2a).

In certain embodiments, one or more compounds provided herein can be administered in combination or alternation with an anti-hepatitis C virus protease inhibitor such as ITMN-191, SCH 503034 (boceprevir), VX950 (telaprevir), VX985, VX500, VX813, PHX1766, BMS-650032, GS 9256, BI 201335, IDX320, R7227, MK-7009 (vaniprevir), simeprevir (TMC435), BMS-791325, ACH-1625, ACH-2684, ABT-450, or AVL-181.

In certain embodiments, one or more compounds provided herein can be administered in combination or alternation with an HCV NS5A inhibitor, such as BMS-790052 (daclatasvir, Bristol-Myers Squibb), PPI-461 (Presidio Pharmaceuticals), PPI-1301 (Presidio Pharmaceuticals), IDX-719 (samatasvir, Idenix Pharmaceuticals), AZD7295 (Arrow Therapeutics, AstraZeneca), EDP-239 (Enanta), ACH-2928 (Achillion), ACH-3102 (Achillion), ABT-267 (Abbott), or GS-5885 (Gilead).

In certain embodiments, one or more compounds provided herein can be administered in combination or alternation with an anti-hepatitis C virus vaccine, such as TG4040, PeviPRO™, CGI-5005, HCV/MF59, GV1001, IC41, GNI-103, GenPhar HCV vaccine, C-Vaxin, CSL123, Hepavaxx C, ChronVac-C® or INNO0101 (E1).

In certain embodiments, one or more compounds provided herein can be administered in combination or alternation with an anti-hepatitis C virus monoclonal antibody, such as MBL-HCV1, AB68 or XTL-6865 (formerly HepX-C); or an anti-hepatitis C virus polyclonal antibody, such as cicavir.

In certain embodiments, one or more compounds provided herein can be administered in combination or alternation with an anti-hepatitis C virus immunomodulator, such as Zadaxin® (thymalfasin), SCV-07, NOV-205, or Oglufanide.

In certain embodiments, one or more compounds provided herein can be administered in combination or alternation with cyclophilin inhibitor, such as Enanta cyclophilin binder, SCY-635, or Debio-025.

In certain embodiments, one or more compounds provided herein can be administered in combination or alternation with Nexavar, doxorubicin, PI-88, amantadine, JBK-122, VGX-410C, MX-3253 (Ceglosivir), Suvus (BIVN-401 or virostat), PF-03491390 (formerly IDN-6556), G126270, UT-231B, DEBIO-025, EMZ702, ACH-0137171, MitoQ, ANA975, AVI-4065, Bavituxinab (Tarvacin), Alinia (nitrazoxanide) or PYN17.

In certain embodiments, one or more compounds provided herein can be administered in combination or alternation with simeprevir, sofosbuvir, samatasvir, telaprevir, boceprevir, interferon alfacon-1, interferon alfa-2b, pegylated interferon alpha 2a, pegylated interferon alpha 2b, ribavirin, or combinations thereof.

In certain embodiments, one or more compounds provided herein can be administered in combination or alternation with a protease inhibitor. In certain embodiments, one or more compounds provided herein can be administered in combination or alternation with telaprevir. In certain embodiments, one or more compounds provided herein can be administered in combination or alternation with boceprevir.

In certain embodiments, one or more compounds provided herein can be administered in combination or alternation with a protease inhibitor and in combination or alternation with ribavirin. In certain embodiments, one or more compounds provided herein can be administered in combination or alternation with telaprevir and in combination or alternation with ribavirin. In certain embodiments, one or more compounds provided herein can be administered in combination or alternation with boceprevir and in combination or alternation with ribavirin.

In certain embodiments, one or more compounds provided herein can be administered in combination or alternation with a protease inhibitor and not in combination or alternation with ribavirin. In certain embodiments, one or more compounds provided herein can be administered in combination or alternation with telaprevir and not in combination or alternation with ribavirin. In certain embodiments, one or more compounds provided herein can be administered in combination or alternation with boceprevir and not in combination or alternation with ribavirin.

In certain embodiments, one or more compounds provided herein can be administered in combination or alternation with an interferon. In certain embodiments, one or more compounds provided herein can be administered in combination or alternation with interferon alfacon-1. In certain embodiments, one or more compounds provided herein can be administered in combination or alternation with interferon alfa-2b. In certain embodiments, one or more compounds provided herein can be administered in combination or alternation with pegylated interferon alpha 2a. In certain embodiments, one or more compounds provided herein can be administered in combination or alternation with pegylated interferon alpha 2b.

In certain embodiments, one or more compounds provided herein can be administered in combination or alternation with an interferon and in combination or alternation with ribavirin. In certain embodiments, one or more compounds provided herein can be administered in combination or alternation with interferon alfacon-1 and in combination or alternation with ribavirin. In certain embodiments, one or more compounds provided herein can be administered in combination or alternation with interferon alfa-2b and in combination or alternation with ribavirin. In certain embodiments, one or more compounds provided herein can be administered in combination or alternation with pegylated interferon alpha 2a and in combination or alternation with ribavirin. In certain embodiments, one or more compounds provided herein can be administered in combination or alternation with pegylated interferon alpha 2b and in combination or alternation with ribavirin.

In certain embodiments, one or more compounds can be administered in combination or alternation with one or more of the second agents provided herein and not in combination or alternation with ribavirin. In certain embodiments, one or more compounds provided herein can be administered in combination or alternation with an interferon and not in combination or alternation with ribavirin. In certain embodiments, one or more compounds provided herein can be administered in combination or alternation with interferon alfacon-1 and not in combination or alternation with ribavirin. In certain embodiments, one or more compounds provided herein can be administered in combination or alternation with interferon alfa-2b and not in combination or alternation with ribavirin. In certain embodiments, one or more compounds provided herein can be administered in combination or alternation with pegylated interferon alpha 2a and not in combination or alternation with ribavirin. In certain embodiments, one or more compounds provided herein can be administered in combination or alternation with pegylated interferon alpha 2b and not in combination or alternation with ribavirin.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); THF (tetrahydrofuran); CDCl$_3$ (deuterated chloroform); AcOH (acetic acid); DCM (dichloromethane); DMSO (dimethylsulfoxide); DMSO-d$_6$ (deuterated dimethylsulfoxide); EtOAc (ethyl acetate); MeOH (methanol); and BOC (t-butyloxycarbonyl).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Example 1

Preparation of Thiophosphate Nucleosides

Compounds 8b, 9b and 10b

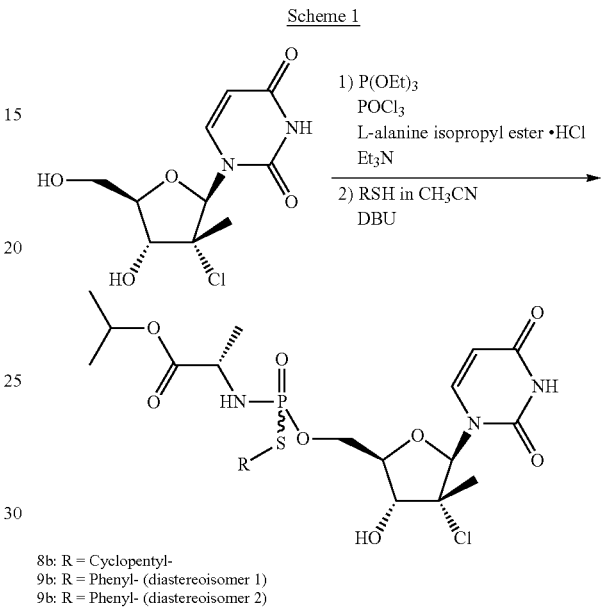

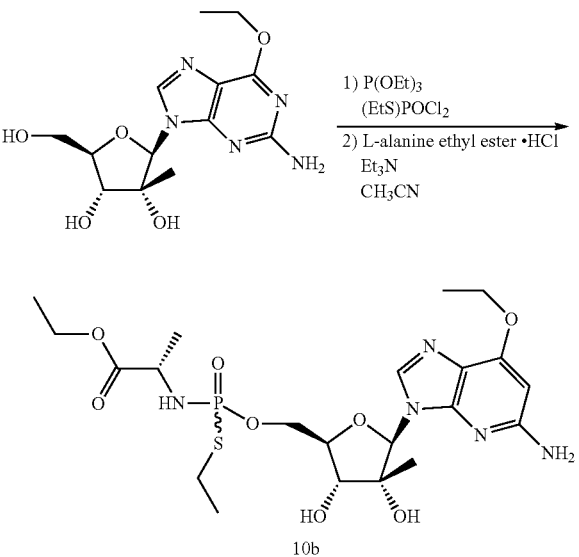

General Method A.

The following procedure was used to obtain compounds 8b and 9b.

To a solution of 2'-chloro-2'-C-methyl-uridine (3.61 mmol) in triethyl phosphate (5 mL) at 0° C. under nitrogen was added POCl₃ (5.42 mmol). The reaction mixture was allowed to warm to room temperature and stirred at this temperature during 12 hours. The reaction mixture was cooled down again to 0° C. and L-Alanine isopropyl ester hydrochloride (3.98 mmol) was added followed by addition of triethylamine (18.07 mmol). The reaction was stirred at room temperature during 20 minutes.

The reaction mixture was cooled down to 0° C. and appropriate thiol (14.46 mmol) in CH₃CN (4 mL) was added followed by addition of DBU (14.46 mmol). The reaction mixture was stirred at room temperature during 1 hour. The mixture was diluted with ethyl acetate and washed with brine. The organic layer was dried over Na₂SO₄, filtered, and concentrated under reduced pressure. The crude was purified by chromatography on a Biotage column (eluent: CH₂Cl₂ to CH₂Cl₂/CH₃OH 8/2) and by preparative HPLC to give the pure diastereoisomers.

Compound 8b

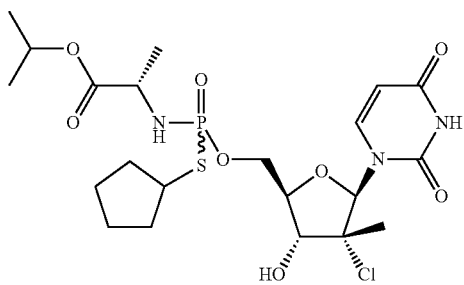 [SMILES: CC(C)OC(=O)[C@H](C)NP(=O)(OC[C@H]1O[C@@H](n2ccc(=O)[nH]c2=O)[C@](C)(Cl)[C@@H]1O)SC1CCCC1]

Compound 8b Dia 1

White solid; $^1$H NMR (MeOD, 400 MHz) δ (ppm) 1.25 (d, J=6.07 Hz, 3H), 1.27 (d, J=6.07 Hz, 3H), 1.41 (d, J=7.31 Hz, 3H), 1.54 (s, 3H), 1.62-1.78 (m, 6H), 2.11-2.18 (m, 2H), 3.48-3.56 (m, 1H), 3.87-3.95 (m, 1H), 3.99-4.02 (m, 1H), 4.18-4.22 (m, 1H), 4.36 (ddd, J=11.97 Hz, J=5.75 Hz, J=2.64 Hz 1H), 4.54 (ddd, J=12.08 Hz, J=5.83 Hz, J=2.12 Hz, 1H), 5.01 (heptuplet, J=6.25 Hz, 1H), 5.80 (d, J=8.16 Hz, 1H), 6.40 (s, 1H), 7.85 (d, J=8.16 Hz, 1H); $^{31}$P NMR (MeOD, 161.98 MHz) δ (ppm) 33.78 (s, 1P); MS (ESI) m/z=554.2 (MH⁺).

Compound 8b Dia 2

White solid; $^1$H NMR (MeOD, 400 MHz) δ (ppm) 1.26 (d, J=6.21 Hz, 3H), 1.27 (d, J=6.21 Hz, 3H), 1.42 (d, J=7.14 Hz, 3H), 1.54 (s, 3H), 1.58-1.78 (m, 6H), 2.07-2.18 (m, 2H), 3.47-3.54 (m, 1H), 3.92-4.00 (m, 1H), 4.03-4.06 (m, 1H), 4.17-4.21 (m, 1H), 4.32 (ddd, J=11.98 Hz, J=5.75 Hz, J=2.68 Hz 1H), 4.50 (ddd, J=11.98 Hz, J=6.23 Hz, J=1.97 Hz, 1H), 5.02 (heptuplet, J=6.21 Hz, 1H), 5.82 (d, J=8.16 Hz, 1H), 6.40 (s, 1H), 7.82 (d, J=8.16 Hz, 1H); $^{31}$P NMR (MeOD, 161.98 MHz) δ (ppm) 34.78 (s, 1P); MS (ESI) m/z=554.2 (MH⁺).

Compound 9b

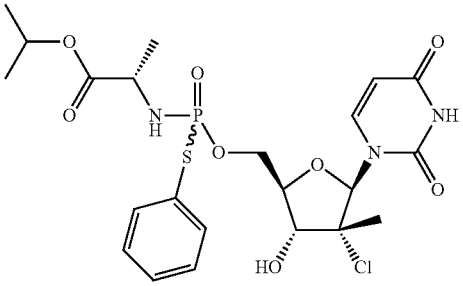 [SMILES: CC(C)OC(=O)[C@H](C)NP(=O)(OC[C@H]1O[C@@H](n2ccc(=O)[nH]c2=O)[C@](C)(Cl)[C@@H]1O)Sc1ccccc1]

Diastereoisomer 1 white solid; $^1$H NMR (MeOD, 400 MHz) δ (ppm) 1.21 (d, J=7.20 Hz, 3H), 1.24 (d, J=6.22 Hz, 3H), 1.26 (d, J=6.22 Hz, 3H), 1.52 (s, 3H), 3.80-3.88 (m, 1H), 3.92-3.94 (m, 1H), 4.18-4.22 (m, 1H), 4.41-4.46 (m, 1H), 4.60-4.65 (m, 1H), 4.99 (heptuplet, J=6.20 Hz, 1H), 5.79 (d, J=8.16 Hz, 1H), 6.40 (s, 1H), 7.37-7.44 (m, 3H), 7.62-7.65 (m, 2H), 7.77 (d, J=8.16 Hz, 1H); $^{31}$P NMR (MeOD, 161.98 MHz) δ (ppm) 30.45 (s, 1P); MS (ESI) m/z=562 (MH⁺).

Diastereoisomer 2 white solid; $^1$H NMR (MeOD, 400 MHz) δ (ppm) 1.25 (d, J=6.20 Hz, 3H), 1.28 (d, J=6.20 Hz, 3H), 1.36 (d, J=7.07 Hz, 3H), 1.52 (s, 3H), 3.91-4.02 (m, 2H), 4.16-4.20 (m, 1H), 4.36-4.41 (m, 1H), 4.56-4.61 (m, 1H), 4.99 (heptuplet, J=6.23 Hz, 1H), 5.64 (d, J=8.13 Hz, 1H), 6.39 (s, 1H), 7.32-7.40 (m, 3H), 7.58-7.62 (m, 3H); $^{31}$P NMR (MeOD, 161.98 MHz) δ (ppm) 31 (s, 1P); MS (ESI) m/z=562 (MH⁺).

Compound 10b

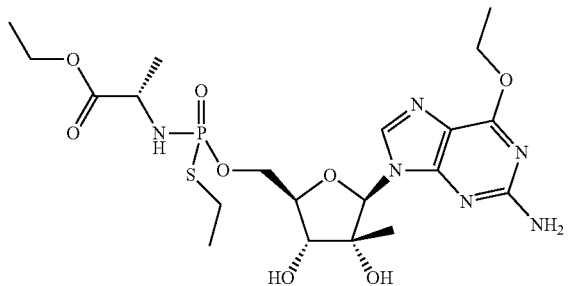 [SMILES: CCOC(=O)[C@H](C)NP(=O)(OC[C@H]1O[C@@H](n2cnc3c(OCC)nc(N)nc32)[C@](C)(O)[C@@H]1O)SCC]

To a solution of 2'-C-methyl-6-ethoxy-guanosine (3.07 mmol) in triethyl phosphate (3 mL) at 0° C. under nitrogen was added 1-dichlorophosphorylsulfanylethane (Pestic. Sci. (1984), 15, 553-556) (6.15 mmol). The reaction mixture was stirred at room temperature. To a solution of L-Alanine ethyl ester hydrochloride (4.61 mmol) in CH₃CN (5 mL) was added dropwise triethylamine (15.37 mmol) and the reaction mixture was stirred at 0° C. during 30 minutes before addition dropwise to the first reaction mixture (pH must be neutral). After a night at room temperature, the reaction mixture was quenched on phosphate buffer solution and extracted with ethyl acetate. The organic layer was dried over $Na_2SO_4$, filtered, and concentrated under reduced pressure. The crude was purified by chromatography on a silica gel (eluent: $CH_2Cl_2/CH_3OH$ 0 to 10%) and by preparative HPLC to give a mixture of diastereoisomers.

$^1$H NMR (DMSO-d$_6$, 400 MHz) δ (ppm) 0.796 (s, 1.5H), 0.803 (s, 1.5H), 1.14-1.22 (m, 6H), 1.28 (d, J=7.09 Hz, 3H), 1.35 (t, J=7.09 Hz, 3H), 2.65-2.77 (m, 2H), 3.72-3.88 (m, 1H), 4.00-4.10 (m, 4H), 4.17-4.36 (m, 2H), 4.44 (q, J=7.07 Hz, 2H), 5.21 (d, J=3.18 Hz, 1H), 5.40 (dd, J=6.13 Hz and 15.46 Hz, 1H), 5.837 (s, 0.5H), 5.841 (s, 0.5H), 6.11-6.18 (m, 1H), 6.46 (s, 2H), 7.91 (s, 0.5H), 7.92 (s, 0.5H); $^{31}$P NMR (MeOD, 161.98 MHz) δ (ppm) 31.32 (s, 0.5P), 31.78 (s, 0.5P); MS (ESI) m/z=549.2 (MH$^+$).

Compound 11b was synthesized from 2'-fluoro-2'-C-methyl-6-ethoxy-guanosine according to the procedure described for compound 10b in Scheme 2. The mixture of diastereoisomers was separated by MS-preparative HPLC.

Compound 11b Dia 1

White solid; $^1$H NMR (DMSO-d$_6$, 400 MHz) δ (ppm) 1.07 (d, J=22.13 Hz, 3H), 1.15-1.20 (m, 6H), 1.27 (d, J=7.01 Hz, 3H), 1.34 (t, J=7.01 Hz, 3H), 2.67-2.74 (m, 2H), 3.74-3.83 (m, 1H), 4.05-4.11 (m, 3H), 4.24-4.39 (m, 3H), 4.44 (q, J=7.01 Hz, 2H), 5.85 (brs, 1H), 6.09 (d, J=19.04 Hz, 1H), 6.19 (dd, J=13.03 Hz, 10.02 Hz, 1H), 6.57 (brs, 2H), 7.94 (s, 1H); $^{31}$P NMR (DMSO-d$_6$, 161.98 MHz) δ (ppm) 31.44 (s, 1P); MS (ESI) m/z=551.3 (MH$^+$).

Compound 11b Dia 2

White solid; $^1$H NMR (DMSO-d$_6$, 400 MHz) δ (ppm) 1.07 (d, J=22.73 Hz, 3H), 1.14-1.21 (m, 6H), 1.27 (d, J=7.05 Hz, 3H), 1.35 (t, J=7.05 Hz, 3H), 2.69-2.77 (m, 2H), 3.78-3.85 (m, 1H), 4.03-4.08 (m, 3H), 4.19-4.38 (m, 3H), 4.44 (q, J=6.84 Hz, 2H), 5.82 (brs, 1H), 6.08 (d, J=19.22 Hz, 1H), 6.14-6.20 (m, 1H), 6.57 (brs, 2H), 7.95 (s, 1H); $^{31}$P NMR (DMSO-d$_6$, 161.98 MHz) δ (ppm) 31.94 (s, 1P); MS (ESI) m/z=551.3 (MH$^+$).

Compound 12b was synthesized from 2'-C-methyl-uridine and N-propanethiol according to procedure described for compound 8b in Scheme 1 with triethylamine instead of DBU. The mixture of diastereoisomers was separated by MS-preparative HPLC.

Compound 12b Dia 1

White solid; $^1$H NMR (MeOD, 400 MHz) δ (ppm) 0.91 (t, J=7.26 Hz, 3H), 1.07 (s, 3H), 1.16 (t, J=5.76 Hz, 6H), 1.26-1.31 (m, 3H), 1.58-1.67 (m, 2H), 2.69-2.77 (m, 2H), 3.71 (d, J=9.25 Hz, 1H), 3.75-3.83 (m, 1H), 3.98-4.02 (m, 1H), 4.23 (ddd, J=11.83 Hz, J=5.92 Hz, J=2.90 Hz, 1H), 4.40 (ddd, J=11.71 Hz, J=5.86 Hz, J=2.05 Hz, 1H), 4.91 (heptuplet, J=6.31 Hz, 1H), 5.68 (d, J=8.11 Hz, 1H), 5.88 (s, 1H), 7.67 (d, J=8.11 Hz, 1H); $^{31}$P NMR (MeOD, 161.98 MHz) δ (ppm) 34.88 (s, 1P); MS (ESI) m/z=510.2 (MH$^+$).

Compound 12b Dia 2

White solid; $^1$H NMR (MeOD, 400 MHz) δ (ppm) 0.88 (t, J=7.36 Hz, 3H), 1.07 (s, 3H), 1.16 (d, J=6.20 Hz, 3H), 1.17 (d, J=6.20 Hz, 3H), 1.31 (d, J=7.11 Hz, 3H), 1.55-1.63 (m, 2H), 2.68-2.75 (m, 2H), 3.73 (d, J=9.30 Hz, 1H), 3.80-3.88 (m, 1H), 3.97-4.01 (m, 1H), 4.20 (ddd, J=11.81 Hz, J=5.91 Hz, J=3.21 Hz, 1H), 4.36 (ddd, J=11.81 Hz, J=6.71 Hz, J=2.05 Hz, 1H), 4.92 (heptuplet, J=6.27 Hz, 1H), 5.70 (d, J=8.09 Hz, 1H), 5.88 (s, 1H), 7.65 (d, J=8.09 Hz, 1H); $^{31}$P NMR (MeOD, 161.98 MHz) δ (ppm) 35.64 (s, 1P); MS (ESI) m/z=510.2 (MH$^+$).

Compound 13b was synthesized from 2'-C-methyl-guanosine according to procedure described for compound 10b in Scheme 2.

Compound 13b

White solid; $^1$H NMR (DMSO-d$_6$, 400 MHz) δ (ppm) 0.82 (s, 3H), 1.14-1.22 (m, 6H), 1.28 (d, J=7.06 Hz, 3H), 2.68-2.77 (m, 2H), 3.77-3.88 (m, 1H), 3.95-4.11 (m, 4H), 4.15-4.32 (m, 2H), 5.17 (s, 0.85H), 5.18 (s, 0.15H), 5.40 (d, J=5.86 Hz, 0.85H), 5.43 (d, J=6.55 Hz, 0.15H), 5.74 (s, 1H), 6.16 (dd, J=13.10 Hz, 10.34 Hz, 1H), 6.52 (brs, 2H), 7.745 (s, 015H), 7.755 (s, 085H); $^{31}$P NMR (DMSO-d$_6$, 161.98 MHz) δ (ppm) 31.81 (s, 0.85), 31.33 (s, 0.15P); MS (ESI) m/z=521.2 (MH$^+$).

Compound 14b was synthesized from 2'-chloro-2'-C-methyl-uridine and N-propanethiol according to procedure described for compound 8b in Scheme 1 with triethylamine instead of DBU. The mixture of diastereoisomers was separated by MS-preparative HPLC.

Compound 14b Dia 1

White solid; $^1$H NMR (MeOD, 400 MHz) δ (ppm) 0.91 (t, J=7.28 Hz, 3H), 11.15-1.18 (m, 6H), 1.31 (d, J=7.33 Hz, 3H), 1.44 (s, 3H), 2.71-2.78 (m, 2H), 3.78-3.82 (m, 1H), 3.89-3.91 (m, 1H), 4.07-4.16 (m, 4H), 4.23-4.28 (m, 1H), 4.41-4.48 (m, 2H), 4.91 (heptuplet, J=6.23 Hz, 1H), 5.71 (d, J=8.19 Hz, 1H), 6.30 (brs, 1H), 7.73 (d, J=8.19 Hz, 1H); $^{31}$P NMR (MeOD, 161.98 MHz) δ (ppm) 34.89 (s, 1P); MS (ESI) m/z=528.2 (MH$^+$).

Compound 14b Dia 2

White solid; $^1$H NMR (MeOD, 400 MHz) δ (ppm) 0.89 (t, J=7.30 Hz, 3H), 1.16 (d, J=6.20 Hz, 3H), 1.17 (d, J=6.28 Hz, 3H), 1.32 (d, J=7.11 Hz, 3H), 1.44 (s, 3H), 2.69-2.77 (m, 2H), 3.83-3.95 (m, 2H), 4.07-4.13 (m, 2H), 4.20-4.25 (m, 1H), 4.37-4.50 (m, 2H), 4.92 (heptuplet, J=6.23 Hz, 1H), 5.72 (d, J=8.11 Hz, 1H), 6.31 (brs, 1H), 7.71 (d, J=8.11 Hz, 1H); $^{31}$P NMR (MeOD, 161.98 MHz) δ (ppm) 35.75 (s, 1P); MS (ESI) m/z=528.2 (MH$^+$).

Compound 17b was synthesized from 2'-chloro-2'-C-methyl-uridine and methyl thioglycolate according to procedure described for compound 8b in Scheme 1.

Compound 17b

White solid; $^1$H NMR (MeOD, 400 MHz) δ (ppm) 1.25-1.30 (m, 6H), 1.42 (t, J=7.45 Hz, 3H), 1.56 (s, 3H), 3.72-3.74 (m, 3H), 3.88-4.10 (m, 2H), 4.18-4.22 (m, 1H), 4.33-4.43 (m, 1H), 4.54-4.60 (m, 1H), 5.02 (heptuplet, J=6.20 Hz, 1H), 5.83 (d, J=8.15 Hz, 0.55H), 5.84 (d, J=8.15 Hz, 0.45H), 6.43 (brs, 1H), 7.79 (d, J=8.15 Hz, 0.45H), 7.84 (d, J=8.15 Hz, 0.55H); $^{31}$P NMR (MeOD, 161.98 MHz) δ (ppm) 33.44 (s, 0.45P), 32.57 (s, 0.55P); MS (ESI) m/z=558.2 (MH$^+$).
Compound 1b
Two Separated Diastereomers at Phosphorus
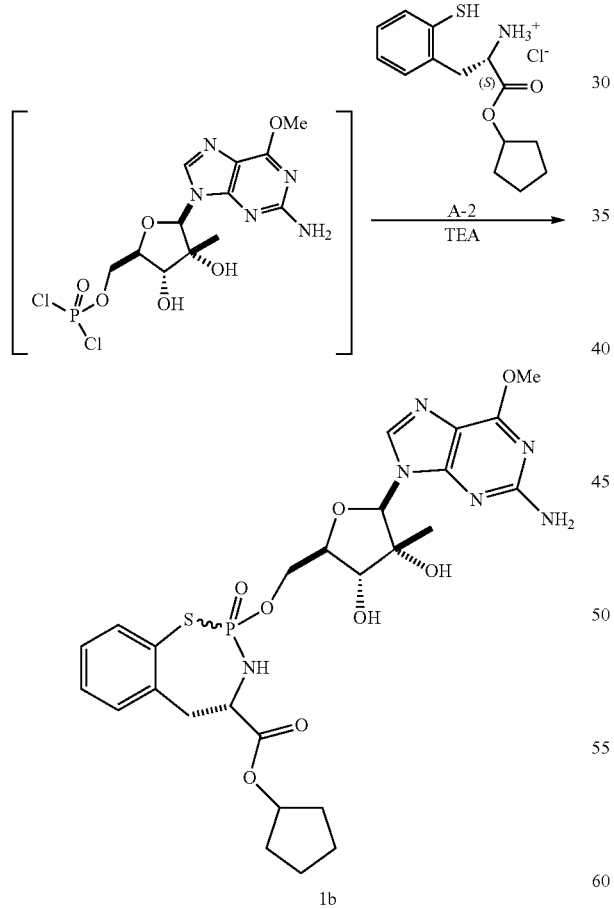
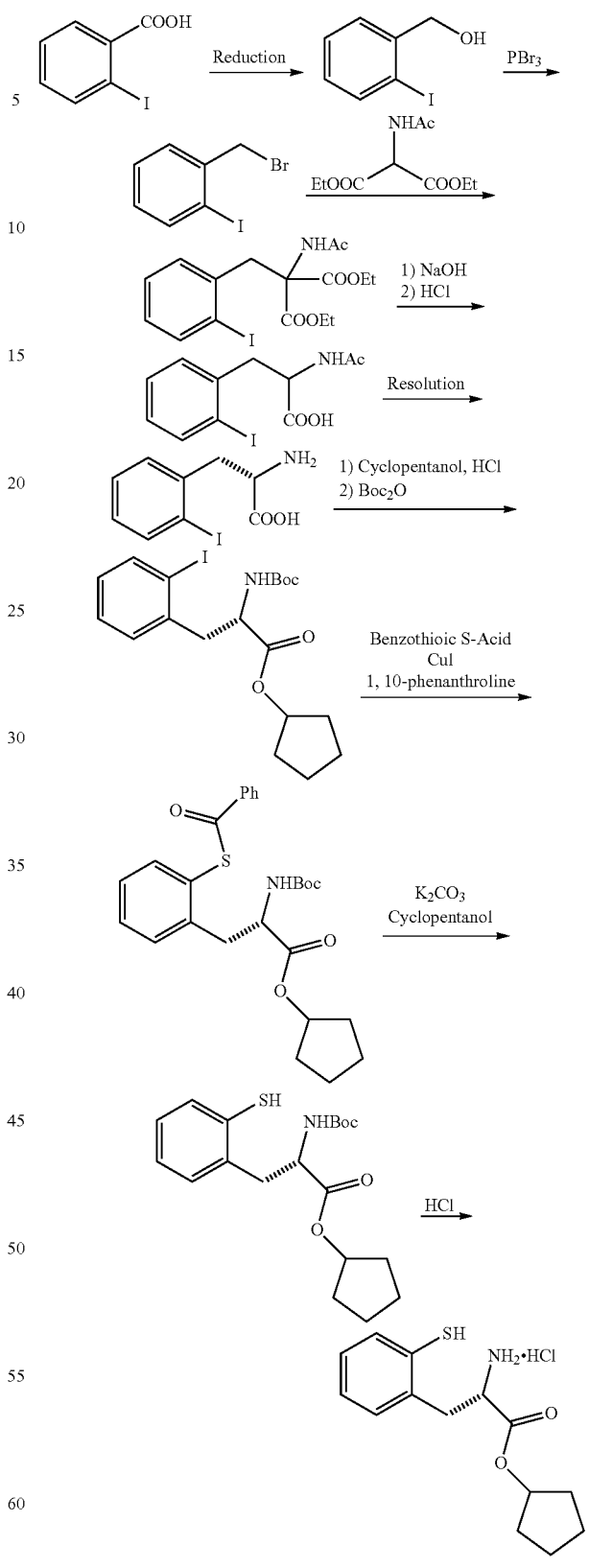
The chiral reagent A-2 was prepared by the following scheme; 97% ee was observed.

A-2, (S)-1-(cyclopentyloxy)-3-(2-mercaptophenyl)-1-oxopropan-2-aminium chloride: LCMS (ES+, m/e=266.2, M++1), $^1$H NMR (300 MHz, D$_2$O) δ 7.33 (m, 1H), 7.13 (m, 3H), 5.08 (m, 1H), 4.32 (t, 1H), 3.17 (m, 2H), 1.42-1.71 (m, 8H).

The nucleoside (A-N1, 0.44 g, 1.42 mmol) was stirred in triethylphosphate (PO(OEt)$_3$, 20 mL) and was cooled to –20° C. Phosphorous oxychloride (POCl$_3$, 0.28 g, 1.85 mmol, 1.3 eq) was added drop-wise and the mixture was stirred at –20° C. for 30 min. The mixture was allowed to warm to 0° C. and was stirred at this temperature for 4 hours. This mixture was then cooled to –50° C. and the amine hydrochloride (A-2, 0.43 g, 1.42 mmol, 1.0 eq) was added followed by triethylamine (TEA, 0.59 mL, 4.6 mmol, 2.3 eq). After stirring at –50° C. for 30 minutes, an additional portion of TEA (1.11 mL, 6.13 mmol, 4.3 eq) was added and the mixture was allowed to warm to room temperature and was stirred overnight. The crude product was precipitated by pouring the reaction mixture into petroleum ether (300 mL) and was isolated by vacuum filtration. This material (1.58 g) was purified by preparative HPLC affording compound 1b, diastereomer 1 (33 mg, 37%) and compound 1b, diastereomer 2 (20 mg, 23%).

Diastereomer 1

HPLC (Method 1), RT 13.55 min, 98.4 A %; LCMS, (ES+, m/e=621.1, M++1); $^1$H NMR (300 MHz, CD$_3$OD) δ 7.92 (s, 1H), 7.47 (d, 1H), 7.29 (m, 1H), 7.18 (m, 2H), 5.94 (s, 1H), 5.14 (m, 1H), 4.53-4.83 (m, 3H), 4.33 (m, 1H), 4.20 (m, 2H), 4.06 (s, 3H), 3.68 (m, 1H), 3.40 (m, 1H), 1.64-1.89 (m, 8H), 0.96 (s, 3H); $^{31}$P NMR (121 MHz, CD$_3$OD) δ 28.361.

Diastereomer 2

HPLC (Method 1), RT 17.45 min, 98.9 A %; LCMS, (ES+, m/e=621.1, M++1); $^1$H NMR (300 MHz, CD$_3$OD) δ 7.85 (s, 1H), 7.54 (d, 1H), 7.20 (m, 3H), 5.93 (s, 1H), 5.11 (m, 1H), 4.62 (m, 1H), 4.40 (m, 1H), 4.18 (m, 3H), 4.05 (s, 3H), 3.57 (m, 1H), 3.37 (m, 1H), 1.64-1.89 (m, 8H), 0.91 (s, 3H); $^{31}$P NMR (121 MHz, CD$_3$OD) δ 27.984.

HPLC Method 1:

C18, 4.6×150 mm, 5 micron, 0.1% Ammonium acetate, 45%-45%-97% MeCN (0-30-35 min), 250 nm.

Compound 2by

Mixture of Diastereomers at Phosphorus

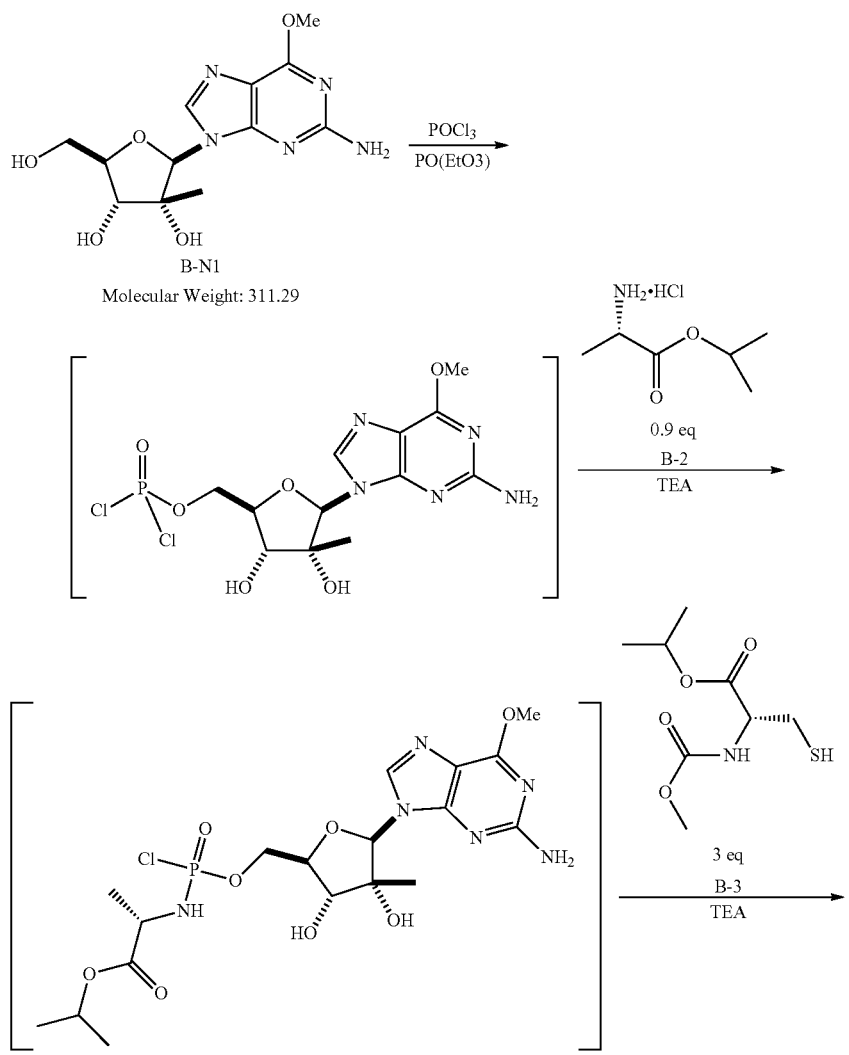

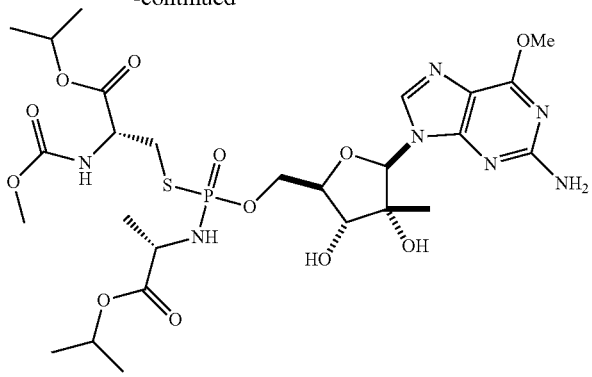

Molecular Weight: 707.69
2by

B-3 was prepared according to the following scheme:

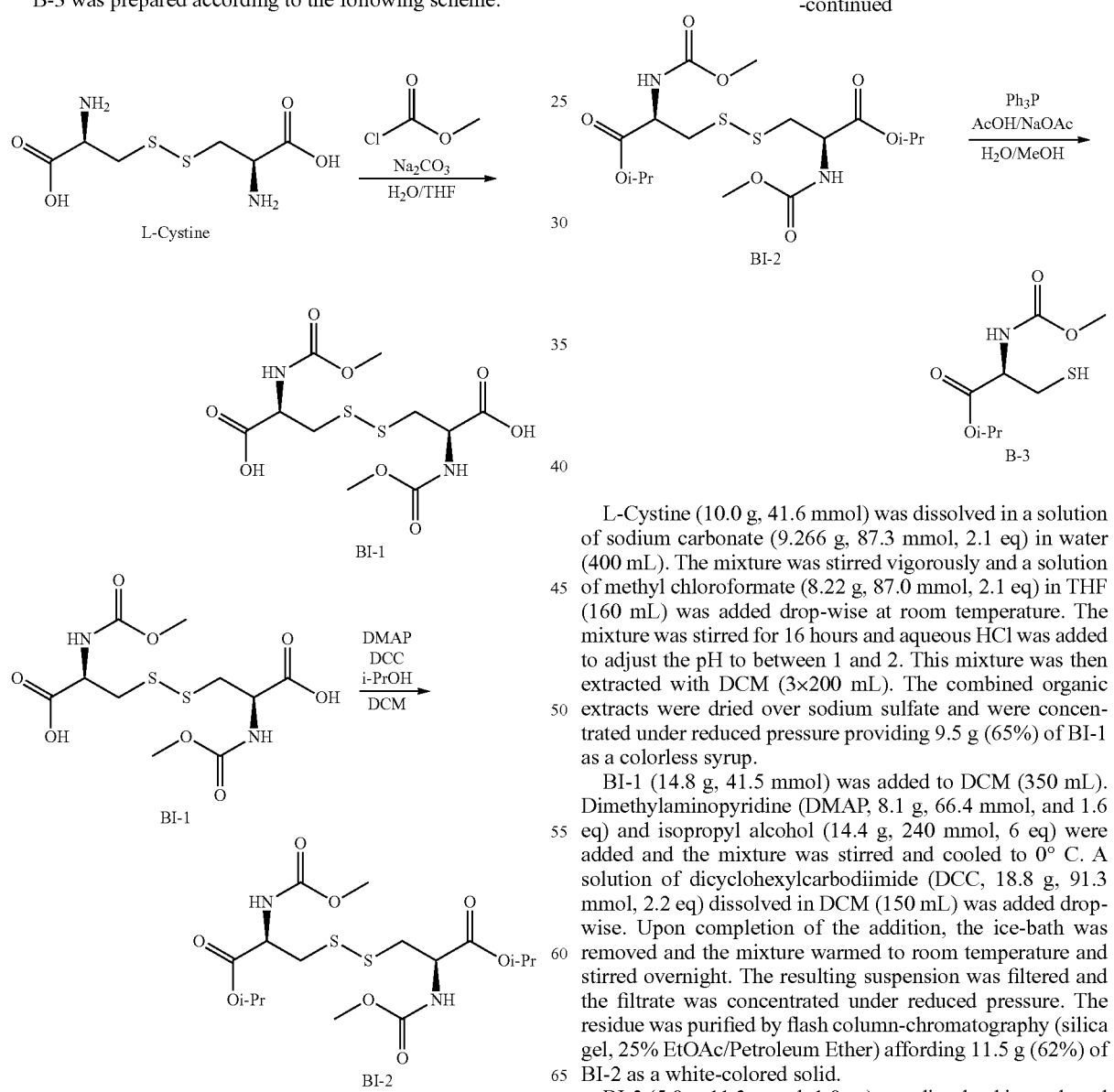

L-Cystine (10.0 g, 41.6 mmol) was dissolved in a solution of sodium carbonate (9.266 g, 87.3 mmol, 2.1 eq) in water (400 mL). The mixture was stirred vigorously and a solution of methyl chloroformate (8.22 g, 87.0 mmol, 2.1 eq) in THF (160 mL) was added drop-wise at room temperature. The mixture was stirred for 16 hours and aqueous HCl was added to adjust the pH to between 1 and 2. This mixture was then extracted with DCM (3×200 mL). The combined organic extracts were dried over sodium sulfate and were concentrated under reduced pressure providing 9.5 g (65%) of BI-1 as a colorless syrup.

BI-1 (14.8 g, 41.5 mmol) was added to DCM (350 mL). Dimethylaminopyridine (DMAP, 8.1 g, 66.4 mmol, and 1.6 eq) and isopropyl alcohol (14.4 g, 240 mmol, 6 eq) were added and the mixture was stirred and cooled to 0° C. A solution of dicyclohexylcarbodiimide (DCC, 18.8 g, 91.3 mmol, 2.2 eq) dissolved in DCM (150 mL) was added drop-wise. Upon completion of the addition, the ice-bath was removed and the mixture warmed to room temperature and stirred overnight. The resulting suspension was filtered and the filtrate was concentrated under reduced pressure. The residue was purified by flash column-chromatography (silica gel, 25% EtOAc/Petroleum Ether) affording 11.5 g (62%) of BI-2 as a white-colored solid.

BI-2 (5.0 g, 11.3 mmol, 1.0 eq) was dissolved in methanol (8 mL). A solution of acetic acid (0.2 mL) and sodium acetate (300 mg) in water (4 mL) were added followed by triphenylphosphine (Ph₃P, 5.0 g, 19.1 mmol, 1.7 eq). The resulting suspension was stirred at 80° C. overnight. The mixture was cooled to room temperature and was extracted with DCM (3×15 mL). The combined organic phases were dried over sodium sulfate and were concentrated under reduced pressure. Purification of the crude product by flash column-chromatography (silica gel) afforded 4.5 g (90%) of B-3 as a colorless oil.

B-2 was prepared as described below.

L-Alanine (10 g, 112.4 mmol, 1 eq) was dissolved in isopropanol (150 mL). Thionyl chloride (25 mL, 337 mmol, 3 eq) was added and the mixture was heated to reflux (100° C.) until the mixture became clear. The mixture was cooled and was concentrated under reduced pressure. The resulting material was crystallized to provide B-2 as a white-colored solid.

The nucleoside (B-N1, 933 mg, 3 mmol, 1 eq) was dissolved in triethylphosphate (10 mL). The mixture was cooled to 0° C. (ice-bath) under a nitrogen atmosphere and phosphorous oxychloride (504 mg, 3.3 mmol, 1.1 eq) was added drop-wise. The mixture was stirred at 0° C. for 1 hour. A solution of B-2 (501 mg, 3 mmol, 1.0 eq) and triethylamine (637 mg, 6.3 mmol, 2.1 eq) in triethylphosphate (2 mL) was prepared and was added drop-wise to the solution of B-N1. The mixture was allowed to stir at 0° C. for 30 minutes after which time a solution of B-3 (732 mg, 3.3 mmol, 1.1 eq) and triethylamine (1.183 g, 11.7 mmol, 3.9 eq) in DCM (5 mL) was added. The ice-bath was removed and the mixture was allowed to warm to room temperature and stirred overnight. The mixture was poured into 200 mL of petroleum ether and the resulting precipitate was collected by vacuum filtration. The crude product was purified by flash column-chromatography (4% MeOH/DCM) affording 500 mg of semi-pure 2by. This material was purified further by preparative HPLC to yield a 400 mg sample of the pure mixture of isomers 2by.

2by

HPLC (Method 2), RT 4.794 min, 99.4 A %; LCMS (ES⁺, m/e=708, M⁺+1); ¹H NMR (300 MHz, CD₃OD) δ 7.96, 7.96 (2×s, 1H), 5.98, 5.97 (2×s, 1H), 4.90 (m, 2H), 4.48 (m, 2H), 4.22 (m, 3H), 4.05 (s, 3H), 3.89 (1H, m), 3.65 (s, 3H), 3.35 (s, 2H), 3.31 (m, 1H), 1.33 (m, 3H), 1.20 (m, 12H), 0.976, 0.965 (2×s, 3H); ³¹P NMR (121 MHz, CD₃OD) δ 35.67, 35.50. HPLC Method 2: C18, 4.6×150 mm, 5 micron, 0.1% Ammonium acetate, 25%-97% MeCN (0-15 min), 250 nm.

Compound 23b

Two Diastereomers Isolated From a Four Isomer Mixture

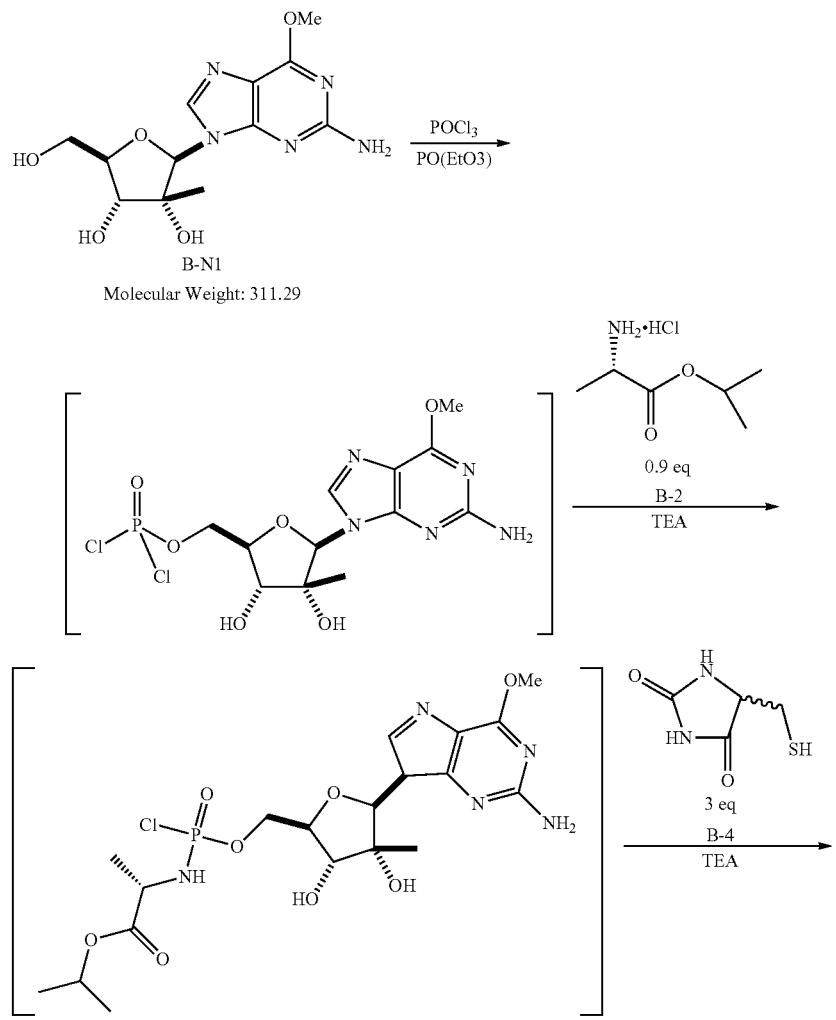

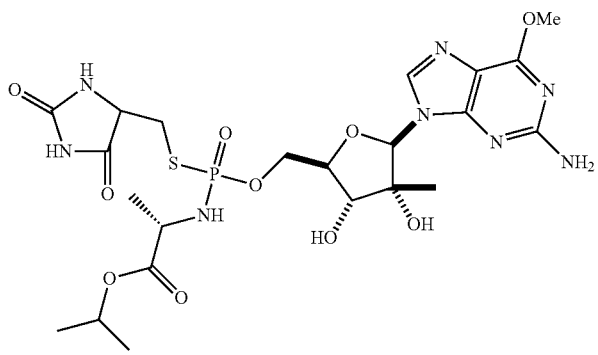

23b

Chemical Formula: C$_{22}$H$_{33}$N$_8$O$_{10}$PS
Molecular Weight: 632.5838

B-4 and B-2 were prepared as follows.

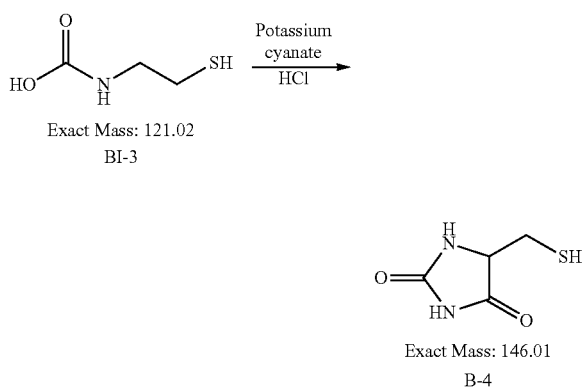

BI-3 (15 g, 124 mmol, 1 eq) and potassium cyanate (11.05 g, 136 mmol, 1.2 eq) were dissolved in water (75 mL). The mixture was heated to reflux and aqueous HCl (10%, 50 mL) was added. After refluxing for 30 minutes, the mixture was cooled to room temperature. DCM was added. The material which precipitated was isolated by filtration. This material was the desired product and was of sufficient purity to use in the coupling step.

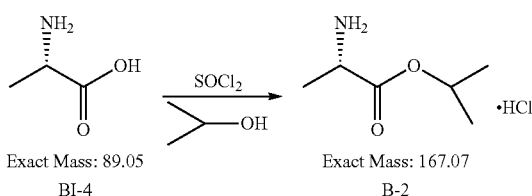

L Alanine (10 g, 112.4 mmol, 1 eq) was dissolved in isopropanol (150 mL). Thionyl chloride (25 mL, 337 mmol, 3 eq) was added and the mixture was heated to reflux (100° C.) until the mixture became clear. The mixture was cooled and was concentrated under reduced pressure. The resulting material was crystallized from ether and petroleum ether to provide B-2 a white-colored solid.

The nucleoside (B-N1, 1.5 g, 4.82 mmol) was stirred in triethylphosphate (PO(OEt)$_3$, 30 mL) and was cooled to −20° C. Phosphorous oxychloride (POCl$_3$, 0.96 g, 6.26 mmol, 1.3 eq) was added drop-wise and the mixture was stirred at −20° C. for 30 min. The mixture was allowed to warm to 0° C. and was stirred at this temperature for 4 hours. This mixture was cooled to −50° C. (dry ice/EtOH) B-2 (0.724 g, 4.34 mmol, 0.9 eq) was added followed by triethylamine (TEA, 1.54 mL, 11.08 mmol, 2.3 eq). After stirring at −50° C. for 30 minutes, B-4 (2.11 g, 14.46 mmol, 3 eq) was added to the mixture followed by triethylamine (TEA, 2.88 mL, 20.72 mmol, 4.3 eq). The mixture was allowed to warm to room temperature and was stirred overnight. Petroleum ether was added to the mixture and the precipitated material was isolated by vacuum filtration. This material was purified by column chromatography (silica gel, 200-300 mesh) using MeOH/DCM (0→7%) providing the crude product (570 mg). The crude product purified by preparative column chromatography affording compound 23b, diastereomer 1 (10 mg, 0.33%) and compound 23b, diastereomer 2 (10 mg, 0.33%).

Compound 23b, Diastereomer 1

HPLC (Method 3), RT 15.23 min, 96.9 A %; LCMS (ES$^+$, m/e=633.1, M$^+$+1); $^1$H NMR (300 MHz, CD$_3$OD) δ 7.95 (s, 1H), 5.96 (s, 1H), 4.97 (m, 1H), 4.48 (m, 3H), 4.35 (m, 1H), 4.18 (m, 1H), 4.05 (s, 3H), 4.02 (m, 3H), 3.80 (m, 1H), 3.60 (m, 1H), 1.34 (m, 3H), 1.22 (m, 6H), 0.98 (s, 3H); $^{31}$P NMR (121 MHz, CD$_3$OD) δ 7.40.

Compound 23b, Diastereomer 2

HPLC (Method 3), RT 16.58 min, 98.60 A %; LCMS (ES$^+$, m/e=633.1, M$^+$+1); $^1$H NMR (300 MHz, CD$_3$OD) δ 7.97 (s, 1H), 5.98 (s, 1H), 4.97 (m, 1H), 4.47 (m, 3H), 4.35 (m, 1H), 4.18 (m, 1H), 4.06 (s, 3H), 4.02 (s, 3H), 3.80 (m, 1H), 3.60 (m, 1H), 1.37 (m, 3H), 1.27 (m, 6H), 0.98 (s, 3H); $^{31}$P NMR (121 MHz, CD$_3$OD) δ 7.14.

HPLC Method 3:

C18, 4.6×150 mm, 5 micron, 0.1% Ammonium acetate, 15%-15%-50%-97% MeCN (0-20-25-30 min), 282 nm.

Compound 3b
Two Diastereomers Isolated From a Four Isomer Mixture
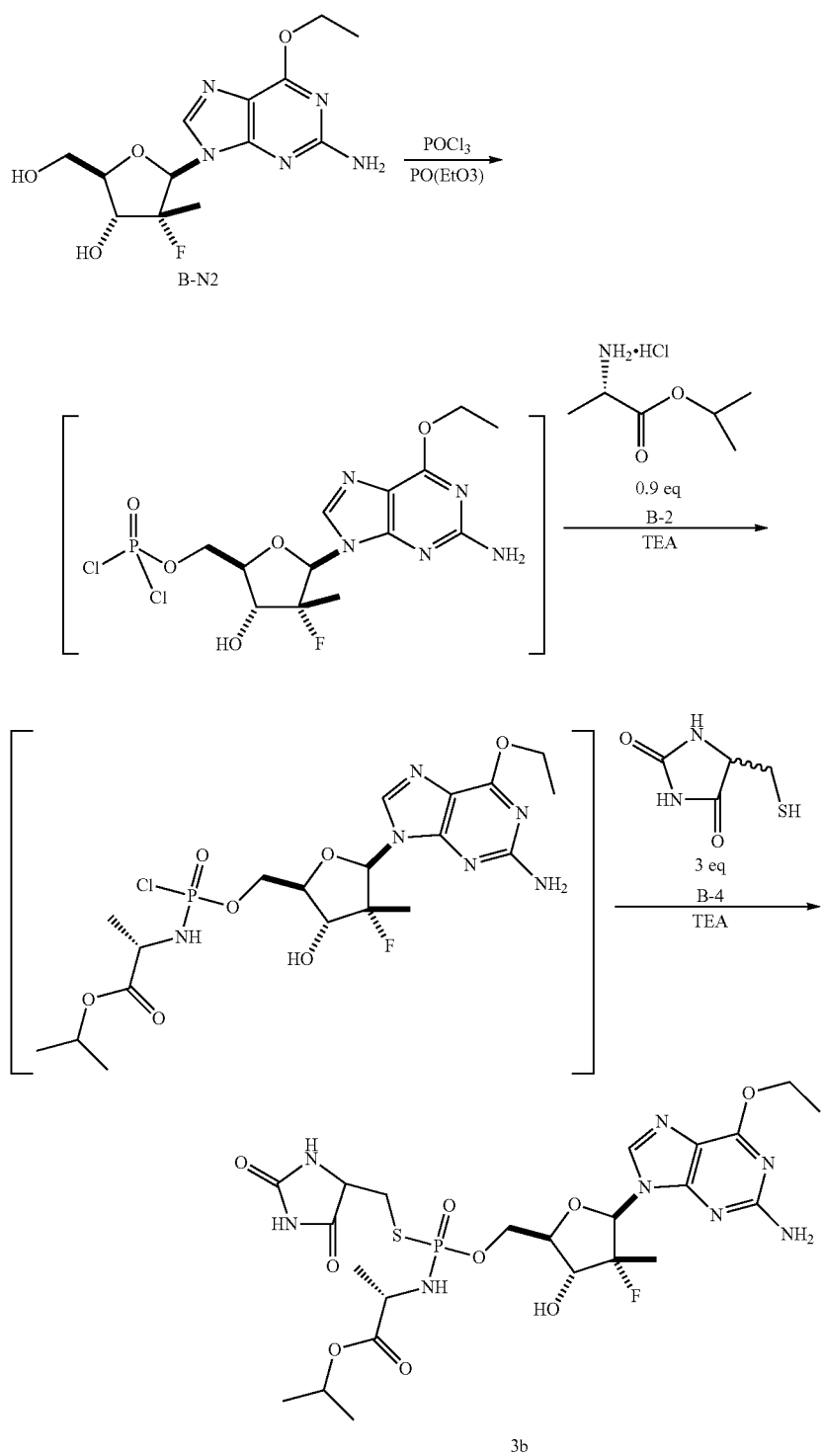
3b
Chemical Formula: $C_{23}H_{34}FN_8O_9PS$
Molecular Weight: 648.6014

The nucleoside (B-N2, 1.5 g, 4.82 mmol) was stirred in triethylphosphate (PO(OEt)$_3$, 30 mL) and was cooled to −20° C. Phosphorous oxychloride (POCl$_3$, 0.96 g, 6.26 mmol, 1.3 eq) was added drop-wise and the mixture was stirred at −20° C. for 30 min. The mixture was allowed to warm to 0° C. and was stirred at this temperature for 4 hours. This mixture was cooled to −50° C. (dry ice/EtOH) B-2 (0.724 g, 4.34 mmol, 0.9 eq) was added followed by triethylamine (TEA, 1.54 mL, 11.08 mmol, 2.3 eq). After stirring at −50° C. for 30 minutes, B-4 (2.11 g, 14.46 mmol, 3 eq) was added and the mixture followed by triethylamine (TEA, 2.88 mL, 20.72 mmol, 4.3 eq). The mixture was allowed to warm to room temperature and was stirred overnight. Petroleum ether was added to the mixture and the precipitated material was isolated by vacuum filtration. This material was purified by column chromatography (silica gel, 200-300 mesh) using MeOH/DCM (0→7%) providing the crude product (570 mg). The crude product was purified by preparative column chromatography affording compound 3b, diastereomer 1 (10 mg, 0.33%) and compound 3b, diastereomer 2 (10 mg, 0.33%).

Compound 3b, Diastereomer 1

HPLC (Method 4), RT 27.68 min, 97.5 A %; LCMS (ES$^+$, m/e=649.2, M$^+$+1); $^1$H NMR (300 MHz, CD$_3$OD) δ 7.94 (s, 1H), 6.16 (d, 1H), 4.96 (m, 1H), 4.47 (m, 6H), 4.20 (m, 1H), 4.00 (m, 1H), 3.78 (m, 1H), 3.56 (m, 1H), 3.32 (d, 3H), 1.43 (t, 3H), 1.35 (m, 3H), 1.20 (m, 6H); $^{31}$P NMR (121 MHz, CD$_3$OD) δ 7.39.

Compound 3b, Diastereomer 2

HPLC (Method 4), RT 28.47 min, 97.4 A %; LCMS (ES$^+$, m/e=649.0, M$^+$+1); $^1$H NMR (300 MHz, CD$_3$OD) δ 7.90 (s, 1H), 6.17 (d, 1H), 4.97 (m, 1H), 4.47 (m, 6H), 4.20 (m, 1H), 4.00 (m, 1H), 3.78 (m, 1H), 3.62 (m, 1H), 3.31 (d, 3H), 1.44 (t, 3H), 1.35 (m, 3H), 1.23 (m, 6H); $^{31}$P NMR (121 MHz, CD$_3$OD) δ 7.52.

HPLC Method 4:

C18, 4.6×150 mm, 5 micron, 0.1% Ammonium acetate, 15%-18%-20%-35%-97% MeCN (0-10-35-45-50 min), 250 nm.

Compound 4b

Two Diastereomers Isolated From a Four Isomer Mixture

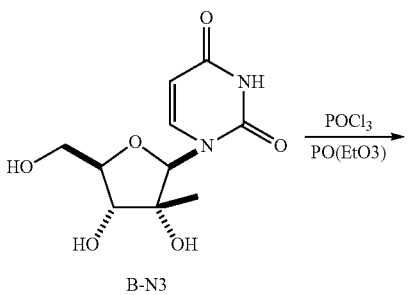

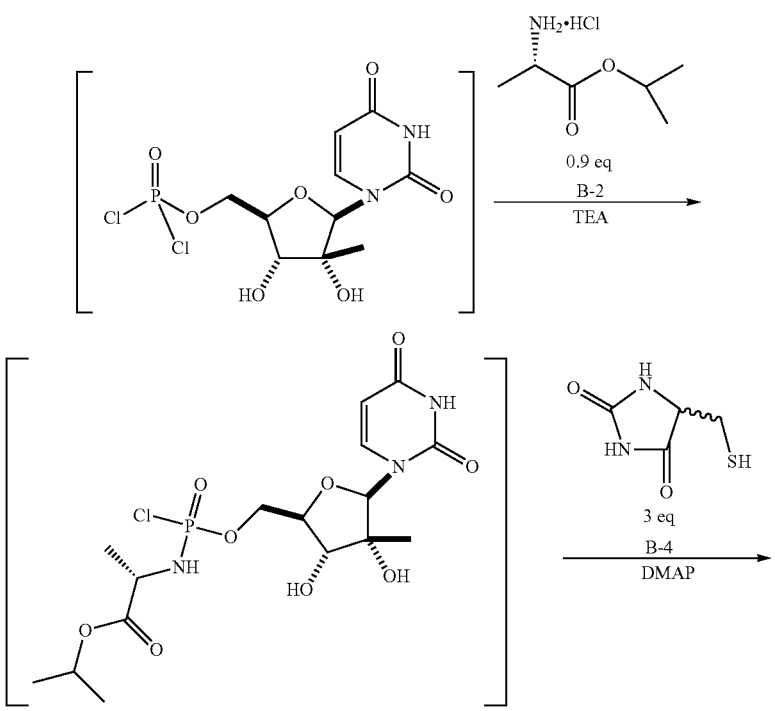

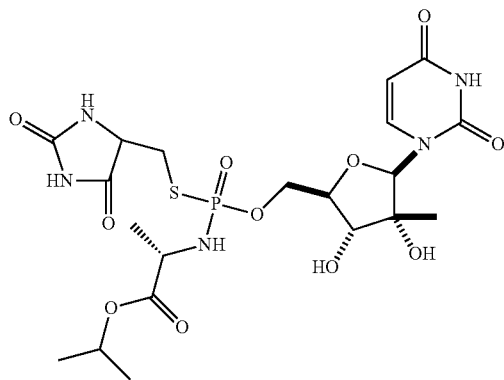

4b

Chemical Formula: $C_{20}H_{30}N_5O_{11}PS$
Molecular Weight: 579.5179

The nucleoside (B-N3, 0.8 g, 3.1 mmol) was stirred in triethylphosphate (PO(OEt)$_3$, 15 mL) 1,8-bis(dimethylamino)naphthalene (0.8 g, 3.721 mmol, 1.2 eq) was added and the mixture was cooled to −20° C. Phosphorous oxychloride (POCl$_3$, 0.96 g, 6.26 mmol, 1.3 eq) was added drop-wise and the mixture was stirred at −20° C. for 10 min. The mixture was allowed to warm to 0° C. and was stirred at this temperature for 30 min. This mixture was then cooled to −50° C. (dry ice/EtOH) B-2 (0.47 g, 2.79 mmol, 0.9 eq) was added followed by triethylamine (TEA, 0.99 mL, 0.713 mmol, 2.3 eq). After stirring at −50° C. for 30 minutes, B-4 (1.36 g, 0.93 mmol, 3 eq) was added to the mixture followed by 4-dimethylaminopyridine (DMAP, 0.94 g, 0.77 mmol, 2.5 eq). The mixture was allowed to warm to room temperature and was stirred overnight. Petroleum ether was added to the mixture and the precipitated material was isolated by vacuum filtration. This material was purified by column chromatography (silica gel, 200-300 mesh) using MeOH/DCM (0→7%) providing the crude product (570 mg). The crude product was purified by preparative column chromatography affording compound 4b, diastereomer 1 (30 mg, 1.7%) and compound 4b, diastereomer 2 (50 mg, 2.8%).

Compound 4b, Diastereomer 1

HPLC (Method 5), RT 18.81 min, 95.62 A %; LCMS (ES$^+$, m/e=580.0, M$^+$+1); $^1$H NMR (300 MHz, CD$_3$OD) δ 7.73 (d, 1H), 5.95 (s, 1H), 5.76 (d, 1H), 4.98 (m, 1H), 4.44 (m, 3H), 4.06 (m, 2H), 3.82 (m, 2H), 3.53 (m, 1H), 1.42 (m, 3H), 1.25 (m, 6H), 1.17 (s, 3H); $^{31}$P NMR (121 MHz, CD$_3$OD) δ 7.52.

Compound 4b, Diastereomer 2

HPLC (Method 5), RT 21.37 min, 95.9 A %; LCMS (ES$^+$, m/e=580.0, M$^+$+1); $^1$H NMR (300 MHz, CD$_3$OD) δ 7.77 (d, 1H), 5.98 (s, 1H), 5.84 (d, 1H), 5.02 (m, 1H), 4.48 (m, 2H), 4.31 (m, 1H), 4.05 (m, 2H), 3.82 (m, 2H), 3.53 (m, 1H), 1.38 (d, 3H), 1.26 (t, 6H), 1.17 (s, 3H); $^{31}$P NMR (121 MHz, CD$_3$OD) δ 7.06.

HPLC Method 5:

C18, 4.6×150 mm, 5 micron, 0.1% Ammonium acetate, 7%-15%-30%-97% MeCN (0-25-30-35 min), 250 nm.

Compound 5bx

Two Diastereomers Isolated From a Four Isomer Mixture

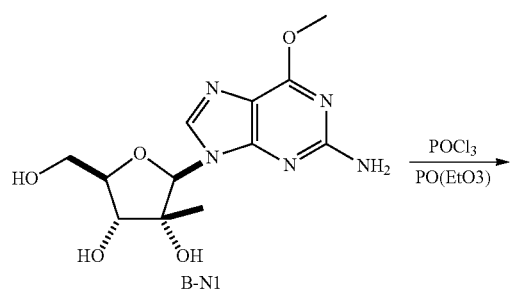

B-N1

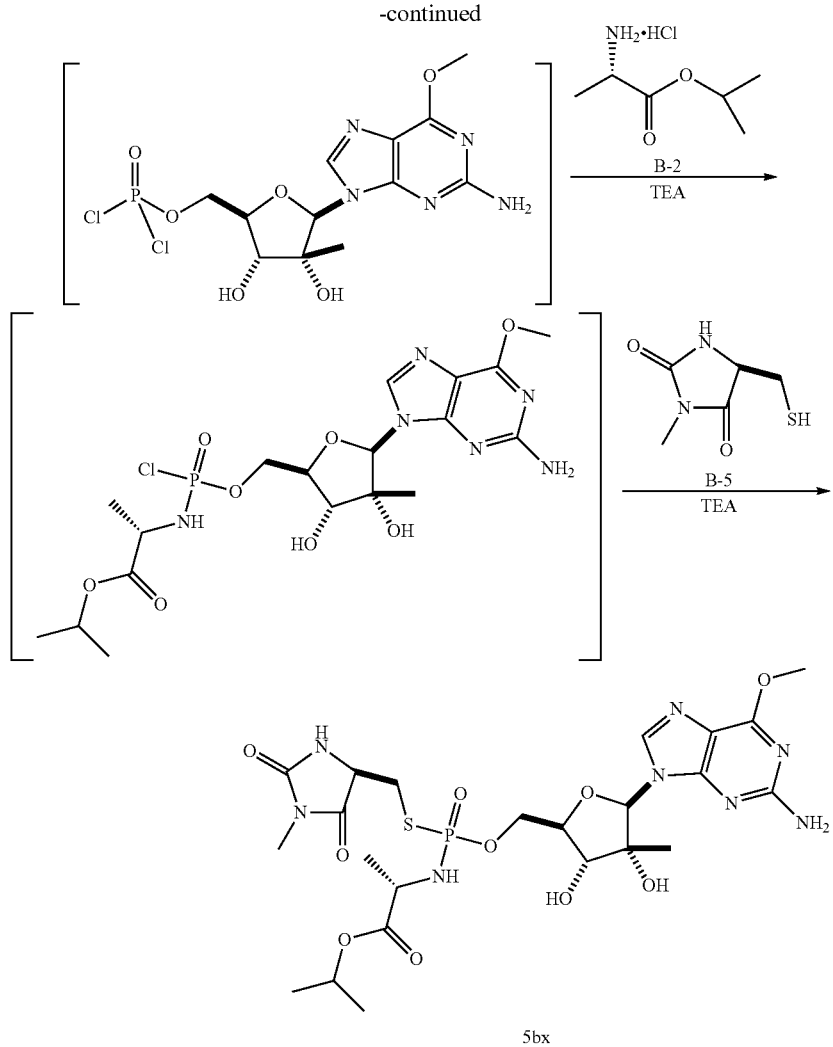
5bx
Chemical Formula: $C_{23}H_{35}N_8O_{10}PS$
Molecular Weight: 646.6104
B-2 was prepared as described herein. B-5 was prepared according to the following scheme:
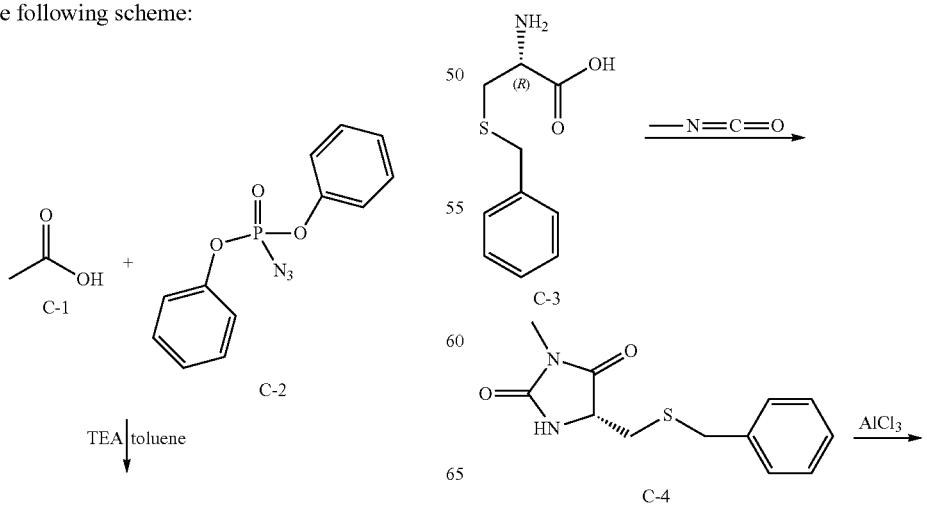

-continued

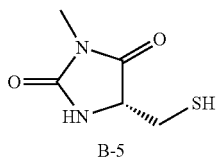

B-5

Preparation of Methyl Isocyanate

Acetic Acid (8.4 g, 139.9 mmol, 1 eq) was dissolved in toluene (75 mL) in a reaction vessel which had been outfitted for distillation. Triethylamine (19.4 mL, 139.9 mmol, 1 eq) was added and the mixture was heated to 70° C. Diphenyl phosphorazidate (50 g, 181.8 mmol, 1.3 eq) was slowly added drop-wise. After the addition had completed, the mixture was heated to 110° C. and the product was collected as a solution in toluene. After 40 mL of distillate had been collected, the mixture was cooled to room temperature and the concentration of the methyl isocyanate was determined by NMR (2.4 M, 70%).

The amino acid, (C-3, 3.52 g, 16.65 mmol, 0.95 eq) was dissolved in aqueous NaOH (1.75M, 10 mL). Methyl isocyanate (1.00 g. 17.53 mmol, 1 eq) was added as a solution in toluene. The mixture was stirred at room temperature and was acidified by the addition of aqueous HCl (20%, 35 mL). The mixture was heated at reflux temperature for 30 minutes. When the mixture was cooled, the desired product precipitated as a solid. The solid C-4 was isolated by filtration, was washed with distilled water, and was dried to provide 3 g (72%) of the desired product.

This material C-4 (4.8 g, 19.3 mmol, 1 eq) was dissolved in toluene (100 mL) at 0° C. and AlCl$_3$ (10.3 g, 77.27 mmol, 4 eq) was added. The mixture was stirred at room temperature for 15 h. The reaction mixture was quenched on addition of AcOH and diluted with methanol. The mixture was concentrated under reduced pressure and purified by flash column chromatography (silica gel, petroleum ether: ethyl acetate 10:1 to 1:1) to give B-5 (1.0 g).

The nucleoside (B-N1, 1.5 g, 4.82 mmol) was stirred in triethylphosphate (PO(OEt)$_3$, 30 mL) and was cooled to 0° C. Phosphorous oxychloride (POCl$_3$, 0.96 g, 6.26 mmol, 1.3 eq) was added drop-wise and the mixture was stirred at 0° C. for 3 hours. B-2 (0.724 g, 4.34 mmol, 0.9 eq) was added followed by triethylamine (TEA, 1.54 mL, 11.08 mmol, 2.3 eq). After stirring for 1 hour at 0° C., B-5 (1.16 g, 7.23 mmol, 1.5 eq) was added to the mixture followed by 1,9-diazabicycloundec-7-ene (DBU, 1.47 g, 9.64 mmol, 2 eq). The mixture was allowed to warm to room temperature and was stirred overnight. Petroleum ether (300 ml) was added to the mixture and the precipitated material was isolated by vacuum filtration. This material was purified by flash column chromatography (silica gel) using MeOH/DCM (1→4.5%) providing 5bx (2 g). 5bx was purified twice by preparative (RP) column chromatography affording compound 5bx, diastereomer 1 (35 mg) and compound 5bx, diastereomer 2 (34 mg).

Compound 5bx, Diastereomer 1

HPLC (Method 6), RT 14.41 min, 95.25 A %; LCMS (ES$^+$, m/e=647.1, M$^+$+1); $^1$H NMR (300 MHz, CD$_3$OD) δ 7.97 (s, 1H), 5.98 (s, 1H), 5.02 (m 1H), 4.52 (m, 2H), 4.35 (m, 2H), 4.24 (m, 1H), 4.06 (s, 3H), 3.90 (m, 1H), 3.27 (m 1H), 3.14 (m, 1H), 2.93 (s, 3H), 1.36 (m, 3H), 1.24 (d, 6H), 1.00 (s, 3H); $^{31}$P NMR (121 MHz, CD$_3$OD) δ 34.91.

Compound 5bx, Diastereomer 2

HPLC (Method 6), RT 16.44 min, 95.31 A %; LCMS (ES$^+$, m/e=647.1, M$^+$+1); $^1$H NMR (300 MHz, CD$_3$OD) δ 7.98 (s, 1H), 5.98 (s, 1H), 4.99 (m, 1H), 4.50 (m, 4H), 4.22 (m, 1H), 4.06 (s, 3H), 3.95 (m, 1H), 3.42 (m, 1H), 3.22 (m, 1H), 2.96 (s, 3H), 1.35 (m, 3H), 1.23 (m, 6H), 0.99 (s, 3H); $^{31}$P NMR (121 MHz, CD$_3$OD) δ 34.79.

HPLC Method 6:
C18, 4.6×150 mm, 5 micron, 0.1% Ammonium acetate, 15%-20%-40%-97% MeCN (0-25-30-35 min), 282 nm.

Compound 6

Two Diastereomers Isolated From a Four Isomer Mixture

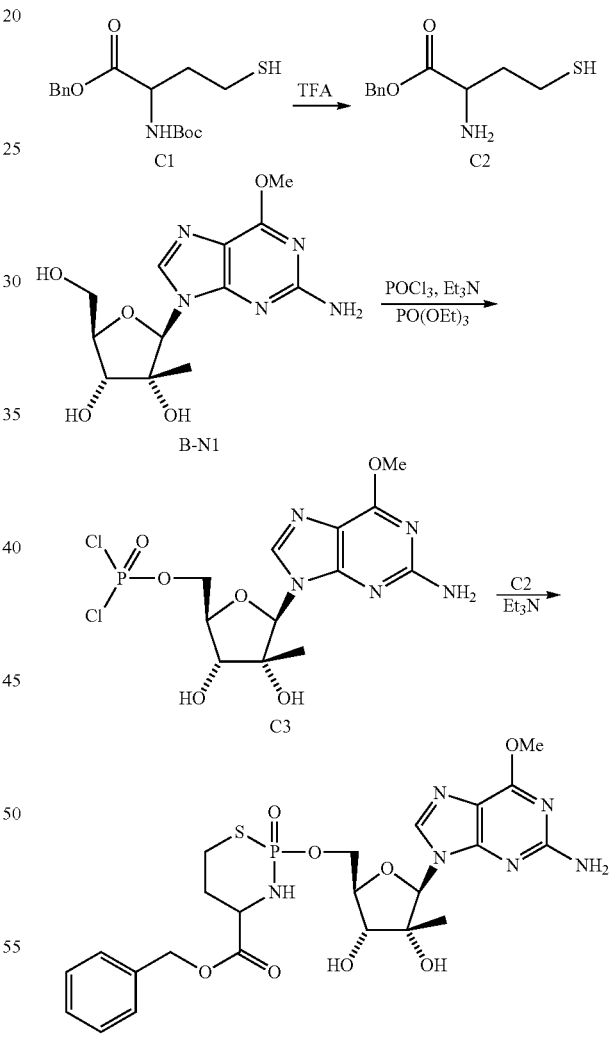

6
Chemical Formula: C$_{23}$H$_{29}$N$_6$O$_8$PS
Molecular Weight: 580.5505

C2. A solution of trifluoroacetic acid (TFA, 340 mg, 3 mmol, 3 eq) in DCM (10 mL) was added to a solution of the BOC protected amine (C1, 325 mg, 1 mmol, 1 eq) in DCM (10 mL) at 0° C. under a nitrogen atmosphere. The mixture was allowed to warm and was stirred at room temperature for 1 hour. The mixture was diluted with DCM (20 mL) and was washed with a saturated solution of sodium bicarbonate followed by brine. The organic solution was dried over sodium sulfate and was concentrated under reduced pressure to provide C2 (270 mg, quant).

The nucleoside (B-N1, 310 mg, 1.00 mmol, 1.0 eq) was stirred in triethylphosphate (PO(OEt)$_3$, 10 mL). Triethylamine (121 mg, 1.2 mmol, 1.2 eq) was added and the solution was cooled to 0° C. under a nitrogen atmosphere. Phosphorous oxychloride (POCl$_3$, 184 mg, 153 mmol, 1.2 eq) was added drop-wise and the mixture was stirred at 0° C. for 2 hours. Triethylamine (404 mg, 4.0 mmol, 4.0 eq) was added and the mixture was stirred at 0° C. A solution of C2 (270 mg, 1.2 mmol, 1.2 eq) in DCM (10 mL) was added drop-wise, the mixture was allowed to warm to room temperature and was stirred overnight. The reaction mixture was poured into petroleum ether (100 ml) and the precipitated material was isolated by vacuum filtration. The precipitate was dissolved in DCM (50 mL), was washed with brine, and was dried over sodium sulfate. This material was purified by flash column chromatography (silica gel) using MeOH/DCM (1:30 to 1:20) providing 6 as a mixture of four isomers. The four isomers were separated by preparative HPLC to provide compound 6, diastereomer 1 (36 mg) and compound 6, diastereomer 2 (43 mg) along with a mixture of the other two diastereomers (42 mg).

Compound 6, Diastereomer 1

HPLC (Method 7), RT 6.69 min, 99.15 A %; LCMS (ES$^+$, m/e=581.0, M$^+$+1); $^1$H NMR (300 MHz, CDCl$_3$) δ 7.73 (s, 1H), 7.30 (m, 5H), 5.89 (s, 1H), 5.34 (br-s, 2H), 5.20 (m, 2H), 4.74 (m, 2H), 4.19-4.32 (m, 4H), 3.97 (s, 3H), 3.09 (m, 2H), 2.21 (m, 2H), 1.00 (s, 3H); $^{31}$P NMR (121 MHz, CDCl$_3$) δ 29.28.

Compound 6, Diastereomer 2

HPLC (Method 7), RT 7.62 min, 98.97 A %; LCMS (ES$^+$, m/e=581.0, M$^+$+1); $^1$H NMR (300 MHz, CDCl$_3$) δ 7.85 (s, 1H), 7.30 (m, 5H), 6.01 (s, 1H), 5.30 (br-s, 2H), 5.13 (m, 2H), 4.88 (m, 1H), 4.48 (m, 2H), 4.42 (m, 3H), 4.02 (s, 3H), 3.04 (m, 2H), 2.10 (m, 2H), 0.98 (s, 3H); $^{31}$P NMR (121 MHz, CDCl$_3$) δ 31.50.

HPLC Method 7:

C18, 4.6×150 mm, 5 micron, 0.1% Ammonium acetate, 22%-29%-97% MeCN (0-12-17 min), 250 nm.

Compound 7b

Two Diastereomers Isolated From a Two Isomer Mixture

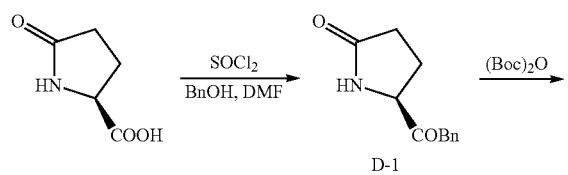

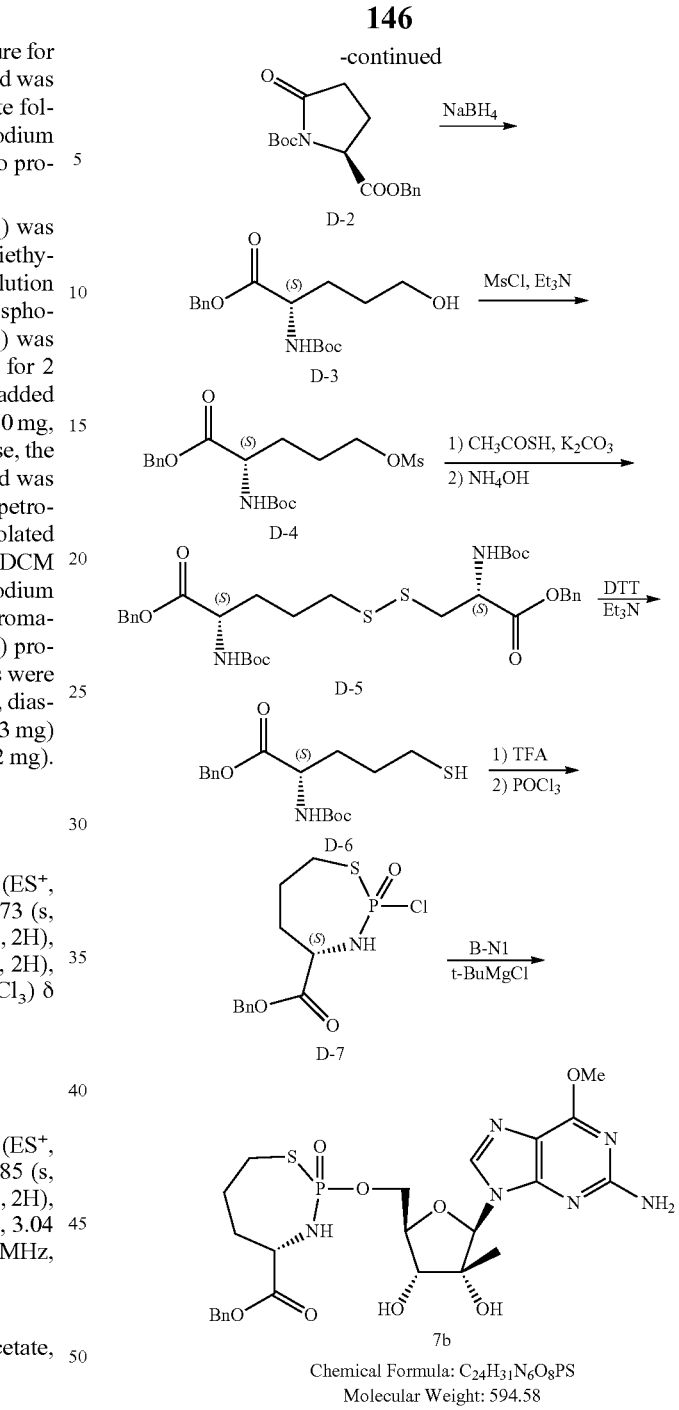

Chemical Formula: C$_{24}$H$_{31}$N$_6$O$_8$PS
Molecular Weight: 594.58

L-Pyroglutamic acid (12.9 g, 100 mmol, 1.0 eq) was dissolved in a 1:1 mixture of benzyl alcohol and DMF (100 mL). The mixture was cooled to 0° C. and thionyl chloride (15 g, 150 mmol, 1.5 eq) was added drop-wise. The mixture was allowed to warm to room temperature and was stirred overnight. The reaction mixture was concentrated and the crude product was purified by column chromatography (silica gel) to afford D-1 (10 g, 49%).

D-1 (8 g, 36.5 mmol, 1 eq) was dissolved in DCM (150 mL). The mixture was stirred and was cooled to 0° C. Dimethylaminopyridine (DMAP, 4.9 g, 40.1 mmol, 1.1 eq) was added followed by Boc-anhydride ((BOC)$_2$O, 8.75 g, 40.1 mmol, 1.1 eq). The mixture was allowed to warm to room temperature and was stirred for 2 hours. The mixture was then diluted with DCM (250 mL) and was washed successively with aqueous HCl (1N, 50 mL), aqueous saturated bicarbonate solution (350 mL) and brine. The organic phase was dried over sodium sulfate, was concentrated under reduced pressure, and was purified by silica gel chromatography to provide D-2 (8.6 g, 73.8%). LCMS (ES$^+$, m/e=656, [2M+NH$_4^+$]).

A solution of potassium dihydrogen phosphate (K$_2$H$_2$PO$_4$, 2.6 g, 19 mmol, 7.3 eq) in a mixture of methanol and water (5:1, 30 mL) was prepared. D-2 (823 mg, 2.6 mmol, 1 eq) was added and the mixture was cooled to 0° C. Sodium borohydride (700 mg, 19 mmol, 7.3 eq) was added and the mixture was stirred at 0° C. for 2 hours. Acetic acid (2 mL) was added and the mixture was stirred for another 20 minutes. The mixture was filtered and the filtrate was concentrated under reduced pressure. The resulting residue was extracted with ether. The ether solution was dried over sodium sulfate, was concentrated under reduced pressure, and the residue was purified by column chromatography (silica gel) to afford D-3 (100 mg, 12%). LCMS (ES$^+$, m/e=346, [M+Na]$^+$).

D-3 (460 mg, 1.4 mmol, 1 eq) was dissolved in DCM (2.5 mL). Triethylamine (200 mg, 2 mmol, 1.5 eq) was added and the mixture was stirred at 0° C. under a nitrogen atmosphere. Methane sulfonylchloride (MsCl, 205 mg, 1.8 mmol, 1.2 eq) was added and the mixture was stirred for 2 hours. The reaction mixture was diluted with DCM and was washed successively with cold aqueous HCl (1N, 5 mL), aqueous saturated bicarbonate solution (5 ml) and brine (5 mL). The organic phase was dried over sodium sulfate and was concentrated under reduced pressure. The residue was purified by column chromatography (silica gel) to afford D-4 (350 mg, 49%).

D-4 (5.3 g, 13.2 mmol, 1 eq) was dissolved in THF (40 mL). Potassium carbonate (2.1 g, 26.4 mmol, 2.2 eq) was added followed by thioacetic acid (1.2 mL, 26.4 mmol, 2.2 eq). The mixture was allowed to stir at room temperature overnight. The reaction mixture was diluted with THF (50 mL). Ammonium hydroxide (14.7 M, 30 mL) and water (50 mL) were added and the mixture was stirred at room temperature for 20 minutes. The mixture was then acidified with HCl (12N) and was extracted with DCM. The organic phase was dried over sodium sulfate and was concentrated under reduced pressure. The resulting residue was purified by silica gel chromatography to provide D-5 (2.2 g. 49%). LCMS (ES$^+$, m/e=677, [M+H]$^+$).

D-5 (300 mg, 0.44 mg, 1 eq) was dissolved in DCM (10 mL). Triethylamine (0.18 mL, 1.4 mmol, 3 eq) was added followed by dithiothreitol (DTT, 0.28 g, 1.8 mmol, 4 eq). The mixture was stirred at room temperature under a nitrogen atmosphere for 2 hours. The reaction mixture was diluted with DCM and was washed with 10% citric acid (15 mL) and water (15 mL). The organic phase was dried over sodium sulfate, was concentrated under reduced pressure and the residue was purified by silica gel column chromatography to afford D-6 (200 mg, 67%).

D-6 (400 mg) was treated with trifluoroacetic acid (3 mL) in DCM (10 mL) at 0° C. to remove the BOC protecting group. This mixture was concentrated and the crude material was dissolved in DCM. In a separate flask, phosphorous oxychloride (220 mg. 1.4 mmol, 1 eq) was dissolved in DCM (5 mL). The mixture was cooled to 0° C. and triethylamine (400 mg, 4 mmol, 2.8 eq) was added. The solution of the deprotected D-6 in DCM prepared in the first step was added and the mixture was stirred at 0° C. under nitrogen for 2 hours. The mixture was allowed to warm to room and was stirred for an additional 2 hours. The mixture was concentrated under vacuum and the residue, D-7, was dissolved in anhydrous THF for use in the coupling step.

The nucleoside (B-N1, 311 mg, 1 mmol, 1 eq) was dissolved in dry THF (3 mL). The mixture was cooled to 0° C., a solution of t-BuMgCl (1M in THF, 2 mL, 2 mmol, 2 eq) was added, and the mixture was stirred at 0° C. for 2 hours. The solution of D-7 (1.17 mmol) prepared above, was added dropwise. The mixture was allowed to warm to room temperature and was stirred overnight. The reaction mixture was diluted with DCM (5 mL) and was washed with water (15 mL) and brine (15 mL). The organic phase was dried over sodium sulfate, was concentrated under reduced pressure, and was purified by silica gel column chromatography to provide 7 (30 mg, 5%). The crude product was purified by preparative HPLC to provide samples of the two individual diastereomers compound 7b, diastereomer 1 (24 mg), and compound 7b, diastereomer 2 (21 mg).

Compound 7b, Diastereomer 1

HPLC (Method 8), RT 8.40 min, 97.32 A %; LCMS (ES$^+$, m/e=595.0, M$^+$+1); $^1$H NMR (300 MHz, CDCl$_3$) δ 8.05 (s, 1H), 7.65 (m, 5H), 5.88 (s, 1H), 5.35 (br-s, 2H), 5.18 (m, 2H), 4.80 (m, 3H), 4.25 (m, 3H), 4.06 (s, 3H) 3.10 (m, 1H), 2.91 (m, 1H), 2.25 (m, 2H), 1.38 (m, 2H), 1.00 (s, 3H); $^{31}$P NMR (121 MHz, CDCl$_3$) δ 40.12.

Compound 7b, Diastereomer 2

HPLC (Method 8), RT 7.21 min, 99.32 A %; LCMS (ES$^+$, m/e=594.9, M$^+$+1); $^1$H NMR (300 MHz, CDCl$_3$) δ 7.79 (s, 1H), 7.31 (m, 5H), 5.99 (s, 1H), 5.30 (br-s, 2H), 5.10 (m, 2H), 4.86 (m, 1H), 4.57 (m, 1H), 4.40 (m, 2H), 4.25 (m, 2H), 4.04 (s, 3H), 3.07 (m, 1H), 2.90 (m, 1H), 1.80-2.23 (m, 4H), 0.97 (s, 3H); $^{31}$P NMR (121 MHz, CDCl$_3$) δ 41.05.

HPLC Method 8:
C18, 4.6×150 mm, 5 micron, 0.1% Ammonium acetate, 25%-29%-97% MeCN (0-12-17 min), 250 nm.

Compound 8a

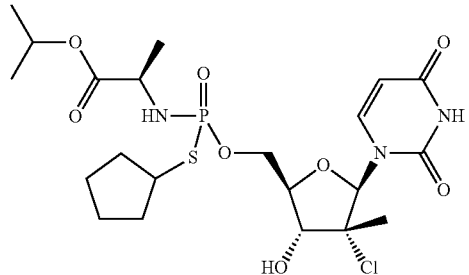 [SMILES: CC(C)OC(=O)[C@@H](C)NP(=O)(OC[C@H]1O[C@@H](n2ccc(=O)[nH]c2=O)[C@](C)(Cl)[C@@H]1O)SC1CCCC1]

Compound 8a was synthesized from 2'-chloro-2'-C-methyl-uridine and D-alanine isopropyl ester.HCl according to the procedure described for compound 8b in Scheme 1. The mixture of diastereoisomers was separated by MS-preparative HPLC.

Compound 8a Diastereomer 1

White solid; $^1$H NMR (MeOD, 400 MHz) δ (ppm) 1.25 (d, J=6.22 Hz, 6H), 1.41 (d, J=7.16 Hz, 3H), 1.54 (s, 3H), 1.61-

1.79 (m, 6H), 2.11-2.18 (m, 2H), 3.51-3.59 (m, 1H), 3.87-3.95 (m, 1H), 3.98-4.00 (m, 1H), 4.16-4.19 (m, 1H), 4.31 (ddd, J=11.93 Hz, J=5.97 Hz, J=2.61 Hz 1H), 4.51 (ddd, J=12.08 Hz, J=6.12 Hz, J=2.16 Hz, 1H), 5.00 (heptuplet, J=6.26 Hz, 1H), 5.76 (d, J=8.13 Hz, 1H), 6.39 (s, 1H), 7.83 (d, J=8.13 Hz, 1H); $^{31}$P NMR (MeOD, 161.98 MHz) δ (ppm) 34.12 (s, 1P); MS (ESI) m/z=554.2 (MH$^+$).

Compound 8a Diastereomer 2

White solid; $^1$H NMR (MeOD, 400 MHz) δ (ppm) 1.25 (d, J=6.25 Hz, 3H), 1.26 (d, J=6.25 Hz, 3H), 1.42 (d, J=7.18 Hz, 3H), 1.54 (s, 3H), 1.61-1.79 (m, 6H), 2.11-2.18 (m, 2H), 3.48-3.54 (m, 1H), 3.92-4.00 (m, 1H), 4.02-4.05 (m, 1H), 4.16-4.20 (m, 1H), 4.34 (ddd, J=11.94 Hz, J=6.46 Hz, J=2.74 Hz 1H), 4.49 (ddd, J=12.01 Hz, J=5.81 Hz, J=1.89 Hz, 1H), 5.00 (heptuplet, J=6.20 Hz, 1H), 5.78 (d, J=8.20 Hz, 1H), 6.41 (s, 1H), 7.84 (d, J=8.20 Hz, 1H); $^{31}$P NMR (MeOD, 161.98 MHz) δ (ppm) 34.18 (s, 1P); MS (ESI) m/z=554.2 (MH$^+$).

Example 2

HCV Replicon Assay

Huh-7-derived cell line (Zluc) that harbors an HCV genotype 1b replicon and a luciferase reporter gene was grown in Dulbecco's Modified Eagle Medium (DMEM) supplemented with 10% fetal bovine serum, 2 mM GlutaMAX, 1% MEM nonessential amino acids, 100 IU/mL penicillin, 100 μg/mL streptomycin, and 0.5 mg/mL Geneticin® (G418). For dose response testing the cells were seeded in 96-well plates at 7.5×10$^3$ cells per well in a volume of 50 μL, and incubated at 37° C./5% $CO_2$. Drug solutions were made up freshly in Huh-7 media as 2× stocks. Ten additional 5-fold dilutions were prepared from these stocks in DMEM without G418. At least three hours after Zluc cells were seeded, drug treatment was initiated by adding 50 μL of drug dilutions to the plates in duplicate. Final concentrations of drug ranged from 100 μM to 0.0000512 μM. Cells were then incubated at 37° C./5% $CO_2$. Alternatively, compounds were tested at two concentrations (1 μM and 10 μM). In all cases, Huh-7 (which do not harbors the HCV replicon) served as negative control. After 72 hours of incubation, the inhibition of HCV replication was measured by quantification of photons emitted after monooxygenation of 5'-fluoroluciferin to oxyfluoroluciferin by firefly luciferase. For this, media was removed from the plates via gentle tapping. Fifty microliters of ONE-glo luciferase assay reagent was added to each well. The plates were shaken gently for 3 min at room temperature and luminescence was measured on a Victor$^3$ V 1420 multilabel counter (Perkin Elmer) with a 1 second read time using a 700 nm cut-off filter. The EC$_{50}$ values were calculated from dose response curves from the resulting best-fit equations determined by Microsoft Excel and XLfit 4.1 software. When screening at two fixed concentrations, the results were expressed as % inhibition at 1 μM and 10 μM.

For cytotoxicity evaluation, Zluc cells were treated with test compound as described herein, and cell viability was monitored using the CellTiter-Blue Cell Viability Assay (Promega) by adding 20 μL of the assay solution to each well. The plates were then incubated at 37° C./5% $CO_2$ for at least 3 hours. Fluorescence was detected in plates using excitation and emission wavelengths of 560 and 590 nm, respectively, in a Victor$^3$ V 1420 multilabel counter (Perkin Elmer) and CC$_{50}$ values were determined using Microsoft Excel and XLfit 4.1 software.

Compounds presented in Table 1 below were assayed according to the replicon assay described herein.

TABLE 1

| HCV Replicon Activity | | | | | |
|---|---|---|---|---|---|
| Compound Reference | HCV Replicon | | Compound Reference | HCV Replicon | |
| | EC$_{50}$ | CC$_{50}$ | | EC$_{50}$ | CC$_{50}$ |
| Compound 1b Diastereomer 1 | ++ | ++ | Compound 1b Diastereomer 2 | + | ++ |
| Compound 23b Diastereomer 1 | ++ | ++ | Compound 23b Diastereomer 2 | ++ | ++ |
| Compound 3b Diastereomer 1 | ++ | ++ | Compound 3b Diastereomer 2 | ++ | ++ |
| Compound 4b Diastereomer 1 | + | ++ | Compound 4b Diastereomer 2 | + | ++ |
| Compound 8a Diastereomer 1 | + | ++ | Compound 8a Diastereomer 2 | + | ++ |
| Compound 8b Diastereomer 1 | ++ | ++ | Compound 8b Diastereomer 2 | +++ | ++ |
| Compound 5bx Diastereomer 1 | ++ | + | Compound 5bx Diastereomer 2 | ++ | + |
| Compound 6 Diastereomer 1 | ++ | ++ | Compound 6 Diastereomer 2 | ++ | ++ |
| Compound 7b Diastereomer 1 | + | ++ | Compound 7b Diastereomer 2 | ++ | ++ |
| Compound 9b Diastereomer 1 | ++ | ++ | Compound 9b Diastereomer 2 | ++ | ++ |
| Compound 12b Diastereomer 1 | + | ++ | Compound 12b Diastereomer 2 | ++ | ++ |
| Compound 11b Diastereomer 1 | ++++ | ++ | Compound 11b Diastereomer 2 | ++++ | ++ |
| Compound 14b Diastereomer 1 | + | ++ | Compound 14b Diastereomer 2 | ++ | ++ |
| Compound 16b Diastereomer 1 | + | ++ | Compound 16b Diastereomer 2 | + | ++ |
| Compound 15b | + | ++ | Compound 2by | ++ | ++ |
| Compound 10b | ++++ | ++ | Compound 13b | ++ | ++ |
| Compound 17b | + | ++ | | | |

EC$_{50}$ is provided as follows: ++++ ≤ 250 nM, 250 nM < +++ ≤ 1 μM, 1 μM < ++ ≤ 10 μM, 10 μM < +
CC$_{50}$ is provided as follows: + ≤ 50 μM, 50 μM < ++

All publications, patents, and patent applications cited in this specification are herein incorporated by reference as if each individual publication, patent, or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the claimed subject matter is limited solely by the scope of the following claims, including equivalents thereof.

What is claimed is:

1. A compound according to Formula I:

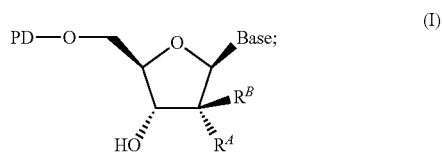

or a pharmaceutically acceptable salt, solvate, stereoisomeric form, tautomeric form, or polymorphic form thereof, wherein:

Base is a nucleobase;
$R^A$ is hydroxyl or fluoro;
$R^B$ is methyl or halo;
PD is

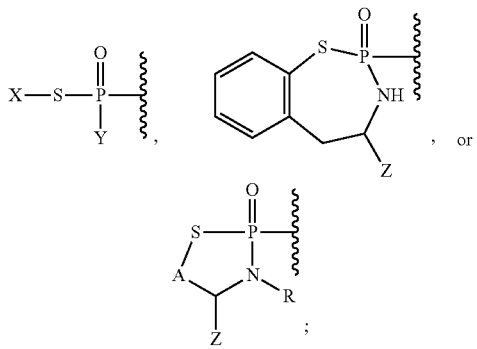, or

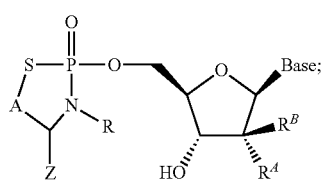;

X is alkyl, alkoxycarbonylalkyl, (alkoxycarbonyl)(alkoxycarbonylamino)alkyl, cycloalkyl, heterocycloalkyl, hydantoinylalkyl, or aryl;
Y is —$NR^1R^2$ or an N-linked amino acid, or ester thereof;
Z is alkyl, alkoxycarbonyl or alkoxyalkylcarbonyl;
A is —$CHR^{10}$—, —$CHR^{10}CHR^{11}$—, or —$CHR^{10}CHR^{11}CHR^{12}$—;
$R^1$ is hydrogen, alkyl, cycloalkyl, aryl, heteroaryl, arylalkyl, or heteroarylalkyl;
$R^2$ is hydrogen or alkyl;
R is hydrogen or alkyl; and
each of $R^{10}$, $R^{11}$, and $R^{12}$ is independently hydrogen or alkyl; or $R^{10}$ and $R^{11}$, together with the carbon atoms to which they are attached, combine to form a five-, six-, or seven-membered ring.

2. The compound of claim 1 according to Formula III:

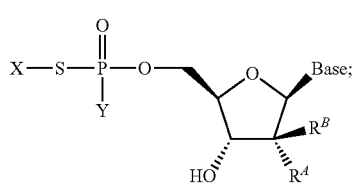

(III)

or a pharmaceutically acceptable salt, solvate, stereoisomeric form,-tautomeric form, or polymorphic form thereof.

3. The compound of claim 1 according to Formula II:

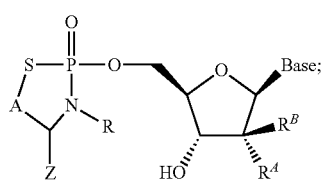

(II)

or a pharmaceutically acceptable salt, solvate, stereoisomeric form,-tautomeric form, or polymorphic form thereof.

4. The compound of claim 1 according to any of Formulas IV-VI:

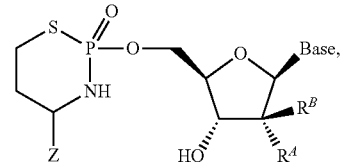

(IV)

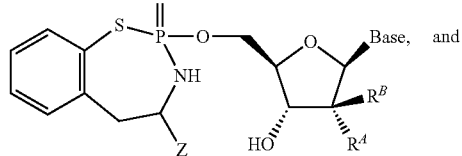

(V)

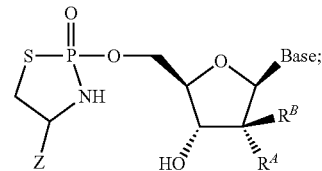

(VI)

or a pharmaceutically acceptable salt, solvate, stereoisomeric form,-tautomeric form, or polymorphic form thereof.

5. The compound of claim 1 according to Formula VII or VIII:

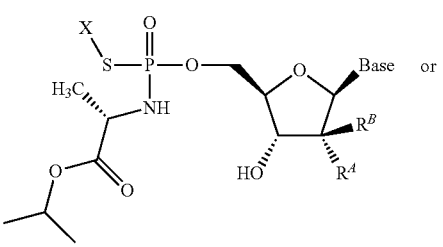

(VII)

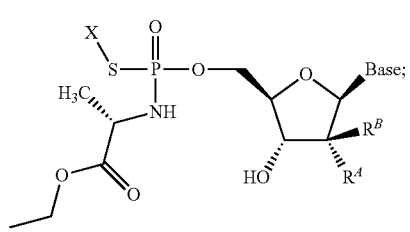

(VIII)

or a pharmaceutically acceptable salt, solvate, stereoisomeric form,-tautomeric form, or polymorphic form thereof.

6. The compound of claim 1, wherein Base is:

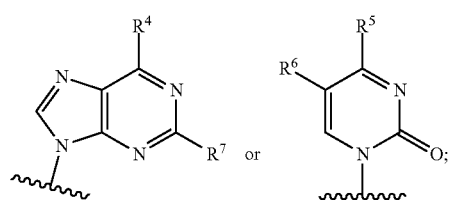

or tautomeric form thereof, wherein:

R⁴ is hydrogen, hydroxyl, unsubstituted alkoxyl, —NR¹'R²' or alkyl substituted with —NR¹'R²'; where each R¹' and R²' are independently selected from hydrogen, unsubstituted alkyl and unsubstituted cycloalkyl;

R⁵ is hydrogen, hydroxyl, —NR¹'R²' (where R¹' and R²' are independently selected from hydrogen, unsubstituted alkyl and unsubstituted cycloalkyl), or unsubstituted alkoxyl;

R⁶ is hydrogen, halogen, or unsubstituted alkyl; and

R⁷ is hydrogen or —NH₂.

7. The compound of claim 6 according to any of Formulas (IX)-(XII):

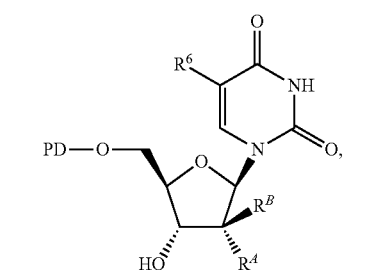
(IX)

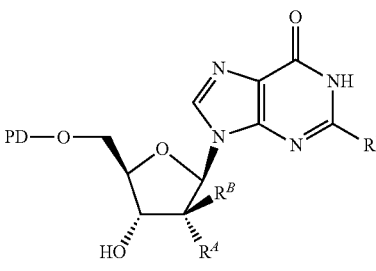
(X)

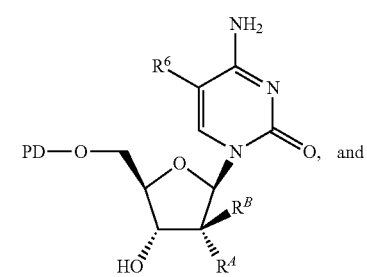
(XI)

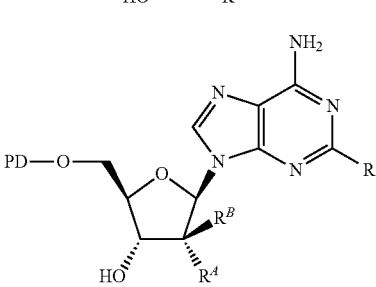
(XII)

or a pharmaceutically acceptable salt, solvate, stereoisomeric form, -tautomeric form, or polymorphic form thereof.

8. The compound of claim 1 according to any of Formulas XIII-XVII:

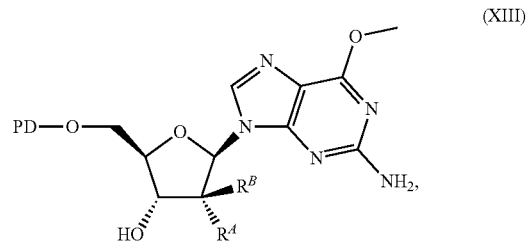
(XIII)

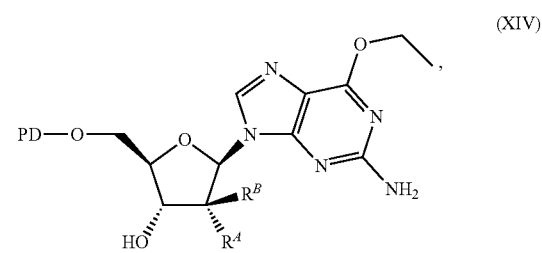
(XIV)

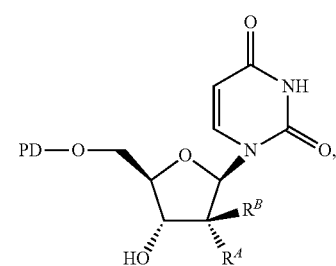
(XV)

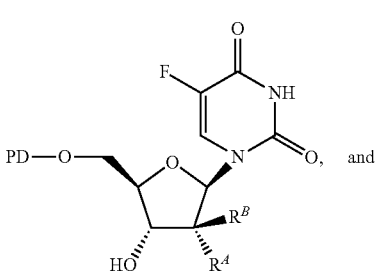
(XVI)

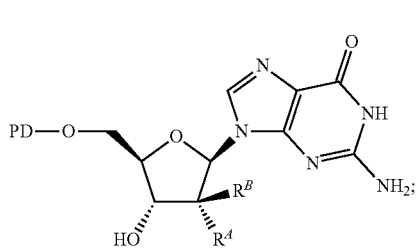
(XVII)

or a pharmaceutically acceptable salt, solvate, stereoisomeric form, -tautomeric form, or polymorphic form thereof.

9. A compound according to any of Formulas 1-23:
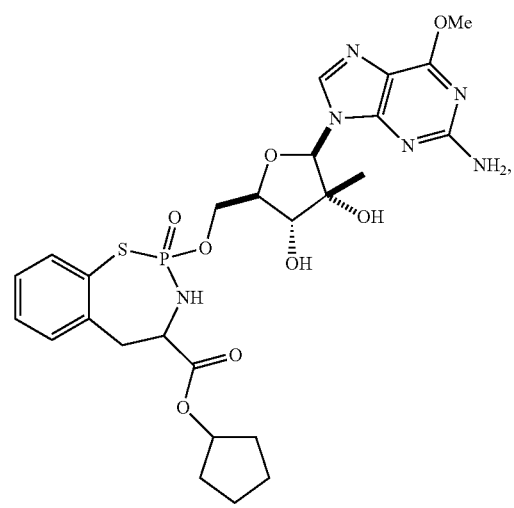
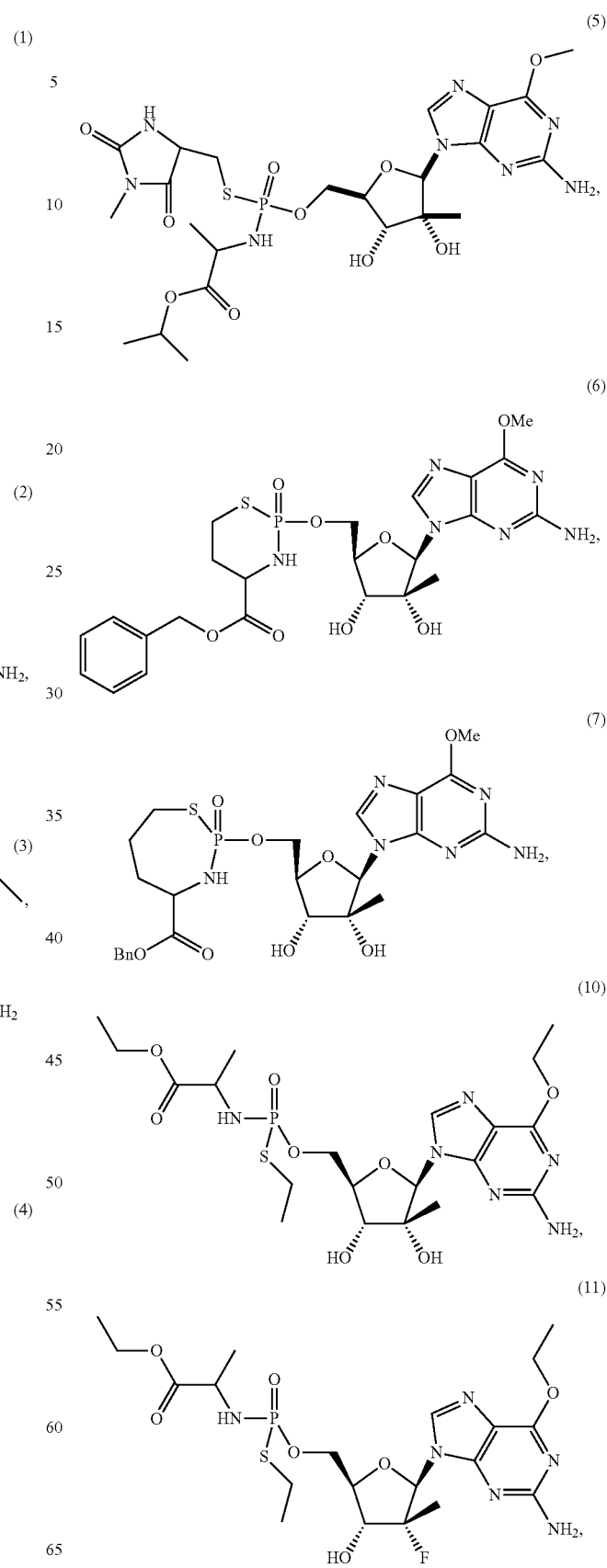

(12)
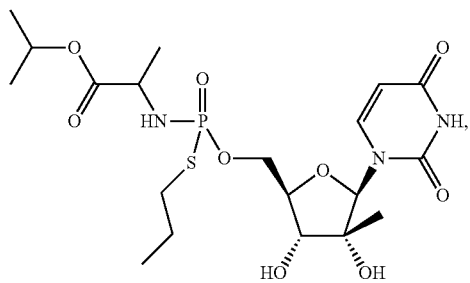
(13)
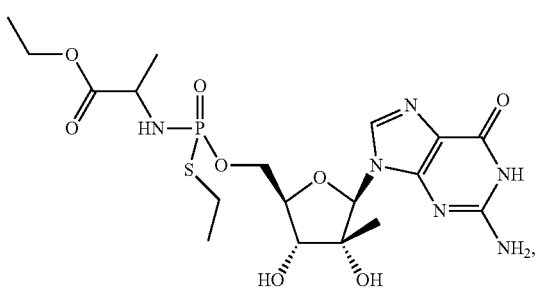
(15)
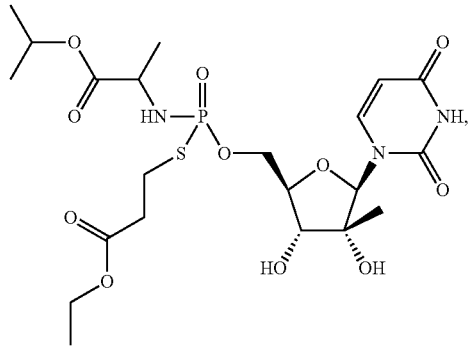
(16)
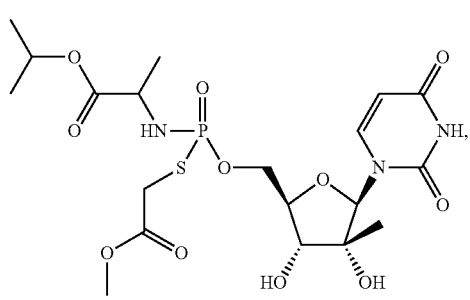
(18)
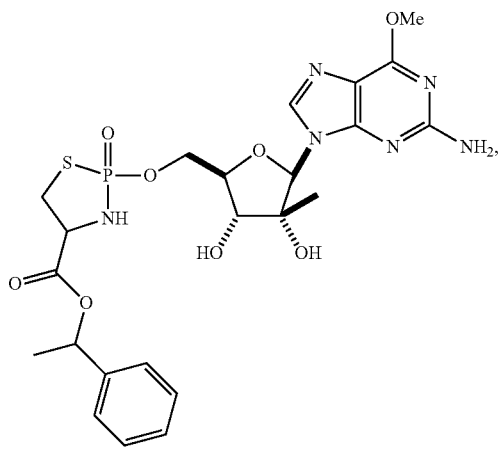
(19)
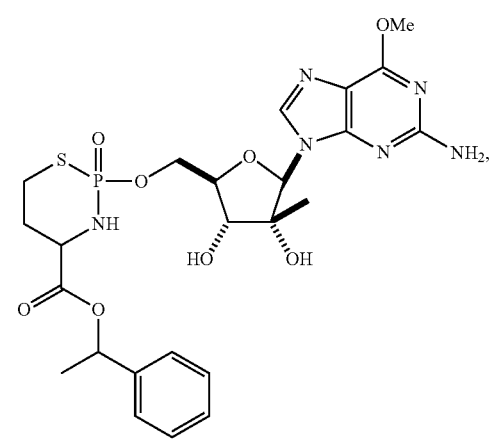
(20)
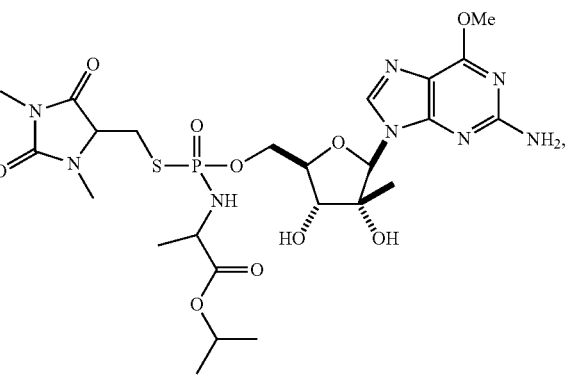

-continued

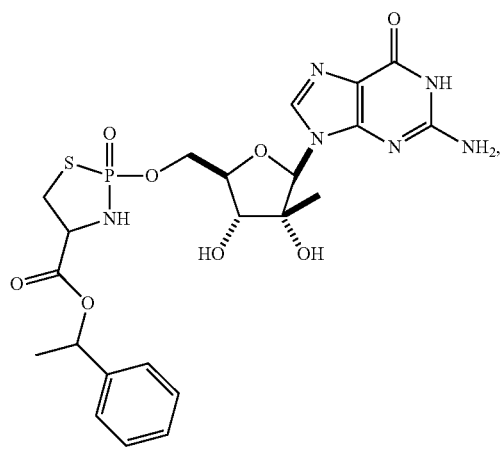
(21)

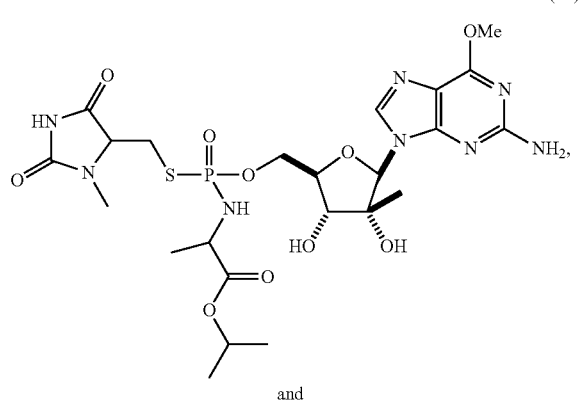
and
(22)

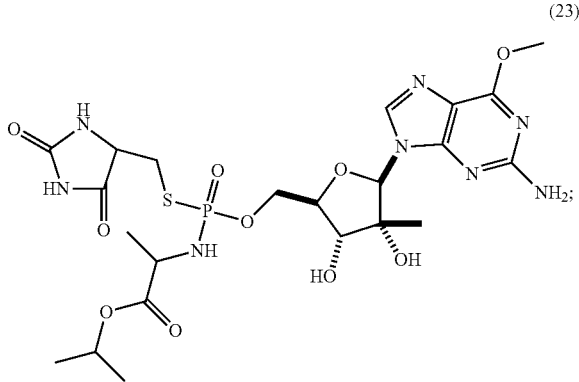
(23)

or a pharmaceutically acceptable salt, solvate, stereoisomeric form,-tautomeric form, or polymorphic form thereof.

10. A pharmaceutical composition comprising the compound of claim 1 and a pharmaceutically acceptable excipient, carrier, or diluent.

11. The pharmaceutical composition of claim 10, wherein the composition is an oral formulation.

12. A method for the treatment of a host infected with a hepatitis C virus, comprising the administration of an effective treatment amount of a compound of claim 1.

13. The method of claim 12, wherein the host is a human.

14. The method of claim 12, wherein the administration directs a substantial amount of the compound, or pharmaceutically acceptable salt or stereoisomer thereof, to a liver of the host.

15. The method of claim 12, wherein the compound is administered in combination or alternation with a second anti-viral agent, wherein the second anti-viral agent is an interferon, a nucleotide analogue, a polymerase inhibitor, an NS3 protease inhibitor, an NS5A inhibitor, an entry inhibitor, a non-nucleoside polymerase inhibitor, a cyclosporine immune inhibitor, an NS4A antagonist, an NS4B-RNA binding inhibitor, a locked nucleic acid mRNA inhibitor, a cyclophilin inhibitor, or combination thereof.

16. The method of claim 15, wherein the second anti-viral agent is IDX-719, TMC435, PSI-7977, telaprevir, boceprevir, interferon alfacon-1, interferon alfa-2b, pegylated interferon alpha 2a, pegylated interferon alpha 2b, ribavirin, and combinations thereof.

17. The method of claim 15, wherein the second anti-viral agent is IDX-719, TMC435, PSI-7977, telaprevir, boceprevir, interferon alfacon-1, interferon alfa-2b, pegylated interferon alpha 2a, pegylated interferon alpha 2b, and combinations thereof, and further wherein the administration is not in combination or alternation with ribavirin.

18. The compound of claim 1, wherein:

Base is

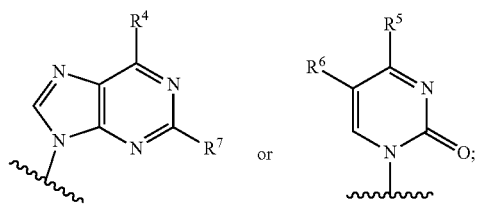

or a tautomeric form thereof;

$R^4$ is hydrogen, hydroxyl, unsubstituted alkoxyl, —$NR^{1'}R^{2'}$ or alkyl substituted with —$NR^{1'}R^{2'}$; where each $R^{1'}$ and $R^{2'}$ are independently selected from hydrogen, unsubstituted alkyl and unsubstituted cycloalkyl;

$R^5$ is hydrogen; hydroxyl; —$NR^{1'}R^{2'}$ where $R^{1'}$ and $R^{2'}$ are independently selected from hydrogen, unsubstituted alkyl and unsubstituted cycloalkyl; or unsubstituted alkoxyl;

$R^6$ is hydrogen, halogen, or unsubstituted alkyl; and $R^7$ is hydrogen or —$NH_2$;

$R^A$ is hydroxyl or fluoro;

$R^B$ is methyl or halo;

PD is

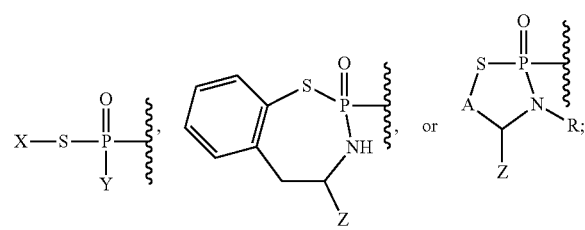

X is unsubstituted alkyl; substituted alkyl; alkoxycarbonylalkyl;

(alkoxycarbonyl)(alkoxycarbonylamino)alkyl; cycloalkyl; heterocycloalkyl;

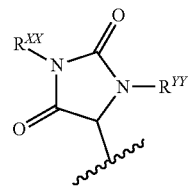

where $R^{XX}$ and $R^{YY}$ each independently hydrogen or unsubstituted lower alkyl; or aryl;

Y is —$NR^1R^2$, —$NR^X$-$G(S_C)$—C(O)-$Q^1$, or —O—C(O)-$G(S_C)$—NH-$Q^2$;

$R^1$ is hydrogen, unsubstituted alkyl, substituted alkyl, cycloalkyl, aryl, heteroaryl, -alkyl-(unsubstituted aryl), -alkyl-(substituted aryl), or heteroarylalkyl;

$R^2$ is hydrogen or unsubstituted alkyl;

$Q^1$ is —$SR^Y$, —$NR^YR^Y$ or unsubstituted alkoxyl;

$R^Y$ is hydrogen or unsubstituted alkyl;

$S_C$ is a side chain of a naturally occurring or non-naturally occurring amino acid; or $S_C$ is hydrogen, unsubstituted alkyl, substituted alkyl, -alkyl-(unsubstituted aryl), -alkyl-(substituted aryl), heterocycloalkyl, carboxylalkyl, heteroarylalkyl, alkyl substituted with —$NR^{1'}R^{2'}$ (where each $R^{1'}$ and $R^{2'}$ are independently selected from hydrogen, unsubstituted alkyl and unsubstituted cycloalkyl), hydroxylalkyl, -alkyl-NH—C(NH)—$NH_2$, -alkyl-C(O)$NH_2$, sulfanylalkyl, alkylsulfanylalkyl, or hydroxylarylalkyl;

G is $C_1$-$C_2$ alkyl;

$R^X$ is hydrogen or $R^X$ and $S_C$, together with the atoms to which they are attached, combine to form a five-membered heterocyclic ring;

$Q^2$ is hydrogen or unsubstituted alkoxyl; or $Q^2$ and $S_C$, together with the atoms to which they are attached, combine to form a five-membered heterocyclic ring;

Z is unsubstituted alkyl, substituted alkyl, alkoxycarbonyl or alkoxyalkylcarbonyl;

A is —$CHR^{10}$—, —$CHR^{10}CHR^{11}$—, or —$CHR^{10}CHR^{11}CHR^{12}$—;

R is hydrogen or unsubstituted alkyl;

each of $R^{10}$, $R^{11}$, and $R^{12}$ is independently hydrogen or unsubstituted alkyl; or $R^{10}$ and $R^{11}$, together with the carbon atoms to which they are attached, combine to form a five-, six-, or seven-membered ring;

each "alkyl," unless specified otherwise, is unsubstituted;

each alkoxy is —OR' where R' is unsubstituted alkyl or unsubstituted cycloalkyl;

each "substituted alkyl" is independently alkyl substituted with moiety(ies) selected from halogen; hydroxyl; sulfanyl; —$NR^{1'}R^{2'}$ where each $R^{1'}$ and $R^{2'}$ are independently selected from hydrogen, unsubstituted alkyl and unsubstituted cycloalkyl; —NH (unsubstituted aryl), —N(unsubstituted aryl)$_2$; —OR' where R' is unsubstituted alkyl or unsubstituted cycloalkyl; —O-(unsubstituted aryl); nitro; cyano; sulfonic acid; sulfate; phosphonic acid; and phosphate;

each cycloalkyl is a saturated, monocyclic hydrocarbon or a bridged or fused bicyclic hydrocarbon comprising 3 to 15 carbon atoms; the cycloalkyl is unsubstituted or substituted, unless otherwise specified, and when substituted is substituted with moiety(ies) selected from halogen; hydroxyl; sulfanyl; —$NR^{1'}R^{2'}$ where each $R^{1'}$ and $R^{2'}$ are independently selected from hydrogen, unsubstituted alkyl and unsubstituted cycloalkyl; —NH(unsubstituted aryl), —N(unsubstituted aryl)$_2$; —OR' where R' is unsubstituted alkyl or unsubstituted cycloalkyl; —O-(unsubstituted aryl); nitro; cyano; sulfonic acid; sulfate; phosphonic acid; and phosphate;

the heterocyclo in heterocycloalkyl is a monovalent, monocyclic, non-aromatic ring system or a fused or bridged, bicyclic, tricyclic, or tetracyclic ring system that is partially or fully saturated or aromatic provided that it contains at least one non-aromatic ring; wherein the heterocyclo comprises 3 to 20 ring atoms; wherein one or more of the non-aromatic ring atoms are heteroatoms independently selected from O, S, or N and the remaining ring atoms are carbon atoms and where the nitrogen or sulfur atoms may be optionally oxidized, and the nitrogen atoms may be optionally quaternized; and wherein the heterocyclo may be attached to the alkyl at any heteroatom or carbon atom which results in the creation of a stable compound; and wherein the heterocyclo ring is unsubstituted or substituted and when substituted is substituted with moiety(ies) selected from halogen; hydroxyl; alkoxycarbonyl; alkoxycarbonylalkyl; sulfanyl; —$NR^{1'}R^{2'}$ where each $R^{1'}$ and $R^{2'}$ are independently selected from hydrogen, unsubstituted alkyl and unsubstituted cycloalkyl; —NH(unsubstituted aryl), —N(unsubstituted aryl)$_2$; —OR' where R' is unsubstituted alkyl or unsubstituted cycloalkyl; —O-(unsubstituted aryl); nitro; cyano; sulfonic acid; sulfate; phosphonic acid; and phosphate;

each aryl is a $C_6$-$C_{12}$ aromatic group and is unsubstituted or substituted, unless otherwise specified, and when substituted is substituted with moiety(ies) selected from halogen; unsubstituted alkyl; substituted alkyl; haloalkyl; hydroxyl; —$NR^{1'}R^{2'}$ where each $R^{1'}$ and $R^{2'}$ are independently selected from hydrogen, unsubstituted alkyl and unsubstituted cycloalkyl; —NH(unsubstituted aryl), —N(unsubstituted aryl)$_2$; —OR' where R' is unsubstituted alkyl or unsubstituted cycloalkyl; —O-(unsubstituted aryl); nitro; cyano; sulfonic acid; sulfate; phosphonic acid; and phosphate; and each heteroaryl is a monovalent monocyclic aromatic group or multicyclic aromatic group that contains at least one aromatic ring; wherein the ring comprises 5 to 20 ring atoms; wherein at least one aromatic ring contains one to four heteroatoms independently selected from O, S, and N, provided that the ring contains at least one carbon atom; and where the heteroaryl is bonded to the rest of the molecule through the aromatic ring.

19. A pharmaceutical composition comprising the compound of claim 18 and a pharmaceutically acceptable excipient, carrier, or diluent.

20. A method for the treatment of a host infected with a hepatitis C virus, comprising the administration of an effective treatment amount of a compound of claim 18.

\* \* \* \* \*